US007888054B2

(12) United States Patent
Krah, III et al.

(10) Patent No.: US 7,888,054 B2
(45) Date of Patent: Feb. 15, 2011

(54) ***EHRLICHIA CANIS* DIVA (DIFFERENTIATE INFECTED FROM VACCINATED ANIMALS)**

(75) Inventors: Eugene Regis Krah, III, Freeport, ME (US); Melissa Beall, Cape Elizabeth, ME (US); Thomas Patrick O'Connor, Jr., Westbrook, ME (US); Ramaswamy Chandrashekar, Scarborough, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 12/262,709

(22) Filed: Oct. 31, 2008

(65) Prior Publication Data

US 2009/0110691 A1 Apr. 30, 2009

Related U.S. Application Data

(60) Provisional application No. 60/984,019, filed on Oct. 31, 2007.

(51) Int. Cl.
*G01N 33/569* (2006.01)
*G01N 33/53* (2006.01)

(52) U.S. Cl. ........................ 435/7.32; 435/7.1; 435/7.2; 435/69.1; 435/69.7; 530/300; 530/350

(58) Field of Classification Search ....................... None
See application file for complete search history.

(56) References Cited

U.S. PATENT DOCUMENTS

| | | | |
|---|---|---|---|
| 4,894,576 A | 1/1990 | Okamoto et al. | |
| 5,726,010 A | 3/1998 | Clark | |
| 6,043,085 A | 3/2000 | Yu et al. | |
| 6,355,777 B1 | 3/2002 | Walker et al. | |
| 6,392,023 B1 | 5/2002 | Walker et al. | |
| 6,403,780 B1 | 6/2002 | Walker et al. | |
| 6,458,942 B1 | 10/2002 | Walker et al. | |
| 6,660,269 B2 | 12/2003 | Walker et al. | |
| 2002/0115840 A1 | 8/2002 | Walker et al. | |
| 2003/0073095 A1 | 4/2003 | Walker et al. | |
| 2003/0092087 A1 | 5/2003 | Walker et al. | |
| 2003/0096250 A1 | 5/2003 | Walker et al. | |
| 2003/0185849 A1 | 10/2003 | Walker et al. | |
| 2004/0121433 A1 | 6/2004 | McBride et al. | |
| 2004/0170972 A1 | 9/2004 | Chang | |
| 2004/0198951 A1 | 10/2004 | Walker et al. | |
| 2004/0247616 A1 | 12/2004 | Walker et al. | |
| 2005/0260621 A1 | 11/2005 | McBride et al. | |
| 2006/0211062 A1 | 9/2006 | O'Connor, Jr. | |
| 2006/0234322 A1* | 10/2006 | Krah et al. | 435/7.32 |
| 2007/0003570 A1 | 1/2007 | Murtaugh et al. | |
| 2009/0004217 A1* | 1/2009 | Krah et al. | 424/190.1 |

FOREIGN PATENT DOCUMENTS

| | | |
|---|---|---|
| WO | WO 98/42743 | 10/1998 |
| WO | WO 00/12688 | 3/2000 |
| WO | WO 01/182862 | 11/2001 |
| WO | WO 03/089571 | 10/2003 |
| WO | WO 2004/042037 | 5/2004 |
| WO | WO 2006/107924 | 10/2006 |
| WO | WO 2006/138509 | 12/2006 |
| WO | WO 2008/112007 | 9/2008 |

OTHER PUBLICATIONS

Houghten et al. (Vaccines, 1986, Edited by Fred Brown: Cold Spring Harbor Laboratory).*
Holmes, Exp. Opin.Invest. Drugs, 2001, 10(3):511-519).*
Greenspan et al (Nature Biotechnology, 1999, 7:936-937).*
Waner et al., Vet. Parasitol., 95:1-15, 2001.*
Breitschwerdt, et al., "Doxycycline Hyclate Treatement of Experimental Canine Ehrlichiosis Followed by Challenge Inoculation with Two *Ehrliichia canis* Strains", Antimicrobial Agents and Chemotherapy, vol. 42, No. 2, p. 362-368, 1998.
Yu, et al., "Comparison of *Ehrlichia chaffeensis* Recombinant Proteins for Serologic Diagnosis of Human Monocytotropic Ehrlichiosis", Journal of Clinical Microbiology, vol. 37, No. 8, p. 2568-2575, 1999.
Yu, et al., "Molecular Cloning and characterization of the 120-Kilodalton Protein Gene of *Ehrlichia canis* and Application of the Recombinant 120-Kilodalton Protein for Serodiagnosis of Canine Ehrlichiosis", Journal of Clinical Microbiology, vol. 38, No. 1, p. 369-374, 2000.
McBride, et al., "Immunodiagnosis of *Ehrlichia canis* Infection with Recombinant Proteins", Journal of Clinical Microbiology, vol. 39, No. 1, p. 315-322, 2001.
Accession No. NZ_AAEJ01000001 dated Oct. 4, 2004 (first page only).
Accession No. ZP_00211244 dated Oct. 4, 2004.
Accession No. ZP_00211130 dated Oct. 4, 2004.
Accession No. AAE96254 dated Apr. 20, 2002.
Accession No. ZP_00210575 dated Oct. 4, 2004.
Accession No. AAK01145 dated Oct. 6, 2003.
Accession No. AF252298 dated Oct. 6, 2003.
Accession No. AAD34330 dated Jan. 13, 2000.
Accession No. AF112369 dated Jan. 13, 2000.
Accession No. ZP_00211146 dated Oct. 4, 2004.
Cardenas, et al. "Enzyme-Linked Immunosorbent Assay with Conserved Immunoreactive Glycoproteins gp36 and gp19 has Enhanced Sensitivity and Provides Species-Specific Immunodiagnosis of *Ehrlichia canis* Infection", Clinical and Vaccine Immunology, vol. 14, No. 2, p. 123-128 (2007).
McBride, et al., "Kinetics of Antibody Response to *Ehrlichia canis* immunoreactive Proteins", Infection and Immunity, vol. 71, No. 5, p. 2516-2524 (2003).
McBride, "Novel Immunoreactive glycoprotein orthologs of *Ehrlichia* spp.", Ann. NY Aca. Sci., 990:678-84, 2003—Abstract Only.

(Continued)

*Primary Examiner*—Larry R Helms
*Assistant Examiner*—Padma V Baskar
(74) *Attorney, Agent, or Firm*—McDonnell Boehnen Hulbert & Berghoff LLP

(57) ABSTRACT

The invention provides *Ehrlichia canis* antigens that can be used to detect *E. canis* infected animals regardless of whether the animals have been vaccinated for *E. canis*. The invention also provides compositions and methods for determining the presence of *E. canis* antigens and antibodies.

12 Claims, 8 Drawing Sheets

OTHER PUBLICATIONS

International Search Report and Written Opinion dated May 12, 2008, for corresponding PCT application No. PCT/US2007/080373.

Office action issued in corresponding U.S. Appl. No. 11/397,222 dated Nov. 19, 2007.

International Search Report and Written Opinion dated Feb. 2, 2007, for corresponding PCT application No. PCT.US2006/012432.

Waner, et al., "Significance of serological testing for ehrlichial diseases in dogs and with special emphasis on the diagnosis of canine moncytic ehrlichiosis caused by *Ehrlichia canis*", Veterinary Parasitology 95 (2001) 1-15.

Mavromatis, et al., "The Genome of the Obligately Intracellular Bacterium *Ehrlichia canis* Reveals Themes of Complex Membrane Strcutre and Immune Evasion Strategies", Journal of Bacteriology, vol. 188, No. 11, p. 4015-4023 (2006).

Office action issued in corresponding U.S. Appl. No. 11/397,222, dated Jul. 18, 2008.

Office action dated Jan. 21, 2010, U.S. Appl. No. 11/542,878 (US-2009-0004217).

Office action corresponding to U.S. Appl. No. 11/397,222 (U.S. Publ. No. 20060234322) dated Feb. 23, 2009.

Office Action issued in corresponding U.S. Appl. No. 11/542,878 (U.S. Publication No. 2009-0004217, published Jan. 1, 2009), dated Jun. 2, 2009.

Database, "Major outer membrane protein p19", Uniprot, Sep. 27, 2005. Retrieved from EBI Accession No. UNIPROT:Q3YSZ1, Database accession No. Q3YSZ1.

Mavromatis, et al., "The genome of the obligately intracellular bacterium *Ehrlichia canis* reveals themes of complex membrane structure and immune evasion strategies", J. Bacteriol. 2006; 88(11):4015-23.

McBride, et al., "Identification of a glycosylated *Ehrlichia canis* 19-kilodalton major immunoreative protein with a species-specific serine-rich glycopeptide epitope", Infect. Immuno. 2007; 75(1):74-82.

McBride, et al., "Molecular cloning of the gene for a conserved major immunoreactive 28-kilodalton protein of *Ehrlichia canis*: a potential serodiagnostic antigen", Clin. Diagn. Lab. Immunol. 1999; 6(3):392-9.

Ndip, et al., "Ehrlichial Infection in Cameroonian canines by *Ehrlichia canis* and *Ehrlichia ewingii*", Vet. Microbiol. 2005; 111(1-2):59-66.

Office action dated Oct. 15, 2009, for U.S. Appl. No. 11/397,222 (US 2006-0234322).

Gauither et al., "Western immunoblot analysis for distinguishing vaccination and infection status with *Borrelia burgdorferi* (Lyme disease) in dogs", J. Vet. Diagn. Invest., 11:259-265 (1999).

Office action dated Apr. 14, 2010 for U.S. Appl. No. 11/397,222.

* cited by examiner

HTWM / LYME / EC: SNAP 3 DX

ALUMINUM OXIDE

RIBI

2D GEL ANALYSIS OF ISOLATED *E. canis* - STAINED WITH BIOSAFE COOMASIE BLUE

WESTERN BLOT OF *E. Canis* PROTEINS RESOLVED USING 2D GELS PROBED WITH NORMAL CANINE PLASMA.

WESTERN ANALYSIS WITH VACCINATED SERA
POOL OF 4 VACCINATED DOGS - 1:100

WESTERN ANALYSIS WITH INFECTED SERA
POOL OF 3 POSITIVE DOGS - 1:100

Control dogs – naïve
(no previous exposure to antigens)

Vaccinated dogs – RIBI adjuvant

Vaccinated dogs – RIBI + BCG adjuvant

SEQUENCE LISTING

```
<160> NUMBER OF SEQ ID NOS: 33

<210> SEQ ID NO 1
<211> LENGTH: 2067
<212> TYPE: DNA
<213> ORGANISM: Ehrlichia canis

<400> SEQUENCE: 1

atggatattg ataacaataa tgtgactaca tcaagtacgc aagataaaag tgggaattta      60

atggaagtga ttatgcgtat attaaatttt ggtaataatt cagatgagaa agtaagcaat     120

gaagacacta aagttcttgt agagagttta caacctgctg tgaatgacaa tgtaggaaat     180

ccatcaagtg aagttggtaa agaagaaaat gctcctgaag ttaaagcgga agatttgcaa     240

cctgctgtag atggtagtgt agaacattca tcaagtgaag ttgggaaaaa agtatctgaa     300

actagtaaag aggaaagtac tcctgaagtt aaagcagaag atttgcaacc tgctgtagat     360

ggtagtatag aacattcatc aagtgaagtt ggagaaaaag tatctaaaac tagtaaagag     420

gaaagtactc ctgaagttaa agcagaagat ttgcaacctg ctgtagatga tagtgtggaa     480

cattcatcaa gtgaagttgg agaaaaagta tctgaaacta gtaaagagga aaatactcct     540

gaagttaaag cagaagattt gcaacctgct gtagatggta gtatagaaca ttcatcaagt     600

gaagttggag aaaaagtatc taaaactagt aaagaggaaa gtactcctga agttaaagca     660
```

-continued

```
gaagatttgc aacctgctgt agatgatagt gtggaacatt catcaagtga agttggagaa    720

aaagtatctg aaactagtaa agaggaaaat actcctgaag ttaaagcaga agatttgcaa    780

cctgctgtag atggtagtgt ggaacattca tcaagtgaag ttggagaaaa agtatctaaa    840

actagtaaag aggaaagtac tcctgaagtt aaagcagaag atttgcaacc tgctgtagat    900

gatagtgtgg aacattcatc aagtgaagtt ggagaaaaag tatctgaaac tagtaaagag    960

gaaaatactc ctgaagttag agcagaagat ttgcaacctg ctgtagatgg tagtgtagaa   1020

cattcatcaa gtgaagttgg agaaaaagta tctgaaacta gtaaagagga aagtactcct   1080

gaagttaaag cagaagattt gcaacctgct gtagatagta gtatagaaca ttcatcaagt   1140

gaagttggga aaaaagtatc tgaaactagt aaagaggaaa gtactcctga agttaaagca   1200

gaagatttgc aacctgctgt agatggtagt gtagaacatt catcaagtga agttggagaa   1260

aaagtatctg aaactagtaa agaggaaaat actcctgaag ttaaagcaga agatttgcaa   1320

cctgctgtag atggtagtgt agaacattca tcaagtgaag ttggagaaaa agtatctgaa   1380

actagtaaag aggaaaatac tcctgaagtt aaagcggaag atttgcaacc tgctgtagat   1440

ggtagtgtag aacattcatc aagtgaagtt ggagaaaaag tatctgaaac tagtaaagaa   1500

gaaagtactc ctgaagttaa agcagaagat ttgcaacctg ctgtagatga tagtgtagaa   1560

cattcatcaa gtgaagttgg agaaaaagta tctgaaacta gtaaagaaga aagtactcct   1620

gaagttaaag cggaagattt gcaacctgct gtagatggta gtgtggaaca ttcatcaagt   1680

gaagttggag aaaaagtatc tgagactagt aaagaggaaa gtactcctga agttaaagcg   1740

gaagtacagc ctgttgcaga tggtaatcct gttcctttaa atcctatgcc ttcaattgat   1800

aatattgata ctaatataat attccattac cataaagact gtaaaaaagg ttcagctgta   1860

ggaacagatg aaatgtgttg tcctgtatca gaattaatgg ctggggaaca tgttcatatg   1920

tatggaattt atgtctatag agttcaatca gtaaaggatt taagtggtgt atttaatata   1980

gatcattcta catgtgattg taatttagat gtttattttg taggatacaa ttcttttact   2040

aacaaagaaa cagttgattt aatataa                                        2067
```

<210> SEQ ID NO 2
<211> LENGTH: 688
<212> TYPE: PRT
<213> ORGANISM: Ehrlichia canis

<400> SEQUENCE: 2

```
Met Asp Ile Asp Asn Asn Asn Val Thr Thr Ser Ser Thr Gln Asp Lys
1               5                   10                  15

Ser Gly Asn Leu Met Glu Val Ile Met Arg Ile Leu Asn Phe Gly Asn
            20                  25                  30

Asn Ser Asp Glu Lys Val Ser Asn Glu Asp Thr Lys Val Leu Val Glu
        35                  40                  45

Ser Leu Gln Pro Ala Val Asn Asp Asn Val Gly Asn Pro Ser Ser Glu
    50                  55                  60

Val Gly Lys Glu Glu Asn Ala Pro Glu Val Lys Ala Glu Asp Leu Gln
65                  70                  75                  80

Pro Ala Val Asp Gly Ser Val Glu His Ser Ser Ser Glu Val Gly Lys
                85                  90                  95

Lys Val Ser Glu Thr Ser Lys Glu Glu Ser Thr Pro Glu Val Lys Ala
            100                 105                 110

Glu Asp Leu Gln Pro Ala Val Asp Gly Ser Ile Glu His Ser Ser Ser
        115                 120                 125
```

-continued

```
Glu Val Gly Glu Lys Val Ser Lys Thr Ser Lys Glu Glu Ser Thr Pro
    130                 135                 140

Glu Val Lys Ala Glu Asp Leu Gln Pro Ala Val Asp Asp Ser Val Glu
145                 150                 155                 160

His Ser Ser Ser Glu Val Gly Glu Lys Val Ser Glu Thr Ser Lys Glu
                165                 170                 175

Glu Asn Thr Pro Glu Val Lys Ala Glu Asp Leu Gln Pro Ala Val Asp
            180                 185                 190

Gly Ser Ile Glu His Ser Ser Ser Glu Val Gly Glu Lys Val Ser Lys
        195                 200                 205

Thr Ser Lys Glu Glu Ser Thr Pro Glu Val Lys Ala Glu Asp Leu Gln
    210                 215                 220

Pro Ala Val Asp Asp Ser Val Glu His Ser Ser Ser Glu Val Gly Glu
225                 230                 235                 240

Lys Val Ser Glu Thr Ser Lys Glu Glu Asn Thr Pro Glu Val Lys Ala
                245                 250                 255

Glu Asp Leu Gln Pro Ala Val Asp Gly Ser Val Glu His Ser Ser Ser
            260                 265                 270

Glu Val Gly Glu Lys Val Ser Lys Thr Ser Lys Glu Glu Ser Thr Pro
        275                 280                 285

Glu Val Lys Ala Glu Asp Leu Gln Pro Ala Val Asp Asp Ser Val Glu
    290                 295                 300

His Ser Ser Ser Glu Val Gly Glu Lys Val Ser Glu Thr Ser Lys Glu
305                 310                 315                 320

Glu Asn Thr Pro Glu Val Arg Ala Glu Asp Leu Gln Pro Ala Val Asp
                325                 330                 335

Gly Ser Val Glu His Ser Ser Ser Glu Val Gly Glu Lys Val Ser Glu
            340                 345                 350

Thr Ser Lys Glu Glu Ser Thr Pro Glu Val Lys Ala Glu Asp Leu Gln
        355                 360                 365

Pro Ala Val Asp Ser Ser Ile Glu His Ser Ser Ser Glu Val Gly Lys
    370                 375                 380

Lys Val Ser Glu Thr Ser Lys Glu Glu Ser Thr Pro Glu Val Lys Ala
385                 390                 395                 400

Glu Asp Leu Gln Pro Ala Val Asp Gly Ser Val Glu His Ser Ser Ser
                405                 410                 415

Glu Val Gly Glu Lys Val Ser Glu Thr Ser Lys Glu Glu Asn Thr Pro
            420                 425                 430

Glu Val Lys Ala Glu Asp Leu Gln Pro Ala Val Asp Gly Ser Val Glu
        435                 440                 445

His Ser Ser Ser Glu Val Gly Glu Lys Val Ser Glu Thr Ser Lys Glu
    450                 455                 460

Glu Asn Thr Pro Glu Val Lys Ala Glu Asp Leu Gln Pro Ala Val Asp
465                 470                 475                 480

Gly Ser Val Glu His Ser Ser Ser Glu Val Gly Glu Lys Val Ser Glu
                485                 490                 495

Thr Ser Lys Glu Glu Ser Thr Pro Glu Val Lys Ala Glu Asp Leu Gln
            500                 505                 510

Pro Ala Val Asp Asp Ser Val Glu His Ser Ser Ser Glu Val Gly Glu
        515                 520                 525

Lys Val Ser Glu Thr Ser Lys Glu Glu Ser Thr Pro Glu Val Lys Ala
    530                 535                 540
```

-continued

```
Glu Asp Leu Gln Pro Ala Val Asp Gly Ser Val Glu His Ser Ser Ser
545                 550                 555                 560

Glu Val Gly Glu Lys Val Ser Glu Thr Ser Lys Glu Glu Ser Thr Pro
                565                 570                 575

Glu Val Lys Ala Glu Val Gln Pro Val Ala Asp Gly Asn Pro Val Pro
            580                 585                 590

Leu Asn Pro Met Pro Ser Ile Asp Asn Ile Asp Thr Asn Ile Ile Phe
        595                 600                 605

His Tyr His Lys Asp Cys Lys Lys Gly Ser Ala Val Gly Thr Asp Glu
    610                 615                 620

Met Cys Cys Pro Val Ser Glu Leu Met Ala Gly Glu His Val His Met
625                 630                 635                 640

Tyr Gly Ile Tyr Val Tyr Arg Val Gln Ser Val Lys Asp Leu Ser Gly
                645                 650                 655

Val Phe Asn Ile Asp His Ser Thr Cys Asp Cys Asn Leu Asp Val Tyr
            660                 665                 670

Phe Val Gly Tyr Asn Ser Phe Thr Asn Lys Glu Thr Val Asp Leu Ile
        675                 680                 685


<210> SEQ ID NO 3
<211> LENGTH: 3186
<212> TYPE: DNA
<213> ORGANISM: Ehrlichia canis

<400> SEQUENCE: 3

aatttagatt ttggacttgt agatggagat ggtaaaaatc ctttacatca tgctgttgaa     60

catttgccac ctgttatact taagggcgta atggaccatg taaaaaatag tagtgagttt    120

caagatttag taaatgatcc tgattatttt ggaaatacta tagctcatta tgcagttaag    180

aataaaaatg ctgatttaac attgtttaac atgctgaaag cttcaggagc tgatttaaat    240

gttaggaatg tagttggtcg agctccaata catgttgctt cttctaatgg taaggctaat    300

gcagtttctg gacttgtatc atgtggtatt gacgttaatt ctcaagatgt gaatggagat    360

acaccacttc atattgctgt tgaaggcggt agtatggaga cggtattagc agtgttaaat    420

cagagaggtg ctgatgttag tgtccagaat aacgatggag ttacacctat gcttagtgct    480

gctaaatatg gagatatagg tgtaataaaa gctttaggtt cagctaaacc aaatattaaa    540

ggtgaagaca ctgttgctaa atcattgctg atggaggatt acaaaggttt tacacccttg    600

cattttgtag ctggtggtgg tagcagagat acattccgtg tcgtaagaaa aaattatgaa    660

aaatgtcatg acttagctac tattagggca gctttaatgc aagatagaag tggtggtgag    720

cttgtaaatt taggggattt tgaaagtgaa aatatattgg gttcgccaaa tgcaaaattc    780

ttgcagcata ttcaatcagc aaattttggt tttctccag cgcattgtgc tatagtatcg     840

tctaatcaca atgtaatgaa agatatctta aattttgttg ggattcgtt acacctacca     900

agtgagcgtg ggtataatgc aatgcaggtt gctgctttgt ttggtgacaa agaagcagtg    960

aaaatgcttg ctaaaagtgc taagccaagt gatcttaatt ttaagacttc agcaactcct   1020

actccgttaa atcttgcatg tcttagaggt gataatgagg tagtacgtgg gttagtaggt   1080

caacatggta ttgacattaa ccaacgtatg ggaagtgata aaaacactgt attgcattat   1140

gcaatcagca aaggagatag ttttcttgtg caaaagatat tagctcatac tggagttgat   1200

gttaattgtg agaataacct aggtcaaacg cctttacatt tagcagttga gggaggagat   1260

cctaagatag tatcttctct tcttaaagct ggtgcagtag ttaatcgtct ggatgataat   1320
```

-continued

```
ggtagatctg tactttcttc tgcgatagtt ccaggtagaa aagaaaaggg agtgctgggt   1380

atagttaata aattgctgga tagaggtgca gatattaatt tagatggaga ccacaatata   1440

ctttttgatc agtgtctaag ggtggatat aataatgtat tagataagtt aatacaacaa   1500

ggggttgaag ttaatcgaaa tagtgaaata cgtccaatgg tttatgctgc aatatctggt   1560

aatgagcatg ctatcaaatc attagctaat gctggtggag atgttaatga agtagtaaat   1620

aatccatcta gtaggcattc aggaaatcct ttaattatgg ttgcagtagc agatggtaat   1680

gcaggtcttc ttaaaacatt agtttctgaa ggatgtgatg ttggtaaatc tggaaaagat   1740

ggtaatacag cgttacatta tgctgttagt cattcagata aagagtttgg taataaagct   1800

ataaagatat taatttcacg taatagtgtt gggactaata gagatattct tactcaaaag   1860

aataacgcag gtgatacacc tttacatgaa gctcttaagt caggtaatat taattctgta   1920

cagaatatct taagtgctgt acatccaaga tacgcaaagg agatattaac agccagagac   1980

aaagaagggt acacaccaat gcattatact gttggagtaa ataatgttga tgttggtaga   2040

agtattctag agtctatgct ctctaaaggt gtgaataatc ttggagagat tgttggagca   2100

caggatagta attttcgaac acctctgcat gctgctatta aaatatctga ttatcgtgct   2160

gcggacatga taataggtag cttatcgaaa acagaattgt caaagttatc gcaattaaca   2220

gatattaacg ggatacacc actacatctt tcttgtcagt ctggtaatgt cgagatgaca   2280

caattctttc ttggaggttt ggataaacgt gaattaccta agacattaaa gatagcaaat   2340

aaaaatggag atactccttt acatgatgct ataagaaatg atgatattaa atctgcaaaa   2400

atgatgatta ggaattgtaa caaagaagaa cttgctaatg tattaaaatg taaagatagt   2460

tttggtaata cagtattgca tactattgct gaccaagtta ttgcgaatcc agaatcaaag   2520

aaagaccttg atggtttgat gaatttagca gtgaaaaggc taaagaatca agatctgaaa   2580

gatctagtta atacgcgaaa taactctgac gatactgttg cacattgtgc tcttttatcg   2640

gatatgaaat atgctcaaaa gatacttaaa tcatgtaacc atgatacatt agtgagagga   2700

aatagtaata atcaatcttt atcagagtgt attcgtgatg atagtaaata taaaaaaggt   2760

ggaattttta gtaagtcttt attttcaaaa ttaaagaaac ttgaggcacg agctgccagc   2820

gctagttatg aagaattatc tagtatcagt agtggtagtg atgtttcttc tgtatcaaca   2880

aatagcacag aagtaagtgc agtacctgaa gtggcaagaa gtagtggtgc tgtgtcgttc   2940

aaacatgtgc aagaaacagg agttgacacg tctggtcctt ctgatataga aagtttagag   3000

agattatctg atactagtct tgggtcaaat gattttgatc agcgaatggc agatttagat   3060

caagaaatag caaatattgt tagtggttta ccagaagtta cccaggtagc tgtaagtcaa   3120

caacaagcag catctcctag ttcaggtcaa gctgctggtg tgcaacaaaa agagatgcag   3180

agataa                                                              3186
```

<210> SEQ ID NO 4
<211> LENGTH: 1061
<212> TYPE: PRT
<213> ORGANISM: Ehrlichia canis

<400> SEQUENCE: 4

```
Asn Leu Asp Phe Gly Leu Val Asp Gly Asp Gly Lys Asn Pro Leu His
1               5                   10                  15

His Ala Val Glu His Leu Pro Pro Val Ile Leu Lys Gly Val Met Asp
            20                  25                  30

His Val Lys Asn Ser Ser Glu Phe Gln Asp Leu Val Asn Asp Pro Asp
```

-continued

```
        35                  40                  45

Tyr Phe Gly Asn Thr Ile Ala His Tyr Ala Val Lys Asn Lys Asn Ala
    50                  55                  60

Asp Leu Thr Leu Phe Asn Met Leu Lys Ala Ser Gly Ala Asp Leu Asn
65                  70                  75                  80

Val Arg Asn Val Val Gly Arg Ala Pro Ile His Val Ala Ser Ser Asn
                85                  90                  95

Gly Lys Ala Asn Ala Val Ser Gly Leu Val Ser Cys Gly Ile Asp Val
            100                 105                 110

Asn Ser Gln Asp Val Asn Gly Asp Thr Pro Leu His Ile Ala Val Glu
        115                 120                 125

Gly Gly Ser Met Glu Thr Val Leu Ala Val Leu Asn Gln Arg Gly Ala
    130                 135                 140

Asp Val Ser Val Gln Asn Asn Asp Gly Val Thr Pro Met Leu Ser Ala
145                 150                 155                 160

Ala Lys Tyr Gly Asp Ile Gly Val Ile Lys Ala Leu Gly Ser Ala Lys
                165                 170                 175

Pro Asn Ile Lys Gly Glu Asp Thr Val Ala Lys Ser Leu Leu Met Glu
            180                 185                 190

Asp Tyr Lys Gly Phe Thr Pro Leu His Phe Val Ala Gly Gly Gly Ser
        195                 200                 205

Arg Asp Thr Phe Arg Val Val Arg Lys Asn Tyr Glu Lys Cys His Asp
    210                 215                 220

Leu Ala Thr Ile Arg Ala Ala Leu Met Gln Asp Arg Ser Gly Gly Glu
225                 230                 235                 240

Leu Val Asn Leu Gly Asp Phe Glu Ser Glu Asn Ile Leu Gly Ser Pro
                245                 250                 255

Asn Ala Lys Phe Leu Gln His Ile Gln Ser Ala Asn Phe Gly Phe Ser
            260                 265                 270

Pro Ala His Cys Ala Ile Val Ser Ser Asn His Asn Val Met Lys Asp
        275                 280                 285

Ile Leu Asn Phe Val Gly Asp Ser Leu His Leu Pro Ser Glu Arg Gly
    290                 295                 300

Tyr Asn Ala Met Gln Val Ala Ala Leu Phe Gly Asp Lys Glu Ala Val
305                 310                 315                 320

Lys Met Leu Ala Lys Ser Ala Lys Pro Ser Asp Leu Asn Phe Lys Thr
                325                 330                 335

Ser Ala Thr Pro Thr Pro Leu Asn Leu Ala Cys Leu Arg Gly Asp Asn
            340                 345                 350

Glu Val Val Arg Gly Leu Val Gly Gln His Gly Ile Asp Ile Asn Gln
        355                 360                 365

Arg Met Gly Ser Asp Lys Asn Thr Val Leu His Tyr Ala Ile Ser Lys
    370                 375                 380

Gly Asp Ser Phe Leu Val Gln Lys Ile Leu Ala His Thr Gly Val Asp
385                 390                 395                 400

Val Asn Cys Glu Asn Asn Leu Gly Gln Thr Pro Leu His Leu Ala Val
                405                 410                 415

Glu Gly Gly Asp Pro Lys Ile Val Ser Ser Leu Leu Lys Ala Gly Ala
            420                 425                 430

Val Val Asn Arg Leu Asp Asp Asn Gly Arg Ser Val Leu Ser Ser Ala
        435                 440                 445

Ile Val Pro Gly Arg Lys Glu Lys Gly Val Leu Gly Ile Val Asn Lys
    450                 455                 460
```

-continued

```
Leu Leu Asp Arg Gly Ala Asp Ile Asn Leu Asp Gly Asp His Asn Ile
465                 470                 475                 480

Leu Phe Asp Gln Cys Leu Arg Gly Gly Tyr Asn Asn Val Leu Asp Lys
                485                 490                 495

Leu Ile Gln Gln Gly Val Glu Val Asn Arg Asn Ser Glu Ile Arg Pro
            500                 505                 510

Met Val Tyr Ala Ala Ile Ser Gly Asn Glu His Ala Ile Lys Ser Leu
        515                 520                 525

Ala Asn Ala Gly Gly Asp Val Asn Glu Val Val Asn Asn Pro Ser Ser
    530                 535                 540

Arg His Ser Gly Asn Pro Leu Ile Met Val Ala Val Ala Asp Gly Asn
545                 550                 555                 560

Ala Gly Leu Leu Lys Thr Leu Val Ser Glu Gly Cys Asp Val Gly Lys
                565                 570                 575

Ser Gly Lys Asp Gly Asn Thr Ala Leu His Tyr Ala Val Ser His Ser
            580                 585                 590

Asp Lys Glu Phe Gly Asn Lys Ala Ile Lys Ile Leu Ile Ser Arg Asn
        595                 600                 605

Ser Val Gly Thr Asn Arg Asp Ile Leu Thr Gln Lys Asn Asn Ala Gly
    610                 615                 620

Asp Thr Pro Leu His Glu Ala Leu Lys Ser Gly Asn Ile Asn Ser Val
625                 630                 635                 640

Gln Asn Ile Leu Ser Ala Val His Pro Arg Tyr Ala Lys Glu Ile Leu
                645                 650                 655

Thr Ala Arg Asp Lys Glu Gly Tyr Thr Pro Met His Tyr Thr Val Gly
            660                 665                 670

Val Asn Asn Val Asp Val Gly Arg Ser Ile Leu Glu Ser Met Leu Ser
        675                 680                 685

Lys Gly Val Asn Asn Leu Gly Glu Ile Val Gly Ala Gln Asp Ser Asn
    690                 695                 700

Phe Arg Thr Pro Leu His Ala Ala Ile Lys Ile Ser Asp Tyr Arg Ala
705                 710                 715                 720

Ala Asp Met Ile Ile Gly Ser Leu Ser Lys Thr Glu Leu Ser Lys Leu
                725                 730                 735

Ser Gln Leu Thr Asp Ile Asn Gly Asp Thr Pro Leu His Leu Ser Cys
            740                 745                 750

Gln Ser Gly Asn Val Glu Met Thr Gln Phe Phe Leu Gly Gly Leu Asp
        755                 760                 765

Lys Arg Glu Leu Pro Lys Thr Leu Lys Ile Ala Asn Lys Asn Gly Asp
    770                 775                 780

Thr Pro Leu His Asp Ala Ile Arg Asn Asp Asp Ile Lys Ser Ala Lys
785                 790                 795                 800

Met Met Ile Arg Asn Cys Asn Lys Glu Glu Leu Ala Asn Val Leu Lys
                805                 810                 815

Cys Lys Asp Ser Phe Gly Asn Thr Val Leu His Thr Ile Ala Asp Gln
            820                 825                 830

Val Ile Ala Asn Pro Glu Ser Lys Lys Asp Leu Asp Gly Leu Met Asn
        835                 840                 845

Leu Ala Val Lys Arg Leu Lys Asn Gln Asp Leu Lys Asp Leu Val Asn
    850                 855                 860

Thr Arg Asn Asn Ser Asp Asp Thr Val Ala His Cys Ala Leu Leu Ser
865                 870                 875                 880
```

-continued

```
Asp Met Lys Tyr Ala Gln Lys Ile Leu Lys Ser Cys Asn His Asp Thr
                885                 890                 895

Leu Val Arg Gly Asn Ser Asn Asn Gln Ser Leu Ser Glu Cys Ile Arg
            900                 905                 910

Asp Asp Ser Lys Tyr Lys Lys Gly Gly Ile Phe Ser Lys Ser Leu Phe
        915                 920                 925

Ser Lys Leu Lys Lys Leu Glu Ala Arg Ala Ala Ser Ala Ser Tyr Glu
    930                 935                 940

Glu Leu Ser Ser Ile Ser Ser Gly Ser Asp Val Ser Ser Val Ser Thr
945                 950                 955                 960

Asn Ser Thr Glu Val Ser Ala Val Pro Glu Val Ala Arg Ser Ser Gly
                965                 970                 975

Ala Val Ser Phe Lys His Val Gln Glu Thr Gly Val Asp Thr Ser Gly
            980                 985                 990

Pro Ser Asp Ile Glu Ser Leu Glu  Arg Leu Ser Asp Thr  Ser Leu Gly
        995                 1000                1005

Ser Asn  Asp Phe Asp Gln Arg  Met Ala Asp Leu Asp  Gln Glu Ile
    1010                1015                1020

Ala Asn  Ile Val Ser Gly Leu  Pro Glu Val Thr Gln  Val Ala Val
    1025                1030                1035

Ser Gln  Gln Gln Ala Ala Ser  Pro Ser Ser Gly Gln  Ala Ala Gly
    1040                1045                1050

Val Gln  Gln Lys Glu Met Gln  Arg
    1055                1060
```

<210> SEQ ID NO 5
<211> LENGTH: 2373
<212> TYPE: DNA
<213> ORGANISM: Ehrlichia canis

<400> SEQUENCE: 5

```
aattatgctg aaactacttt atcatttggt gaatctcgag cagaaggacg tgaatctcca     60

tcaagtgcat ttgttcaaac tggtcaatca gaagtacctc ggagtgaggc tgcagagcca    120

ttaattcaat ttcctcatga tgaagaaagt actgcattag gttctcaagc aactatgaca    180

ggagtgtcta ctcaggctag tccgtcagca gcatatcagg atgatagtga aatatcacgt    240

atgaggtcta tggcaggaac atctgctcaa gctgatcaat cagcagtaca tcgtcggagt    300

ggtacagcat tagagccatt aattgaattg cctgatgaag aagaaaatgc tgcattagat    360

tttcaaacag ctatgacagg agtgcctact caggctagtc cgtcagcagt acatcggagt    420

ggtgttgcat cagatcctac gctacctgat gatgaaagaa ttgatgttcc atcagtttca    480

tctcaagttg taagaccttt tagtgatggt gaagattatt cagtatatga taaatcaggt    540

gtagtaagtg gtcatgaaag acctgtttct tctagagatt caagacaatt ggatgcattt    600

ggtgatccat cagatgattt attgccggag agtgaaatta ttgttagcag cagtaagaaa    660

gcaatattag atagccaaaa tgaaatagaa tctcttattc agagtggaga tacttctaga    720

tgtattaggg caattaatag tgctcctagt gcgtcagtgt ttcaactgaa gactttatcg    780

aatgatatat ctattgctgg acgtgctttt ttaaatggta atattgattt aatagaagct    840

tgtatgaatt ctggcaagaa attaaatcca aatattactg ataatgaaaa aaatactcta    900

ttacatcaat ttgtaggata ttttgaacgc gatccgagaa tgttgcttga tgcaggaatg    960

cgtaatctgt tttgagatt atgcatggat tatggtttcg atattaatca taaaaatagt   1020

aatggtaata cagtacttga tagattaaat gatttagtag aagggttaag tagttcgcaa   1080
```

```
gttgatcttg aaagtagtgg tattgatgag tttatgatct cattgttagc tcattctaga   1140
atgagtgatc aagcagtaaa gaatattgct actgcgcaaa atgagttttt tgcacgtgat   1200
tctgtttata atattagtcg tttagttgat acttctatag ttttgcagaa taaattcagt   1260
gaagtatttt atgaagtctg tggacgtatt ttatctgaag aagctggtaa acataagggt   1320
gttgctgaag caaattattc aagattgaat aaaatattaa atgatgaatg tcttagaaag   1380
actttagcta atacagatgc cgatggaaat aatgttttac agagattgtg tcaagatatt   1440
gcttctggaa aaatcaatgc tcgtgatgac agagtattaa aactttttga gacaattata   1500
tctaatttaa aagacaaaga taaagcatta ctagaggatt tattatttaa taatagaaac   1560
tcaagatttg aaaattgcat tgaagctata ccacgtattc ctggtgccga tgctctattt   1620
aaaaaactag aagagttatt attaaaaaag aaaatagcag agtcttgtga ttttaattct   1680
atgttagtga attgtgctga gtctgctaat gataatttat ataattacct gcgcactaat   1740
tatgcagtta ttggtataaa taacgtagat ataaatggca attcatccct atgtaaagct   1800
gttgttactg ggtcacaagg tattgttaaa gcagtattat caactggaac taatattaat   1860
aggaaagata aaaatggtaa tacaccttta catgcattgt taatttttat gatgtctaac   1920
cctgaacttg tcaaggagca acatatttca cttgtgaaat tcttagcgtc tcgtggagct   1980
ttacttaatg taaaaaataa tatgaatatt tctccaatta tgcttgcaga atctattgat   2040
aagaaagagg aacttgctaa gaaatttaca aatcaaaaag ttagtatttt agaatcttta   2100
atagctggta gtgaagaaca tttagggctt aaatccaaat gtatatctga gttaaagcct   2160
tatatagaat taggaaaagg catgaagtac gaagatatac atgctgatgt aataggtggt   2220
gtattatctg ctgatatgtg taatgctaga ttgcagatag gtaaattatt aaatggtgat   2280
ttttgtaaag aaaatgaatt aaagacagta aaatttaatt tttctgatac aaataagggt   2340
tatgtacaaa atgttggtaa aaaaagaaat tat                                 2373
```

<210> SEQ ID NO 6
<211> LENGTH: 791
<212> TYPE: PRT
<213> ORGANISM: Ehrlichia canis

<400> SEQUENCE: 6

```
Asn Tyr Ala Glu Thr Thr Leu Ser Phe Gly Glu Ser Arg Ala Glu Gly
1               5                   10                  15

Arg Glu Ser Pro Ser Ser Ala Phe Val Gln Thr Gly Gln Ser Glu Val
            20                  25                  30

Pro Arg Ser Glu Ala Ala Glu Pro Leu Ile Gln Phe Pro His Asp Glu
        35                  40                  45

Glu Ser Thr Ala Leu Gly Ser Gln Ala Thr Met Thr Gly Val Ser Thr
    50                  55                  60

Gln Ala Ser Pro Ser Ala Ala Tyr Gln Asp Asp Ser Glu Ile Ser Arg
65                  70                  75                  80

Met Arg Ser Met Ala Gly Thr Ser Ala Gln Ala Asp Gln Ser Ala Val
                85                  90                  95

His Arg Arg Ser Gly Thr Ala Leu Glu Pro Leu Ile Glu Leu Pro Asp
            100                 105                 110

Glu Glu Glu Asn Ala Ala Leu Asp Phe Gln Thr Ala Met Thr Gly Val
        115                 120                 125

Pro Thr Gln Ala Ser Pro Ser Ala Val His Arg Ser Gly Val Ala Ser
    130                 135                 140
```

-continued

```
Asp Pro Thr Leu Pro Asp Asp Glu Arg Ile Asp Val Pro Ser Val Ser
145                 150                 155                 160

Ser Gln Val Val Arg Pro Phe Ser Asp Gly Glu Asp Tyr Ser Val Tyr
                165                 170                 175

Asp Lys Ser Gly Val Val Ser Gly His Glu Arg Pro Val Ser Ser Arg
            180                 185                 190

Asp Ser Arg Gln Leu Asp Ala Phe Gly Asp Pro Ser Asp Asp Leu Leu
        195                 200                 205

Pro Glu Ser Glu Ile Ile Val Ser Ser Ser Lys Lys Ala Ile Leu Asp
    210                 215                 220

Ser Gln Asn Glu Ile Glu Ser Leu Ile Gln Ser Gly Asp Thr Ser Arg
225                 230                 235                 240

Cys Ile Arg Ala Ile Asn Ser Ala Pro Ser Ala Ser Val Phe Gln Leu
                245                 250                 255

Lys Thr Leu Ser Asn Asp Ile Ser Ile Ala Gly Arg Ala Phe Leu Asn
            260                 265                 270

Gly Asn Ile Asp Leu Ile Glu Ala Cys Met Asn Ser Gly Lys Lys Leu
        275                 280                 285

Asn Pro Asn Ile Thr Asp Asn Glu Lys Asn Thr Leu Leu His Gln Phe
    290                 295                 300

Val Gly Tyr Phe Glu Arg Asp Pro Arg Met Leu Leu Asp Ala Gly Met
305                 310                 315                 320

Arg Asn Leu Phe Leu Arg Leu Cys Met Asp Tyr Gly Phe Asp Ile Asn
                325                 330                 335

His Lys Asn Ser Asn Gly Asn Thr Val Leu Asp Arg Leu Asn Asp Leu
            340                 345                 350

Val Glu Gly Leu Ser Ser Ser Gln Val Asp Leu Glu Ser Ser Gly Ile
        355                 360                 365

Asp Glu Phe Met Ile Ser Leu Leu Ala His Ser Arg Met Ser Asp Gln
    370                 375                 380

Ala Val Lys Asn Ile Ala Thr Ala Gln Asn Glu Phe Phe Ala Arg Asp
385                 390                 395                 400

Ser Val Tyr Asn Ile Ser Arg Leu Val Asp Thr Ser Ile Val Leu Gln
                405                 410                 415

Asn Lys Phe Ser Glu Val Phe Tyr Glu Val Cys Gly Arg Ile Leu Ser
            420                 425                 430

Glu Glu Ala Gly Lys His Lys Gly Val Ala Glu Ala Asn Tyr Ser Arg
        435                 440                 445

Leu Asn Lys Ile Leu Asn Asp Glu Cys Leu Arg Lys Thr Leu Ala Asn
    450                 455                 460

Thr Asp Ala Asp Gly Asn Asn Val Leu Gln Arg Leu Cys Gln Asp Ile
465                 470                 475                 480

Ala Ser Gly Lys Ile Asn Ala Arg Asp Asp Arg Val Leu Lys Leu Phe
                485                 490                 495

Glu Thr Ile Ile Ser Asn Leu Lys Asp Lys Asp Lys Ala Leu Leu Glu
            500                 505                 510

Asp Leu Leu Phe Asn Asn Arg Asn Ser Arg Phe Glu Asn Cys Ile Glu
        515                 520                 525

Ala Ile Pro Arg Ile Pro Gly Ala Asp Ala Leu Phe Lys Lys Leu Glu
    530                 535                 540

Glu Leu Leu Leu Lys Lys Lys Ile Ala Glu Ser Cys Asp Phe Asn Ser
545                 550                 555                 560
```

-continued

```
Met Leu Val Asn Cys Ala Glu Ser Ala Asn Asp Asn Leu Tyr Asn Tyr
                565                 570                 575

Leu Arg Thr Asn Tyr Ala Val Ile Gly Ile Asn Asn Val Asp Ile Asn
            580                 585                 590

Gly Asn Ser Ser Leu Cys Lys Ala Val Val Thr Gly Ser Gln Gly Ile
        595                 600                 605

Val Lys Ala Val Leu Ser Thr Gly Thr Asn Ile Asn Arg Lys Asp Lys
    610                 615                 620

Asn Gly Asn Thr Pro Leu His Ala Leu Leu Ile Phe Met Met Ser Asn
625                 630                 635                 640

Pro Glu Leu Val Lys Glu Gln His Ile Ser Leu Val Lys Phe Leu Ala
                645                 650                 655

Ser Arg Gly Ala Leu Leu Asn Val Lys Asn Asn Met Asn Ile Ser Pro
            660                 665                 670

Ile Met Leu Ala Glu Ser Ile Asp Lys Lys Glu Glu Leu Ala Lys Lys
        675                 680                 685

Phe Thr Asn Gln Lys Val Ser Ile Leu Glu Ser Leu Ile Ala Gly Ser
    690                 695                 700

Glu Glu His Leu Gly Leu Lys Ser Lys Cys Ile Ser Glu Leu Lys Pro
705                 710                 715                 720

Tyr Ile Glu Leu Gly Lys Gly Met Lys Tyr Glu Asp Ile His Ala Asp
                725                 730                 735

Val Ile Gly Gly Val Leu Ser Ala Asp Met Cys Asn Ala Arg Leu Gln
            740                 745                 750

Ile Gly Lys Leu Leu Asn Gly Asp Phe Cys Lys Glu Asn Glu Leu Lys
        755                 760                 765

Thr Val Lys Phe Asn Phe Ser Asp Thr Asn Lys Gly Tyr Val Gln Asn
    770                 775                 780

Val Gly Lys Lys Arg Asn Tyr
785                 790
```

<210> SEQ ID NO 7
<211> LENGTH: 2283
<212> TYPE: DNA
<213> ORGANISM: Ehrlichia canis

<400> SEQUENCE: 7

```
gtaaaaaaat taagattatt attaaattca ataagtgagt taccgcaaga attaaaagat      60

caaattttaa gtactagaag tactatagat aaattacgaa atagaattaa tgcctgcata     120

aagtctgacg atagagaagg tattgcacat gctgtagaat ctatggctag ttcttattgt     180

gaattattag gacattgtag attaattttt aagaaattat atgatgaaaa tgctgataaa     240

agtttgctag aattatgtat taaagaatat caatctgatt taaacaaatt attggaacaa     300

ggtattgata tatgtgcttc agaagtctca tcagaatgta aggatttagt ttgtaaagta     360

tgtgaagatg aatttgagaa atatgactct ttatctaaag tacaaagatt cagggaatta     420

tctggtgaaa ttgctgattt ggatgataaa ttaacaagaa gggcttcttt tgttgagact     480

tttggattat ttagcagtag attaagacat tatagggaaa ttttaggaga tggtgattta     540

aaatttcgag agaggatagt tgaaaaatat caagaggatt taaaggaatt attagaatta     600

tctgttgatc ttcatttgtt aataaattta ccagcattag aagatttacg cgatcataga     660

aatttagtgc atagagcatg taatgctgaa attgaaaaat atctaacttt atttgatgat     720

caacaattac gtacattatc gcaagaagtg aataatgctc atggtgaatt gatacagatg     780
```

```
ttttctaagt ttagtatatt tgttgatggc gttactggta ttgaacagag cacatctcaa    840

gtagagcacc ctcgttctga tattgctaaa agagatacta caacaccaaa gcaacgtgtt    900

gtgcaaggta aagatgatat acaatctagt gatagtgata gtgatagtga tagtaaatac    960

ggtgatgatg atagtaaaaa agcatcagtt agtgcacctg ctgttgacca agttgtacct   1020

gtagctgatg ttcaacctga acctcagcta ggtgaaggat tggaaacatt agagtctagt   1080

atagctgaag gacctgagtt gcctggtgat gcatctactg ctaagcaatc tatacctttt   1140

gcgataacac catcaagtcc tgagacagtt gatgaaaaac ttgaaagttc tggtgttagt   1200

caagatggta ttacaacacc aggacaacgt gttgtgcaag gtaaagatga tatacaatct   1260

agtgatagtg atagtgatag taaatacggt gatgatgata gtaaaaaagc atcagctagt   1320

gcacctgctg ttgaccaagt tgtacctgta gctgatgttc aacctgaacc tcagctaggt   1380

gaaaaattgg aaacattaga gtctagtata actaaaggac ctgagttgcc tggtgatgca   1440

tctactgcta agcaatctat accttttgcg ataacaccat caagtcctga gacagttgat   1500

gaaaaacttg aaagttctgg tgttagtcaa gatggtatta caacaccagg acaacgtgtt   1560

gtgcaaggta aagatgatat acaatctagt gatagtgata gtgatagtaa atacggtgat   1620

gatgatagta aaaaagcatc agctagtgca cctgctgttg accaagttgt accttctgac   1680

actcgtgcag atggagtatc agaaccatta gcatctcatg tggatcaagg atctgatgta   1740

cctggtgatg catctgttga tggtgttgat ttaagattag gacggttatc tactgagcaa   1800

agtggattgt tgccacgtca tgaacaaaat gtaagagcat ttattttaga acagagtttg   1860

ttagatcaat tatatatgga ctatatagat ttacaccctg atcagaaaag ttgtgaagct   1920

tataattcag cattgcatgg atataataca agattagagt tacagaagga atataacagg   1980

atttttgaat cacatgaatc agcatctcca aatgaaatta atagtttttc acaaaaatat   2040

agagcagcat taagagatgt tgcgcaggat attgttaatc agggtccaat gttttattct   2100

tctagagatg caatgctatt aagggctaga gtagacacat tgtgtgatat gtgtcgttca   2160

atacgtaatc tgtatatggt tgaattagat gccatagata aagaagaaaa atcgttacaa   2220

tctgatatga aatctgcaag ttctagtgat aaaaagttga tacaagaaaa aataaaatta   2280

ctt                                                                 2283
```

```
<210> SEQ ID NO 8
<211> LENGTH: 761
<212> TYPE: PRT
<213> ORGANISM: Ehrlichia canis

<400> SEQUENCE: 8

Val Lys Lys Leu Arg Leu Leu Leu Asn Ser Ile Ser Glu Leu Pro Gln
1               5                   10                  15

Glu Leu Lys Asp Gln Ile Leu Ser Thr Arg Ser Thr Ile Asp Lys Leu
            20                  25                  30

Arg Asn Arg Ile Asn Ala Cys Ile Lys Ser Asp Asp Arg Glu Gly Ile
        35                  40                  45

Ala His Ala Val Glu Ser Met Ala Ser Ser Tyr Cys Glu Leu Leu Gly
    50                  55                  60

His Cys Arg Leu Ile Phe Lys Lys Leu Tyr Asp Glu Asn Ala Asp Lys
65                  70                  75                  80

Ser Leu Leu Glu Leu Cys Ile Lys Glu Tyr Gln Ser Asp Leu Asn Lys
                85                  90                  95

Leu Leu Glu Gln Gly Ile Asp Ile Cys Ala Ser Glu Val Ser Ser Glu
```

-continued

```
            100                 105                 110

Cys Lys Asp Leu Val Cys Lys Val Cys Glu Asp Glu Phe Glu Lys Tyr
        115                 120                 125

Asp Ser Leu Ser Lys Val Gln Arg Phe Arg Glu Leu Ser Gly Glu Ile
    130                 135                 140

Ala Asp Leu Asp Asp Lys Leu Thr Arg Arg Ala Ser Phe Val Glu Thr
145                 150                 155                 160

Phe Gly Leu Phe Ser Ser Arg Leu Arg His Tyr Arg Glu Ile Leu Gly
                165                 170                 175

Asp Gly Asp Leu Lys Phe Arg Glu Arg Ile Val Glu Lys Tyr Gln Glu
            180                 185                 190

Asp Leu Lys Glu Leu Leu Glu Leu Ser Val Asp Leu His Leu Leu Ile
        195                 200                 205

Asn Leu Pro Ala Leu Glu Asp Leu Arg Asp His Arg Asn Leu Val His
    210                 215                 220

Arg Ala Cys Asn Ala Glu Ile Glu Lys Tyr Leu Thr Leu Phe Asp Asp
225                 230                 235                 240

Gln Gln Leu Arg Thr Leu Ser Gln Glu Val Asn Asn Ala His Gly Glu
                245                 250                 255

Leu Ile Gln Met Phe Ser Lys Phe Ser Ile Phe Val Asp Gly Val Thr
            260                 265                 270

Gly Ile Glu Gln Ser Thr Ser Gln Val Glu His Pro Arg Ser Asp Ile
        275                 280                 285

Ala Lys Arg Asp Thr Thr Thr Pro Lys Gln Arg Val Val Gln Gly Lys
    290                 295                 300

Asp Asp Ile Gln Ser Ser Asp Ser Asp Ser Asp Ser Asp Ser Lys Tyr
305                 310                 315                 320

Gly Asp Asp Asp Ser Lys Lys Ala Ser Val Ser Ala Pro Ala Val Asp
                325                 330                 335

Gln Val Val Pro Val Ala Asp Val Gln Pro Glu Pro Gln Leu Gly Glu
            340                 345                 350

Gly Leu Glu Thr Leu Glu Ser Ser Ile Ala Glu Gly Pro Glu Leu Pro
        355                 360                 365

Gly Asp Ala Ser Thr Ala Lys Gln Ser Ile Pro Phe Ala Ile Thr Pro
    370                 375                 380

Ser Ser Pro Glu Thr Val Asp Glu Lys Leu Glu Ser Ser Gly Val Ser
385                 390                 395                 400

Gln Asp Gly Ile Thr Thr Pro Gly Gln Arg Val Val Gln Gly Lys Asp
                405                 410                 415

Asp Ile Gln Ser Ser Asp Ser Asp Ser Asp Ser Lys Tyr Gly Asp Asp
            420                 425                 430

Asp Ser Lys Lys Ala Ser Ala Ser Ala Pro Ala Val Asp Gln Val Val
        435                 440                 445

Pro Val Ala Asp Val Gln Pro Glu Pro Gln Leu Gly Glu Lys Leu Glu
    450                 455                 460

Thr Leu Glu Ser Ser Ile Thr Lys Gly Pro Glu Leu Pro Gly Asp Ala
465                 470                 475                 480

Ser Thr Ala Lys Gln Ser Ile Pro Phe Ala Ile Thr Pro Ser Ser Pro
                485                 490                 495

Glu Thr Val Asp Glu Lys Leu Glu Ser Ser Gly Val Ser Gln Asp Gly
            500                 505                 510

Ile Thr Thr Pro Gly Gln Arg Val Val Gln Gly Lys Asp Asp Ile Gln
        515                 520                 525
```

```
Ser Ser Asp Ser Asp Ser Asp Ser Lys Tyr Gly Asp Asp Asp Ser Lys
    530                 535                 540

Lys Ala Ser Ala Ser Ala Pro Ala Val Asp Gln Val Val Pro Ser Asp
545                 550                 555                 560

Thr Arg Ala Asp Gly Val Ser Glu Pro Leu Ala Ser His Val Asp Gln
                565                 570                 575

Gly Ser Asp Val Pro Gly Asp Ala Ser Val Asp Gly Val Asp Leu Arg
            580                 585                 590

Leu Gly Arg Leu Ser Thr Glu Gln Ser Gly Leu Leu Pro Arg His Glu
        595                 600                 605

Gln Asn Val Arg Ala Phe Ile Leu Glu Gln Ser Leu Leu Asp Gln Leu
    610                 615                 620

Tyr Met Asp Tyr Ile Asp Leu His Pro Asp Gln Lys Ser Cys Glu Ala
625                 630                 635                 640

Tyr Asn Ser Ala Leu His Gly Tyr Asn Thr Arg Leu Glu Leu Gln Lys
                645                 650                 655

Glu Tyr Asn Arg Ile Phe Glu Ser His Glu Ser Ala Ser Pro Asn Glu
            660                 665                 670

Ile Asn Ser Phe Ser Gln Lys Tyr Arg Ala Ala Leu Arg Asp Val Ala
        675                 680                 685

Gln Asp Ile Val Asn Gln Gly Pro Met Phe Tyr Ser Ser Arg Asp Ala
    690                 695                 700

Met Leu Leu Arg Ala Arg Val Asp Thr Leu Cys Asp Met Cys Arg Ser
705                 710                 715                 720

Ile Arg Asn Leu Tyr Met Val Glu Leu Asp Ala Ile Asp Lys Glu Glu
                725                 730                 735

Lys Ser Leu Gln Ser Asp Met Lys Ser Ala Ser Ser Ser Asp Lys Lys
            740                 745                 750

Leu Ile Gln Glu Lys Ile Lys Leu Leu
        755                 760


<210> SEQ ID NO 9
<211> LENGTH: 414
<212> TYPE: PRT
<213> ORGANISM: Ehrlichia canis

<400> SEQUENCE: 9

Ala Thr Gly Thr Thr Ala Cys Ala Cys Gly Thr Thr Cys Ala Ala Ala
1               5                   10                  15

Ala Thr Cys Ala Thr Gly Thr Thr Gly Ala Thr Cys Ala Ala Cys Ala
            20                  25                  30

Thr Ala Cys Ala Ala Ala Thr Cys Ala Thr Ala Thr Ala Gly Ala Ala
        35                  40                  45

Cys Ala Thr Gly Ala Thr Gly Ala Thr Thr Ala Cys Cys Ala Thr Thr
    50                  55                  60

Thr Thr Ala Cys Thr Gly Gly Thr Cys Cys Thr Ala Cys Thr Ala Gly
65                  70                  75                  80

Thr Thr Thr Thr Gly Ala Ala Gly Thr Thr Ala Ala Thr Cys Thr Thr
                85                  90                  95

Thr Cys Thr Gly Ala Ala Gly Ala Ala Gly Ala Ala Ala Ala Ala Ala
            100                 105                 110

Thr Gly Gly Ala Gly Thr Thr Ala Cys Ala Ala Gly Ala Ala Gly Thr
        115                 120                 125

Ala Thr Cys Thr Thr Cys Thr Ala Thr Thr Gly Ala Thr Ala Gly Thr
```

-continued

```
    130                 135                 140

Gly Thr Ala Gly Gly Ala Thr Gly Cys Gly Ala Ala Gly Ala Thr Thr
145                 150                 155                 160

Gly Thr Gly Ala Thr Cys Cys Ala Ala Ala Thr Thr Gly Thr Cys Gly
                165                 170                 175

Thr Thr Ala Thr Cys Cys Thr Thr Thr Ala Gly Ala Ala Thr Thr Ala
            180                 185                 190

Gly Thr Ala Gly Ala Ala Thr Gly Thr Cys Ala Gly Cys Gly Thr Ala
        195                 200                 205

Thr Thr Gly Ala Gly Gly Ala Ala Ala Gly Ala Cys Cys Ala Gly Thr
    210                 215                 220

Ala Thr Gly Cys Ala Ala Thr Gly Cys Ala Gly Gly Thr Thr Thr Ala
225                 230                 235                 240

Gly Ala Gly Ala Gly Cys Thr Thr Gly Ala Cys Thr Gly Thr Thr Gly
                245                 250                 255

Ala Thr Gly Cys Ala Thr Ala Thr Cys Ala Ala Thr Thr Ala Gly Gly
            260                 265                 270

Ala Thr Thr Gly Thr Thr Gly Thr Thr Ala Gly Gly Thr Gly Gly Thr
        275                 280                 285

Thr Thr Thr Thr Thr Ala Ala Gly Thr Gly Cys Thr Ala Thr Gly Ala
    290                 295                 300

Ala Thr Thr Ala Cys Ala Thr Ala Thr Cys Thr Thr Ala Thr Ala Gly
305                 310                 315                 320

Cys Thr Ala Thr Cys Cys Thr Thr Gly Thr Thr Ala Thr Thr Ala Thr
                325                 330                 335

Thr Ala Thr Gly Ala Thr Thr Gly Thr Thr Gly Thr Gly Ala Thr Ala
            340                 345                 350

Gly Ala Ala Ala Thr Thr Ala Thr Thr Ala Cys Gly Ala Cys Thr Gly
        355                 360                 365

Thr Thr Gly Thr Cys Ala Thr Ala Ala Gly Ala Ala Thr Gly Cys Gly
    370                 375                 380

Thr Gly Thr Thr Ala Thr Thr Ala Cys Ala Ala Cys Thr Gly Thr Thr
385                 390                 395                 400

Gly Thr Gly Ala Thr Thr Gly Thr Gly Cys Gly Thr Ala Ala
                405                 410


<210> SEQ ID NO 10
<211> LENGTH: 137
<212> TYPE: PRT
<213> ORGANISM: Ehrlichia canis

<400> SEQUENCE: 10

Met Leu His Val Gln Asn His Val Asp Gln His Thr Asn His Ile Glu
1               5                   10                  15

His Asp Asp Tyr His Phe Thr Gly Pro Thr Ser Phe Glu Val Asn Leu
            20                  25                  30

Ser Glu Glu Glu Lys Met Glu Leu Gln Glu Val Ser Ser Ile Asp Ser
        35                  40                  45

Val Gly Cys Glu Asp Cys Asp Pro Asn Cys Arg Tyr Pro Leu Glu Leu
    50                  55                  60

Val Glu Cys Gln Arg Ile Glu Glu Arg Pro Val Cys Asn Ala Gly Leu
65                  70                  75                  80

Glu Ser Leu Thr Val Asp Ala Tyr Gln Leu Gly Leu Leu Leu Gly Gly
                85                  90                  95
```

-continued

```
Phe Leu Ser Ala Met Asn Tyr Ile Ser Tyr Ser Tyr Pro Cys Tyr Tyr
            100                 105                 110

Tyr Asp Cys Cys Asp Arg Asn Tyr Tyr Asp Cys Cys His Lys Asn Ala
        115                 120                 125

Cys Tyr Tyr Asn Cys Cys Asp Cys Ala
    130                 135


<210> SEQ ID NO 11
<211> LENGTH: 3018
<212> TYPE: DNA
<213> ORGANISM: Ehrlichia canis

<400> SEQUENCE: 11

atgacgattt tcttagaaag tgatgatgat aagagtaact ttaagaagac attggagaac      60

ggtactaaag acaagacaaa tctagataat acttattatg actatcatca tgaagatgat     120

atgggaaata ctgaatatca ttatgtgagt ttggatagag tggatcatgt taagatgcct     180

gaagagcctg taggttatgg tggagatact ttacctattg ttcctactac agctgctagt     240

gtatctggta gtgatgcagg cgttgctgta ggtaatgtta aagattttga agataatgtt     300

tttcatcata catctactat aagaaacgat gaattgaaga tagatttacg aatacatact     360

ttaaaggatt tatctgataa aagattacgt gaaattgaaa agggatttaa tgatacggta     420

acaaaattta aaaataattt tgggttagaa ccaaatgatg gagaaactat ttttgattta     480

taccttttg atgataagga acaatataat tattatggaa agctttataa cttaggaatt     540

agtggatctg gaggtatgac tttctatgga aatgctaatg ttccatataa aatttatgta     600

catcaatatg gtgaaatatt gaatttaaaa catgaattaa ctcatgcatt agaaagttat     660

gcatctggac ataaattgca tggttctgac gtaaatagca gaatatttac ggaaggatta     720

gctgattata tccaagaaga taatagtttt attatgagag gattaaagga tcgagagatc     780

acttcagatg tattgaaaga ttcttctggt aatgtagatc atttaagtgg tgttgcagtg     840

aatgaaaatc agaggttaag ttatagtata ggacatgcat ttgtaagctt tttacaagag     900

aaatatccta agttaatttc ggaatattta aacgcattaa aagaggataa tattattcgt     960

gctaaagaaa taattagtat ggataagtat ccagattttg agccgtgggt gaagtctaaa    1020

gacattagtt tatatttaga aaatatgaat gtattaaagt taggattagg tgagaaaatg    1080

ttttctgctg aaagtgctag ctattttgaa gatcaaggtg tcaataaaga atattaccat    1140

gaaaatattt atgatatgag tggtaaacta gtaggtgaaa tgtcacctgt agtgcattat    1200

gcacaaaaaa atgtgattcg tatttggaat attgcaagtc ctgatatgat agaggtgcga    1260

ccagaatata actttctgaa attggtaact actccatctg gtaagtctgc atatgtatat    1320

tgtgataaga atgggcatga gtattttaat actaaagatt acatagattc tgcgtttaat    1380

atattggcaa gatatgatgt taagcttcgt gaaagtagtg atgctttgga tattagaggt    1440

cgttactcag atgctgctaa agtgtttagt aagctgccta atgcggattt gctgttggat    1500

aagtttttag aaaaaatagg ttatagtagt tataagcaga taataatgag taatccagaa    1560

cagcttaatt ctattaaggc ttatgtagta aaagaagtgt ttgaaaattt tagggaatct    1620

gaggtcaaaa aggtgttgag tggtgagtct catccggaag taagaaatgt attaatggat    1680

cttacctatg ttgatttaaa gagtgttata ggagtaaatg gtgcagatat tgacagtatt    1740

atttctaatc cagatgtaat gttgcgtact gctgtgttag gtaaaggaaa tgcaagtggg    1800

atatctctat atgtagatga tcagaaagtt ggtgagctgt caactgaagc aggttattgt    1860
```

-continued

```
gttaaaaatc ttgatactgg taaagtgtat tttatgttcc ataatgttgt tggaatgata   1920

gcaagtggtt atgaagacag agcatatatg gttgtattag aaaaagatgg taagtttact   1980

actgctctag ttaataatat acaaaaagca gcagatggaa atgttgtatg ggataatcaa   2040

tttaatcatc cgaatattaa taacttgcac tcaaattata aggagctgtt gttaaatgat   2100

gcttcagtta aagattactc tcatcttgcg gatgtgaaat ttaataaaga tgatacagta   2160

attgttaaag gtgaattatt agatgataaa ggtactgtaa gtgtagatga tgatgtacat   2220

cgtgcagttg ttaagcatga tgatcaaata ctacatcagt ttaagagtat gtctttttac   2280

attactgaac catcagctga ttcaggtgac aattatggaa gtgatttttt catttctgat   2340

gaaggaaaaa atcttagatt tcaacttcct aaagctatta cgcatttgaa attggttaat   2400

gttaatggaa ataataagtt ggtaccatgt actaaagatg ggaatgaaca tcctgaaggt   2460

atgccatctg atttaacgga tgaatataga tatatagatc ctatttttgc tcatacattt   2520

gagaaacaaa gttattctaa aaatagtatt agtgttgggt tagtggactt cagtaaatat   2580

aaagaaggat ctatgtttaa attacagcat tattctgatg attatcatat tcataaggat   2640

gaacaaggta atgttattag gcctaataac agatcttacg ttacaaaagt ggatttagta   2700

tatgatgata aagttattgg gatgttgtct gatagtataa atcaatttca gggtgatatt   2760

ttcatttctg caagccttaa ttatagccac aatgattttc tttcatctaa gtactttcag   2820

aaagttaata ttgaggcgtt agaaaatgga atatatagtg gaagatatga tgtaggagat   2880

ggtgaccaaa tagcaggtct taatactgat acaggttata gtgataaagc tatttttac   2940

tttaaaaatg atagcgcatc tactgatatg ccggctagtg atgttactac tattttacct   3000

tatataaatg agctttaa                                                 3018


<210> SEQ ID NO 12
<211> LENGTH: 1005
<212> TYPE: PRT
<213> ORGANISM: Ehrlichia canis

<400> SEQUENCE: 12

Met Thr Ile Phe Leu Glu Ser Asp Asp Asp Lys Ser Asn Phe Lys Lys
1               5                   10                  15

Thr Leu Glu Asn Gly Thr Lys Asp Lys Thr Asn Leu Asp Asn Thr Tyr
            20                  25                  30

Tyr Asp Tyr His His Glu Asp Asp Met Gly Asn Thr Glu Tyr His Tyr
        35                  40                  45

Val Ser Leu Asp Arg Val Asp His Val Lys Met Pro Glu Glu Pro Val
    50                  55                  60

Gly Tyr Gly Gly Asp Thr Leu Pro Ile Val Pro Thr Thr Ala Ala Ser
65                  70                  75                  80

Val Ser Gly Ser Asp Ala Gly Val Ala Val Gly Asn Val Lys Asp Phe
                85                  90                  95

Glu Asp Asn Val Phe His His Thr Ser Thr Ile Arg Asn Asp Glu Leu
            100                 105                 110

Lys Ile Asp Leu Arg Ile His Thr Leu Lys Asp Leu Ser Asp Lys Arg
        115                 120                 125

Leu Arg Glu Ile Glu Lys Gly Phe Asn Asp Thr Val Thr Lys Phe Lys
    130                 135                 140

Asn Asn Phe Gly Leu Glu Pro Asn Asp Gly Glu Thr Ile Phe Asp Leu
145                 150                 155                 160

Tyr Leu Phe Asp Asp Lys Glu Gln Tyr Asn Tyr Tyr Gly Lys Leu Tyr
```

-continued

```
                165                 170                 175

Asn Leu Gly Ile Ser Gly Ser Gly Gly Met Thr Phe Tyr Gly Asn Ala
            180                 185                 190

Asn Val Pro Tyr Lys Ile Tyr Val His Gln Tyr Gly Glu Ile Leu Asn
        195                 200                 205

Leu Lys His Glu Leu Thr His Ala Leu Glu Ser Tyr Ala Ser Gly His
    210                 215                 220

Lys Leu His Gly Ser Asp Val Asn Ser Arg Ile Phe Thr Glu Gly Leu
225                 230                 235                 240

Ala Asp Tyr Ile Gln Glu Asp Asn Ser Phe Ile Met Arg Gly Leu Lys
                245                 250                 255

Asp Arg Glu Ile Thr Ser Asp Val Leu Lys Asp Ser Ser Gly Asn Val
            260                 265                 270

Asp His Leu Ser Gly Val Ala Val Asn Glu Asn Gln Arg Leu Ser Tyr
        275                 280                 285

Ser Ile Gly His Ala Phe Val Ser Phe Leu Gln Glu Lys Tyr Pro Lys
    290                 295                 300

Leu Ile Ser Glu Tyr Leu Asn Ala Leu Lys Glu Asp Asn Ile Ile Arg
305                 310                 315                 320

Ala Lys Glu Ile Ile Ser Met Asp Lys Tyr Pro Asp Phe Glu Pro Trp
                325                 330                 335

Val Lys Ser Lys Asp Ile Ser Leu Tyr Leu Glu Asn Met Asn Val Leu
            340                 345                 350

Lys Leu Gly Leu Gly Glu Lys Met Phe Ser Ala Glu Ser Ala Ser Tyr
        355                 360                 365

Phe Glu Asp Gln Gly Val Asn Lys Glu Tyr Tyr His Glu Asn Ile Tyr
    370                 375                 380

Asp Met Ser Gly Lys Leu Val Gly Glu Met Ser Pro Val Val His Tyr
385                 390                 395                 400

Ala Gln Lys Asn Val Ile Arg Ile Trp Asn Ile Ala Ser Pro Asp Met
                405                 410                 415

Ile Glu Val Arg Pro Glu Tyr Asn Phe Leu Lys Leu Val Thr Thr Pro
            420                 425                 430

Ser Gly Lys Ser Ala Tyr Val Tyr Cys Asp Lys Asn Gly His Glu Tyr
        435                 440                 445

Phe Asn Thr Lys Asp Tyr Ile Asp Ser Ala Phe Asn Ile Leu Ala Arg
    450                 455                 460

Tyr Asp Val Lys Leu Arg Glu Ser Ser Asp Ala Leu Asp Ile Arg Gly
465                 470                 475                 480

Arg Tyr Ser Asp Ala Ala Lys Val Phe Ser Lys Leu Pro Asn Ala Asp
                485                 490                 495

Leu Leu Leu Asp Lys Phe Leu Glu Lys Ile Gly Tyr Ser Ser Tyr Lys
            500                 505                 510

Gln Ile Ile Met Ser Asn Pro Glu Gln Leu Asn Ser Ile Lys Ala Tyr
        515                 520                 525

Val Val Lys Glu Val Phe Glu Asn Phe Arg Glu Ser Glu Val Lys Lys
    530                 535                 540

Val Leu Ser Gly Glu Ser His Pro Glu Val Arg Asn Val Leu Met Asp
545                 550                 555                 560

Leu Thr Tyr Val Asp Leu Lys Ser Val Ile Gly Val Asn Gly Ala Asp
                565                 570                 575

Ile Asp Ser Ile Ile Ser Asn Pro Asp Val Met Leu Arg Thr Ala Val
            580                 585                 590
```

```
Leu Gly Lys Gly Asn Ala Ser Gly Ile Ser Leu Tyr Val Asp Asp Gln
        595                 600                 605

Lys Val Gly Glu Leu Ser Thr Glu Ala Gly Tyr Cys Val Lys Asn Leu
    610                 615                 620

Asp Thr Gly Lys Val Tyr Phe Met Phe His Asn Val Val Gly Met Ile
625                 630                 635                 640

Ala Ser Gly Tyr Glu Asp Arg Ala Tyr Met Val Val Leu Glu Lys Asp
                645                 650                 655

Gly Lys Phe Thr Thr Ala Leu Val Asn Asn Ile Gln Lys Ala Ala Asp
            660                 665                 670

Gly Asn Val Val Trp Asp Asn Gln Phe Asn His Pro Asn Ile Asn Asn
        675                 680                 685

Leu His Ser Asn Tyr Lys Glu Leu Leu Leu Asn Asp Ala Ser Val Lys
    690                 695                 700

Asp Tyr Ser His Leu Ala Asp Val Lys Phe Asn Lys Asp Asp Thr Val
705                 710                 715                 720

Ile Val Lys Gly Glu Leu Leu Asp Asp Lys Gly Thr Val Ser Val Asp
                725                 730                 735

Asp Asp Val His Arg Ala Val Val Lys His Asp Asp Gln Ile Leu His
            740                 745                 750

Gln Phe Lys Ser Met Ser Phe Tyr Ile Thr Glu Pro Ser Ala Asp Ser
        755                 760                 765

Gly Asp Asn Tyr Gly Ser Asp Phe Phe Ile Ser Asp Glu Gly Lys Asn
    770                 775                 780

Leu Arg Phe Gln Leu Pro Lys Ala Ile Thr His Leu Lys Leu Val Asn
785                 790                 795                 800

Val Asn Gly Asn Asn Lys Leu Val Pro Cys Thr Lys Asp Gly Asn Glu
                805                 810                 815

His Pro Glu Gly Met Pro Ser Asp Leu Thr Asp Glu Tyr Arg Tyr Ile
            820                 825                 830

Asp Pro Ile Phe Ala His Thr Phe Glu Lys Gln Ser Tyr Ser Lys Asn
        835                 840                 845

Ser Ile Ser Val Gly Leu Val Asp Phe Ser Lys Tyr Lys Glu Gly Ser
    850                 855                 860

Met Phe Lys Leu Gln His Tyr Ser Asp Asp Tyr His Ile His Lys Asp
865                 870                 875                 880

Glu Gln Gly Asn Val Ile Arg Pro Asn Asn Arg Ser Tyr Val Thr Lys
                885                 890                 895

Val Asp Leu Val Tyr Asp Asp Lys Val Ile Gly Met Leu Ser Asp Ser
            900                 905                 910

Ile Asn Gln Phe Gln Gly Asp Ile Phe Ile Ser Ala Ser Leu Asn Tyr
        915                 920                 925

Ser His Asn Asp Phe Leu Ser Ser Lys Tyr Phe Gln Lys Val Asn Ile
    930                 935                 940

Glu Ala Leu Glu Asn Gly Ile Tyr Ser Gly Arg Tyr Asp Val Gly Asp
945                 950                 955                 960

Gly Asp Gln Ile Ala Gly Leu Asn Thr Asp Thr Gly Tyr Ser Asp Lys
                965                 970                 975

Ala Ile Phe Tyr Phe Lys Asn Asp Ser Ala Ser Thr Asp Met Pro Ala
            980                 985                 990

Ser Asp Val Thr Thr Ile Leu Pro  Tyr Ile Asn Glu Leu
        995                 1000                1005
```

-continued

<210> SEQ ID NO 13
<211> LENGTH: 2172
<212> TYPE: DNA
<213> ORGANISM: Ehrlichia canis

<400> SEQUENCE: 13
atggatagta taagtgcaaa tcacatacgc aatattttat tccttgtttt aggcgcattt 60
tttggactgg aattttgctt ttatttatca ggtgtattat tcatcttaat ggtctgggga 120
ccaaattacc tagattttaa tgctataaat cccagtttga gtgattttcc agacagaatt 180
tggccaacta tttttgacta tgtacaacat tggtggaaga acccttctgc atacgatgca 240
gttttattac ttaagctaat aacgtcatta tgtacaccag taggtattct aagcatagta 300
ttatggaacc ttagaaatat attattcgat tggaggccat ttaagaagaa agaatcactg 360
catggagatt caagatgggc aacagaaaaa gatattcgca aaataggatt acgtagtaga 420
aaaggaatat tattagggaa agacaagaga ggatatctca ttgcagatgg atatcaacat 480
gcattgttat ttgcaccaac tggatccgga aaaggtgtag gttttgtaat accaaactta 540
ttattctggg aagattctgt agtagtacac gatataaaat tagagaacta tgatcttaca 600
agtgggtgga gaaaaaaaag ggacaagaa gttttcgtgt ggaacccagc acaacctgac 660
ggtataagtc actgttacaa cccattagat tggataagct ctaagcctgg acaaatggta 720
gatgatgtac aaaaaattgc caatctaata atgcctgaac aagatttttg gtataacgaa 780
gcacgtagtt tatttgtagg agtagtatta tacttactag cagtaccaga aaaagtaaaa 840
tcctttggag aagttgtaag aacaatgcgc agcgatgacg tagtctacaa cttagcagta 900
gtactagaca caatagggaa aaagattcac ccagttgcat acatgaatat agctgcattt 960
ttacaaaaag cagacaaaga acgctcaggt gttgtatcaa ctatgaactc atctttagaa 1020
ttatgggcaa acccattaat agatacagca acagcatcaa gtgattttaa tattcaagaa 1080
tttaaaagga aaaaagtaac agtatatgtt ggattaacac cagataattt aactcgtctt 1140
agacctttaa tgcaggtatt ttatcaacaa gctacagaat tttatgtag aactttacca 1200 tcagatgatg aaccatatgg tgtactgttc ttaatggatg agtttccaac attaggaaaa 1260
atggagcaat ttcaaacagg tatcgcatat ttccgtggat atagagttag actattttg 1320 attattcaag atactgaaca gcttaagggt atatatgaag aagcaggaat gaactcattc 1380
ttatcaaact ctacttatag aataactttt gctgcaaata atatagaaac tgcaaattta 1440
atatcacagt taataggaaa taaaactgtt aaccaagagt ctttaaacag acctaaattt 1500
ttagatttga accctgcatc acgttcatta catatatcag aaacacaaag agctttacta 1560
ttacctcaag aagtaataat gttacccaga gatgagcaaa tacttttaat agaatctact 1620
tatcctataa aatcaaagaa aataaaatac tatgaagaca aaaattttac aaaaaaacta 1680
ttaaagagta cctttgttcc aactcaagag ccttatgatc ccaacaaaac aaaaacagca 1740
acaaaagaaa acgaagaacc tatgccaagt attgaaagcg atcttcctaa aaatacatct 1800
gacaatactg aaaacaatat ggaagatggt gcaatgtaca gcagcataga agaagattat 1860
gacgatgatg atgatgattt taattttgaa gacttagatg aatatatgga tgaagaagaa 1920
gattatgatg atgaagaata tgatgatata gattatgatg ataataacaa tagtaatgag 1980
gagtatgaag aagataatcc agaagaagat gacaatagca ataatctaga cgatgaggaa 2040
gaggaagaag ataatattat agattatgaa gatgaagaag aatatgatga taacatagac 2100
tacaaagatg atgacaataa ctacaacaaa gataccactg acgatcaaga ctcaaaaaaa 2160

-continued

```
cataatgaat ag                                                       2172


<210> SEQ ID NO 14
<211> LENGTH: 723
<212> TYPE: PRT
<213> ORGANISM: Ehrlichia canis

<400> SEQUENCE: 14

Met Asp Ser Ile Ser Ala Asn His Ile Arg Asn Ile Leu Phe Leu Val
1               5                   10                  15

Leu Gly Ala Phe Phe Gly Leu Glu Phe Cys Phe Tyr Leu Ser Gly Val
            20                  25                  30

Leu Phe Ile Leu Met Val Trp Gly Pro Asn Tyr Leu Asp Phe Asn Ala
        35                  40                  45

Ile Asn Pro Ser Leu Ser Asp Phe Pro Asp Arg Ile Trp Pro Thr Ile
    50                  55                  60

Phe Asp Tyr Val Gln His Trp Trp Lys Asn Pro Ser Ala Tyr Asp Ala
65                  70                  75                  80

Val Leu Leu Leu Lys Leu Ile Thr Ser Leu Cys Thr Pro Val Gly Ile
                85                  90                  95

Leu Ser Ile Val Leu Trp Asn Leu Arg Asn Ile Leu Phe Asp Trp Arg
            100                 105                 110

Pro Phe Lys Lys Lys Glu Ser Leu His Gly Asp Ser Arg Trp Ala Thr
        115                 120                 125

Glu Lys Asp Ile Arg Lys Ile Gly Leu Arg Ser Arg Lys Gly Ile Leu
    130                 135                 140

Leu Gly Lys Asp Lys Arg Gly Tyr Leu Ile Ala Asp Gly Tyr Gln His
145                 150                 155                 160

Ala Leu Leu Phe Ala Pro Thr Gly Ser Gly Lys Gly Val Gly Phe Val
                165                 170                 175

Ile Pro Asn Leu Leu Phe Trp Glu Asp Ser Val Val Val His Asp Ile
            180                 185                 190

Lys Leu Glu Asn Tyr Asp Leu Thr Ser Gly Trp Arg Lys Lys Arg Gly
        195                 200                 205

Gln Glu Val Phe Val Trp Asn Pro Ala Gln Pro Asp Gly Ile Ser His
    210                 215                 220

Cys Tyr Asn Pro Leu Asp Trp Ile Ser Ser Lys Pro Gly Gln Met Val
225                 230                 235                 240

Asp Asp Val Gln Lys Ile Ala Asn Leu Ile Met Pro Glu Gln Asp Phe
                245                 250                 255

Trp Tyr Asn Glu Ala Arg Ser Leu Phe Val Gly Val Val Leu Tyr Leu
            260                 265                 270

Leu Ala Val Pro Glu Lys Val Lys Ser Phe Gly Glu Val Val Arg Thr
        275                 280                 285

Met Arg Ser Asp Asp Val Val Tyr Asn Leu Ala Val Val Leu Asp Thr
    290                 295                 300

Ile Gly Lys Lys Ile His Pro Val Ala Tyr Met Asn Ile Ala Ala Phe
305                 310                 315                 320

Leu Gln Lys Ala Asp Lys Glu Arg Ser Gly Val Val Ser Thr Met Asn
                325                 330                 335

Ser Ser Leu Glu Leu Trp Ala Asn Pro Leu Ile Asp Thr Ala Thr Ala
            340                 345                 350

Ser Ser Asp Phe Asn Ile Gln Glu Phe Lys Arg Lys Lys Val Thr Val
        355                 360                 365
```

-continued

```
Tyr Val Gly Leu Thr Pro Asp Asn Leu Thr Arg Leu Arg Pro Leu Met
    370                 375                 380

Gln Val Phe Tyr Gln Gln Ala Thr Glu Phe Leu Cys Arg Thr Leu Pro
385                 390                 395                 400

Ser Asp Asp Glu Pro Tyr Gly Val Leu Phe Leu Met Asp Glu Phe Pro
                405                 410                 415

Thr Leu Gly Lys Met Glu Gln Phe Gln Thr Gly Ile Ala Tyr Phe Arg
            420                 425                 430

Gly Tyr Arg Val Arg Leu Phe Leu Ile Ile Gln Asp Thr Glu Gln Leu
        435                 440                 445

Lys Gly Ile Tyr Glu Glu Ala Gly Met Asn Ser Phe Leu Ser Asn Ser
    450                 455                 460

Thr Tyr Arg Ile Thr Phe Ala Ala Asn Asn Ile Glu Thr Ala Asn Leu
465                 470                 475                 480

Ile Ser Gln Leu Ile Gly Asn Lys Thr Val Asn Gln Glu Ser Leu Asn
                485                 490                 495

Arg Pro Lys Phe Leu Asp Leu Asn Pro Ala Ser Arg Ser Leu His Ile
            500                 505                 510

Ser Glu Thr Gln Arg Ala Leu Leu Leu Pro Gln Glu Val Ile Met Leu
        515                 520                 525

Pro Arg Asp Glu Gln Ile Leu Leu Ile Glu Ser Thr Tyr Pro Ile Lys
    530                 535                 540

Ser Lys Lys Ile Lys Tyr Tyr Glu Asp Lys Asn Phe Thr Lys Lys Leu
545                 550                 555                 560

Leu Lys Ser Thr Phe Val Pro Thr Gln Glu Pro Tyr Asp Pro Asn Lys
                565                 570                 575

Thr Lys Thr Ala Thr Lys Glu Asn Glu Glu Pro Met Pro Ser Ile Glu
            580                 585                 590

Ser Asp Leu Pro Lys Asn Thr Ser Asp Asn Thr Glu Asn Asn Met Glu
        595                 600                 605

Asp Gly Ala Met Tyr Ser Ser Ile Glu Glu Asp Tyr Asp Asp Asp Asp
    610                 615                 620

Asp Asp Phe Asn Phe Glu Asp Leu Asp Glu Tyr Met Asp Glu Glu Glu
625                 630                 635                 640

Asp Tyr Asp Asp Glu Glu Tyr Asp Asp Ile Asp Tyr Asp Asp Asn Asn
                645                 650                 655

Asn Ser Asn Glu Glu Tyr Glu Glu Asp Asn Pro Glu Glu Asp Asp Asn
            660                 665                 670

Ser Asn Asn Leu Asp Asp Glu Glu Glu Glu Glu Asp Asn Ile Ile Asp
        675                 680                 685

Tyr Glu Asp Glu Glu Glu Tyr Asp Asp Asn Ile Asp Tyr Lys Asp Asp
    690                 695                 700

Asp Asn Asn Tyr Asn Lys Asp Thr Thr Asp Asp Gln Asp Ser Lys Lys
705                 710                 715                 720

His Asn Glu


<210> SEQ ID NO 15
<211> LENGTH: 688
<212> TYPE: PRT
<213> ORGANISM: Ehrlichia canis

<400> SEQUENCE: 15

Met Asp Ile Asp Asn Asn Asn Val Thr Thr Ser Ser Thr Gln Asp Lys
1               5                   10                  15
```

-continued

```
Ser Gly Asn Leu Met Glu Val Ile Met Arg Ile Leu Asn Phe Gly Asn
            20                  25                  30

Asn Ser Asp Glu Lys Val Ser Asn Glu Asp Thr Lys Val Leu Val Glu
        35                  40                  45

Ser Leu Gln Pro Ala Val Asn Asp Asn Val Gly Asn Pro Ser Ser Glu
    50                  55                  60

Val Gly Lys Glu Glu Asn Ala Pro Glu Val Lys Ala Glu Asp Leu Gln
65                  70                  75                  80

Pro Ala Val Asp Gly Ser Val Glu His Ser Ser Ser Glu Val Gly Lys
                85                  90                  95

Lys Val Ser Glu Thr Ser Lys Glu Glu Ser Thr Pro Glu Val Lys Ala
            100                 105                 110

Glu Asp Leu Gln Pro Ala Val Asp Gly Ser Ile Glu His Ser Ser Ser
        115                 120                 125

Glu Val Gly Glu Lys Val Ser Lys Thr Ser Lys Glu Glu Ser Thr Pro
    130                 135                 140

Glu Val Lys Ala Glu Asp Leu Gln Pro Ala Val Asp Asp Ser Val Glu
145                 150                 155                 160

His Ser Ser Ser Glu Val Gly Glu Lys Val Ser Glu Thr Ser Lys Glu
                165                 170                 175

Glu Asn Thr Pro Glu Val Lys Ala Glu Asp Leu Gln Pro Ala Val Asp
            180                 185                 190

Gly Ser Ile Glu His Ser Ser Ser Glu Val Gly Glu Lys Val Ser Lys
        195                 200                 205

Thr Ser Lys Glu Glu Ser Thr Pro Glu Val Lys Ala Glu Asp Leu Gln
    210                 215                 220

Pro Ala Val Asp Asp Ser Val Glu His Ser Ser Ser Glu Val Gly Glu
225                 230                 235                 240

Lys Val Ser Glu Thr Ser Lys Glu Glu Asn Thr Pro Glu Val Lys Ala
                245                 250                 255

Glu Asp Leu Gln Pro Ala Val Asp Gly Ser Val Glu His Ser Ser Ser
            260                 265                 270

Glu Val Gly Glu Lys Val Ser Lys Thr Ser Lys Glu Glu Ser Thr Pro
        275                 280                 285

Glu Val Lys Ala Glu Asp Leu Gln Pro Ala Val Asp Asp Ser Val Glu
    290                 295                 300

His Ser Ser Ser Glu Val Gly Glu Lys Val Ser Glu Thr Ser Lys Glu
305                 310                 315                 320

Glu Asn Thr Pro Glu Val Arg Ala Glu Asp Leu Gln Pro Ala Val Asp
                325                 330                 335

Gly Ser Val Glu His Ser Ser Ser Glu Val Gly Glu Lys Val Ser Glu
            340                 345                 350

Thr Ser Lys Glu Glu Ser Thr Pro Glu Val Lys Ala Glu Asp Leu Gln
        355                 360                 365

Pro Ala Val Asp Ser Ser Ile Glu His Ser Ser Ser Glu Val Gly Lys
    370                 375                 380

Lys Val Ser Glu Thr Ser Lys Glu Glu Ser Thr Pro Glu Val Lys Ala
385                 390                 395                 400

Glu Asp Leu Gln Pro Ala Val Asp Gly Ser Val Glu His Ser Ser Ser
                405                 410                 415

Glu Val Gly Glu Lys Val Ser Glu Thr Ser Lys Glu Glu Asn Thr Pro
            420                 425                 430
```

-continued

```
Glu Val Lys Ala Glu Asp Leu Gln Pro Ala Val Asp Gly Ser Val Glu
        435                 440                 445

His Ser Ser Ser Glu Val Gly Glu Lys Val Ser Glu Thr Ser Lys Glu
    450                 455                 460

Glu Asn Thr Pro Glu Val Lys Ala Glu Asp Leu Gln Pro Ala Val Asp
465                 470                 475                 480

Gly Ser Val Glu His Ser Ser Ser Glu Val Gly Glu Lys Val Ser Glu
                485                 490                 495

Thr Ser Lys Glu Glu Ser Thr Pro Glu Val Lys Ala Glu Asp Leu Gln
            500                 505                 510

Pro Ala Val Asp Asp Ser Val Glu His Ser Ser Ser Glu Val Gly Glu
        515                 520                 525

Lys Val Ser Glu Thr Ser Lys Glu Glu Ser Thr Pro Glu Val Lys Ala
    530                 535                 540

Glu Asp Leu Gln Pro Ala Val Asp Gly Ser Val Glu His Ser Ser Ser
545                 550                 555                 560

Glu Val Gly Glu Lys Val Ser Glu Thr Ser Lys Glu Glu Ser Thr Pro
                565                 570                 575

Glu Val Lys Ala Glu Val Gln Pro Val Ala Asp Gly Asn Pro Val Pro
            580                 585                 590

Leu Asn Pro Met Pro Ser Ile Asp Asn Ile Asp Thr Asn Ile Ile Phe
        595                 600                 605

His Tyr His Lys Asp Cys Lys Lys Gly Ser Ala Val Gly Thr Asp Glu
    610                 615                 620

Met Cys Cys Pro Val Ser Glu Leu Met Ala Gly Glu His Val His Met
625                 630                 635                 640

Tyr Gly Ile Tyr Val Tyr Arg Val Gln Ser Val Lys Asp Leu Ser Gly
                645                 650                 655

Val Phe Asn Ile Asp His Ser Thr Cys Asp Cys Asn Leu Asp Val Tyr
            660                 665                 670

Phe Val Gly Tyr Asn Ser Phe Thr Asn Lys Glu Thr Val Asp Leu Ile
        675                 680                 685


<210> SEQ ID NO 16
<211> LENGTH: 515
<212> TYPE: PRT
<213> ORGANISM: Ehrlichia canis

<400> SEQUENCE: 16

Lys Glu Glu Asn Ala Pro Glu Val Lys Ala Glu Asp Leu Gln Pro Ala
1               5                   10                  15

Val Asp Gly Ser Val Glu His Ser Ser Ser Glu Val Gly Lys Lys Val
            20                  25                  30

Ser Glu Thr Ser Lys Glu Glu Ser Thr Pro Glu Val Lys Ala Glu Asp
        35                  40                  45

Leu Gln Pro Ala Val Asp Gly Ser Ile Glu His Ser Ser Ser Glu Val
    50                  55                  60

Gly Glu Lys Val Ser Lys Thr Ser Lys Glu Glu Ser Thr Pro Glu Val
65                  70                  75                  80

Lys Ala Glu Asp Leu Gln Pro Ala Val Asp Asp Ser Val Glu His Ser
                85                  90                  95

Ser Ser Glu Val Gly Glu Lys Val Ser Glu Thr Ser Lys Glu Glu Asn
            100                 105                 110

Thr Pro Glu Val Lys Ala Glu Asp Leu Gln Pro Ala Val Asp Gly Ser
        115                 120                 125
```

```
Ile Glu His Ser Ser Ser Glu Val Gly Glu Lys Val Ser Lys Thr Ser
    130                 135                 140

Lys Glu Glu Ser Thr Pro Glu Val Lys Ala Glu Asp Leu Gln Pro Ala
145                 150                 155                 160

Val Asp Asp Ser Val Glu His Ser Ser Ser Glu Val Gly Glu Lys Val
                165                 170                 175

Ser Glu Thr Ser Lys Glu Glu Asn Thr Pro Glu Val Lys Ala Glu Asp
            180                 185                 190

Leu Gln Pro Ala Val Asp Gly Ser Val Glu His Ser Ser Ser Glu Val
        195                 200                 205

Gly Glu Lys Val Ser Lys Thr Ser Lys Glu Glu Ser Thr Pro Glu Val
    210                 215                 220

Lys Ala Glu Asp Leu Gln Pro Ala Val Asp Asp Ser Val Glu His Ser
225                 230                 235                 240

Ser Ser Glu Val Gly Glu Lys Val Ser Glu Thr Ser Lys Glu Glu Asn
                245                 250                 255

Thr Pro Glu Val Arg Ala Glu Asp Leu Gln Pro Ala Val Asp Gly Ser
            260                 265                 270

Val Glu His Ser Ser Ser Glu Val Gly Glu Lys Val Ser Glu Thr Ser
        275                 280                 285

Lys Glu Glu Ser Thr Pro Glu Val Lys Ala Glu Asp Leu Gln Pro Ala
    290                 295                 300

Val Asp Ser Ser Ile Glu His Ser Ser Ser Glu Val Gly Lys Lys Val
305                 310                 315                 320

Ser Glu Thr Ser Lys Glu Glu Ser Thr Pro Glu Val Lys Ala Glu Asp
                325                 330                 335

Leu Gln Pro Ala Val Asp Gly Ser Val Glu His Ser Ser Ser Glu Val
            340                 345                 350

Gly Glu Lys Val Ser Glu Thr Ser Lys Glu Glu Asn Thr Pro Glu Val
        355                 360                 365

Lys Ala Glu Asp Leu Gln Pro Ala Val Asp Gly Ser Val Glu His Ser
    370                 375                 380

Ser Ser Glu Val Gly Glu Lys Val Ser Glu Thr Ser Lys Glu Glu Asn
385                 390                 395                 400

Thr Pro Glu Val Lys Ala Glu Asp Leu Gln Pro Ala Val Asp Gly Ser
                405                 410                 415

Val Glu His Ser Ser Ser Glu Val Gly Glu Lys Val Ser Glu Thr Ser
            420                 425                 430

Lys Glu Glu Ser Thr Pro Glu Val Lys Ala Glu Asp Leu Gln Pro Ala
        435                 440                 445

Val Asp Asp Ser Val Glu His Ser Ser Ser Glu Val Gly Glu Lys Val
    450                 455                 460

Ser Glu Thr Ser Lys Glu Glu Ser Thr Pro Glu Val Lys Ala Glu Asp
465                 470                 475                 480

Leu Gln Pro Ala Val Asp Gly Ser Val Glu His Ser Ser Ser Glu Val
                485                 490                 495

Gly Glu Lys Val Ser Glu Thr Ser Lys Glu Glu Ser Thr Pro Glu Val
            500                 505                 510

Lys Ala Glu
        515
```

<210> SEQ ID NO 17
<211> LENGTH: 36

```
<212> TYPE: PRT
<213> ORGANISM: Ehrlichia canis
<220> FEATURE:
<221> NAME/KEY: MISC_FEATURE
<222> LOCATION: (4)..(4)
<223> OTHER INFORMATION: X stands for any amino acid
<220> FEATURE:
<221> NAME/KEY: MISC_FEATURE
<222> LOCATION: (9)..(9)
<223> OTHER INFORMATION: X stands for any amino acid
<220> FEATURE:
<221> NAME/KEY: MISC_FEATURE
<222> LOCATION: (19)..(19)
<223> OTHER INFORMATION: X stands for any amino acid
<220> FEATURE:
<221> NAME/KEY: MISC_FEATURE
<222> LOCATION: (21)..(21)
<223> OTHER INFORMATION: X stands for any amino acid
<220> FEATURE:
<221> NAME/KEY: MISC_FEATURE
<222> LOCATION: (30)..(30)
<223> OTHER INFORMATION: X stands for any amino acid
<220> FEATURE:
<221> NAME/KEY: MISC_FEATURE
<222> LOCATION: (34)..(34)
<223> OTHER INFORMATION: X stands for any amino acid

<400> SEQUENCE: 17

Lys Glu Glu Xaa Thr Pro Glu Val Xaa Ala Glu Asp Leu Gln Pro Ala
1               5                   10                  15

Val Asp Xaa Ser Xaa Glu His Ser Ser Ser Glu Val Gly Xaa Lys Val
            20                  25                  30

Ser Xaa Thr Ser
        35


<210> SEQ ID NO 18
<211> LENGTH: 19
<212> TYPE: PRT
<213> ORGANISM: Ehrlichia canis

<400> SEQUENCE: 18

Cys Pro Glu Val Lys Ala Glu Asp Leu Gln Pro Ala Val Asp Gly Ser
1               5                   10                  15

Val Glu His


<210> SEQ ID NO 19
<211> LENGTH: 27
<212> TYPE: PRT
<213> ORGANISM: Ehrlichia canis

<400> SEQUENCE: 19

Cys Glu Val Gly Lys Glu Glu Asn Ala Pro Glu Val Lys Ala Glu Asp
1               5                   10                  15

Leu Gln Pro Ala Val Asp Gly Ser Val Glu His
            20                  25


<210> SEQ ID NO 20
<211> LENGTH: 37
<212> TYPE: PRT
<213> ORGANISM: Ehrlichia canis

<400> SEQUENCE: 20

Cys Lys Glu Glu Ser Thr Pro Glu Val Lys Ala Glu Asp Leu Gln Pro
1               5                   10                  15

Ala Val Asp Gly Ser Val Glu His Ser Ser Ser Glu Val Gly Glu Lys
            20                  25                  30
```

-continued

```
Val Ser Glu Thr Ser
        35


<210> SEQ ID NO 21
<211> LENGTH: 48
<212> TYPE: PRT
<213> ORGANISM: Ehrlichia canis
<220> FEATURE:
<221> NAME/KEY: MISC_FEATURE
<222> LOCATION: (1)..(15)
<223> OTHER INFORMATION: X stands for any amino acid or no amino acid
<220> FEATURE:
<221> NAME/KEY: MISC_FEATURE
<222> LOCATION: (34)..(48)
<223> OTHER INFORMATION: X stands for any amino acid or no amino acid

<400> SEQUENCE: 21

Xaa Xaa Xaa Xaa Xaa Xaa Xaa Xaa Xaa Xaa Xaa Xaa Xaa Xaa Xaa Pro
1               5                   10                  15

Glu Val Lys Ala Glu Asp Leu Gln Pro Ala Val Asp Gly Ser Val Glu
            20                  25                  30

His Xaa Xaa Xaa Xaa Xaa Xaa Xaa Xaa Xaa Xaa Xaa Xaa Xaa Xaa Xaa
        35                  40                  45


<210> SEQ ID NO 22
<211> LENGTH: 30
<212> TYPE: PRT
<213> ORGANISM: Ehrlichia canis

<400> SEQUENCE: 22

Cys Thr Asn His Ile Glu His Asp Asp Tyr His Phe Thr Gly Pro Thr
1               5                   10                  15

Ser Phe Glu Val Asn Leu Ser Glu Glu Glu Lys Met Glu Leu
            20                  25                  30


<210> SEQ ID NO 23
<211> LENGTH: 30
<212> TYPE: PRT
<213> ORGANISM: Ehrlichia canis

<400> SEQUENCE: 23

Cys Thr Asn His Ile Glu His Asp Asp Tyr His Phe Thr Gly Pro Thr
1               5                   10                  15

Ser Phe Glu Val Asn Leu Ser Glu Glu Glu Lys Met Glu Leu
            20                  25                  30


<210> SEQ ID NO 24
<211> LENGTH: 27
<212> TYPE: PRT
<213> ORGANISM: Ehrlichia canis

<400> SEQUENCE: 24

Cys Thr Gly Pro Thr Ser Phe Glu Val Asn Leu Ser Glu Glu Glu Lys
1               5                   10                  15

Met Glu Leu Gln Glu Val Ser Ser Ile Asp Ser
            20                  25


<210> SEQ ID NO 25
<211> LENGTH: 27
<212> TYPE: PRT
<213> ORGANISM: Ehrlichia canis
<220> FEATURE:
<221> NAME/KEY: MISC_FEATURE
<222> LOCATION: (1)..(1)
<223> OTHER INFORMATION: X stands for C or is absent
```

```
<220> FEATURE:
<221> NAME/KEY: MISC_FEATURE
<222> LOCATION: (4)..(4)
<223> OTHER INFORMATION: X stands for H or Q
<220> FEATURE:
<221> NAME/KEY: MISC_FEATURE
<222> LOCATION: (25)..(25)
<223> OTHER INFORMATION: X stands for D or G

<400> SEQUENCE: 25

Xaa Met Leu Xaa Val Gln Asn His Val Asp Gln His Thr Asn His Ile
1               5                   10                  15

Glu His Asp Asp Tyr His Phe Thr Xaa Pro Thr
            20                  25


<210> SEQ ID NO 26
<211> LENGTH: 30
<212> TYPE: PRT
<213> ORGANISM: Ehrlichia canis
<220> FEATURE:
<221> NAME/KEY: MISC_FEATURE
<222> LOCATION: (1)..(1)
<223> OTHER INFORMATION: X stands for C or is absent
<220> FEATURE:
<221> NAME/KEY: MISC_FEATURE
<222> LOCATION: (14)..(14)
<223> OTHER INFORMATION: X stands for G or D

<400> SEQUENCE: 26

Xaa Thr Asn His Ile Glu His Asp Asp Tyr His Phe Thr Xaa Pro Thr
1               5                   10                  15

Ser Phe Glu Val Asn Leu Ser Glu Glu Glu Lys Met Glu Leu
            20                  25                  30


<210> SEQ ID NO 27
<211> LENGTH: 27
<212> TYPE: PRT
<213> ORGANISM: Ehrlichia canis
<220> FEATURE:
<221> NAME/KEY: MISC_FEATURE
<222> LOCATION: (1)..(1)
<223> OTHER INFORMATION: X stands for C or is absent
<220> FEATURE:
<221> NAME/KEY: MISC_FEATURE
<222> LOCATION: (3)..(3)
<223> OTHER INFORMATION: X stands for G or D

<400> SEQUENCE: 27

Xaa Thr Xaa Pro Thr Ser Phe Glu Val Asn Leu Ser Glu Glu Glu Lys
1               5                   10                  15

Met Glu Leu Gln Glu Val Ser Ser Ile Asp Ser
            20                  25


<210> SEQ ID NO 28
<211> LENGTH: 16
<212> TYPE: PRT
<213> ORGANISM: Ehrlichia canis
<220> FEATURE:
<221> NAME/KEY: MISC_FEATURE
<222> LOCATION: (1)..(1)
<223> OTHER INFORMATION: X stands for C or is absent
<220> FEATURE:
<221> NAME/KEY: MISC_FEATURE
<222> LOCATION: (14)..(14)
<223> OTHER INFORMATION: X stands for G or D

<400> SEQUENCE: 28

Xaa Thr Asn His Ile Glu His Asp Asp Tyr His Phe Thr Xaa Pro Thr
1               5                   10                  15
```

```
<210> SEQ ID NO 29
<211> LENGTH: 19
<212> TYPE: PRT
<213> ORGANISM: Ehrlichia canis
<220> FEATURE:
<221> NAME/KEY: MISC_FEATURE
<222> LOCATION: (1)..(1)
<223> OTHER INFORMATION: X stands for C or is absent
<220> FEATURE:
<221> NAME/KEY: MISC_FEATURE
<222> LOCATION: (3)..(1)
<223> OTHER INFORMATION: X stands for G or D
<220> FEATURE:
<221> NAME/KEY: misc_feature
<222> LOCATION: (3)..(3)
<223> OTHER INFORMATION: Xaa can be any naturally occurring amino acid

<400> SEQUENCE: 29

Xaa Thr Xaa Pro Thr Ser Phe Glu Val Asn Leu Ser Glu Glu Glu Lys
1               5                   10                  15

Met Glu Leu


<210> SEQ ID NO 30
<211> LENGTH: 29
<212> TYPE: PRT
<213> ORGANISM: Ehrlichia canis
<220> FEATURE:
<221> NAME/KEY: MISC_FEATURE
<222> LOCATION: (1)..(1)
<223> OTHER INFORMATION: X stands for C or  is absent
<220> FEATURE:
<221> NAME/KEY: MISC_FEATURE
<222> LOCATION: (14)..(14)
<223> OTHER INFORMATION: X stands for G or D
<220> FEATURE:
<221> NAME/KEY: MISC_FEATURE
<222> LOCATION: (25)..(25)
<223> OTHER INFORMATION: X stands for E or G

<400> SEQUENCE: 30

Xaa Thr Asn His Ile Glu His Asp Asp Tyr His Phe Thr Xaa Pro Thr
1               5                   10                  15

Ser Phe Glu Val Asn Leu Ser Glu Xaa Glu Lys Met Glu
            20                  25


<210> SEQ ID NO 31
<211> LENGTH: 27
<212> TYPE: PRT
<213> ORGANISM: Ehrlichia canis
<220> FEATURE:
<221> NAME/KEY: MISC_FEATURE
<222> LOCATION: (1)..(1)
<223> OTHER INFORMATION: X stands for C or is absent
<220> FEATURE:
<221> NAME/KEY: MISC_FEATURE
<222> LOCATION: (3)..(3)
<223> OTHER INFORMATION: X stands for G or D
<220> FEATURE:
<221> NAME/KEY: MISC_FEATURE
<222> LOCATION: (14)..(14)
<223> OTHER INFORMATION: X stands for E or G

<400> SEQUENCE: 31

Xaa Thr Xaa Pro Thr Ser Phe Glu Val Asn Leu Ser Glu Xaa Glu Lys
1               5                   10                  15

Met Glu Leu Gln Glu Val Ser Ser Ile Asp Ser
            20                  25
```

-continued

```
<210> SEQ ID NO 32
<211> LENGTH: 19
<212> TYPE: PRT
<213> ORGANISM: Ehrlichia canis
<220> FEATURE:
<221> NAME/KEY: MISC_FEATURE
<222> LOCATION: (1)..(1)
<223> OTHER INFORMATION: X stands for C or is absent
<220> FEATURE:
<221> NAME/KEY: MISC_FEATURE
<222> LOCATION: (3)..(3)
<223> OTHER INFORMATION: X stands for G or D
<220> FEATURE:
<221> NAME/KEY: MISC_FEATURE
<222> LOCATION: (14)..(14)
<223> OTHER INFORMATION: X stands for G or E

<400> SEQUENCE: 32

Xaa Thr Xaa Pro Thr Ser Phe Glu Val Asn Leu Ser Glu Xaa Glu Lys
1               5                   10                  15

Met Glu Leu


<210> SEQ ID NO 33
<211> LENGTH: 49
<212> TYPE: PRT
<213> ORGANISM: Ehrlichia canis
<220> FEATURE:
<221> NAME/KEY: MISC_FEATURE
<222> LOCATION: (1)..(1)
<223> OTHER INFORMATION: X stands for C or is absent
<220> FEATURE:
<221> NAME/KEY: MISC_FEATURE
<222> LOCATION: (4)..(4)
<223> OTHER INFORMATION: X stands for H or Q
<220> FEATURE:
<221> NAME/KEY: MISC_FEATURE
<222> LOCATION: (25)..(25)
<223> OTHER INFORMATION: X stands for D or G
<220> FEATURE:
<221> NAME/KEY: MISC_FEATURE
<222> LOCATION: (36)..(36)
<223> OTHER INFORMATION: X stands for E or G

<400> SEQUENCE: 33

Xaa Met Leu Xaa Val Gln Asn His Val Asp Gln His Thr Asn His Ile
1               5                   10                  15

Glu His Asp Asp Tyr His Phe Thr Xaa Pro Thr Ser Phe Glu Val Asn
            20                  25                  30

Leu Ser Glu Xaa Glu Lys Met Glu Leu Gln Glu Val Ser Ser Ile Asp
        35                  40                  45

Ser
```

*EHRLICHIA CANIS* DIVA (DIFFERENTIATE INFECTED FROM VACCINATED ANIMALS)

PRIORITY

This application claims the benefit of U.S. Ser. No. 60/984,019, which was filed on Oct. 31, 2007, and is incorporated herein by reference in its entirety.

Sequence Listing

This document incorporates by reference a sequence listing in text format. The text file "04_947DUS_SL.corrected for filing..txt" was created on Sep. 1, 2009, and is 85 KB.

BACKGROUND OF THE INVENTION

The *Ehrlichia* are obligate intracellular pathogens that infect circulating white blood cells in mammalian hosts. *Ehrlichia canis* can infect canines and humans and cause canine monocytic ehrlichiosis (CME) and human monocytic ehrlichiosis (HME), respectively. The canine disease is characterized by fever, lymphadenopathy, weight loss, and pancytopenia. In humans the disease is characterized by fever, headache, mylagia, and leukopenia. Early detection and treatment are important for treating both canine and human ehrlichiosis.

SUMMARY OF THE INVENTION

In one embodiment the invention provides a method of distinguishing between animals that have been (a) infected with *Ehrlichia canis*; and (b) animals that have not been infected with *E. canis* regardless of whether the animal has been vaccinated for *E. canis*. The method comprises (a) contacting a biological sample from an animal with one or more first purified polypeptides that do not specifically bind to antibodies that are a component of the animal's immune response to an *E. canis* vaccine; wherein the one or more first purified polypeptides have at least 95% identity to SEQ ID NOs:22-33 and wherein the one or more first purified *E. canis* polypeptides specifically bind an antibody that is specific for *E. canis*; and (b) detecting whether antibodies in the biological sample specifically bind to the one or more first purified *E. canis* polypeptides.

If antibodies in the biological sample specifically bind to the one or more first purified polypeptides, then the animal is infected with *E. canis*. The one or more first purified polypeptides can be about 15 to about 75 amino acids in length. The one or more first purified polypeptides can be linked to a heterologous amino acid sequence, an indicator reagent, an amino acid spacer, an amino acid linker, a signal sequence, a stop transfer sequence, a transmembrane domain, a protein purification ligand, or a combination thereof. The method can further comprise determining whether antibodies in the biological sample specifically bind to one or more second purified *E. canis* polypeptides that are an element of an *E. canis* vaccine. If antibodies in the biological sample specifically bind to the one or more first purified *E. canis* polypeptides and specifically bind to the one or more second purified *E. canis* polypeptides, then the animal has been infected with *E. canis* and the vaccination status for *E. canis* is unknown. If antibodies in the sample do not specifically bind to the one or more first purified *E. canis* polypeptides and specifically bind to the one or more second purified *E. canis* polypeptides, then the animal has not been infected with *E. canis* and has been vaccinated for *E. canis*. If antibodies in the sample do not specifically bind to the one or more first purified polypeptides and do not specifically bind to the one or more second purified polypeptides then the animal has not been vaccinated for *E. canis* and has not been infected by *E. canis*.

Yet another embodiment of the invention provides a method of determining an animal's vaccination and infection status for *E. canis*. The method comprises:

(a) contacting a biological sample from an animal with one or more first purified polypeptides that do not specifically bind to antibodies that are a component of the animal's immune response to an *E. canis* vaccine, wherein the one or more first purified polypeptides have at least 95% identity to SEQ ID NOs:22-33 and wherein the one or more first purified polypeptides specifically bind an antibody that is specific for *E. canis*, and one or more second purified polypeptides that specifically bind to an antibody that is a component of the animal's immune response to an *E. canis* vaccine; and (b) detecting whether antibodies in the biological sample specifically bind to the one or more first purified polypeptides and to the one or more second purified polypeptides.

If antibodies in the biological sample specifically bind to the one or more first purified *E. canis* polypeptides and specifically bind to the one or more second purified *E. canis* polypeptides, then the animal has been infected with *E. canis* and the vaccination status for *E. canis* is unknown. If antibodies in the sample do not specifically bind to the one or more first purified *E. canis* polypeptides and specifically bind to the one or more second purified *E. canis* polypeptides, then the animal has not been infected with *E. canis* and has been vaccinated for *E. canis*. If antibodies in the sample do not specifically bind to the one or more first purified polypeptides and do not specifically bind to the one or more second purified polypeptides then the animal has not been vaccinated for *E. canis* and has not been infected by *E. canis*. The one or more first purified polypeptides can be about 15 to about 75 amino acids in length. The one or more first purified polypeptides can be linked to a heterologous amino acid sequence, an indicator reagent, an amino acid spacer, an amino acid linker, a signal sequence, a stop transfer sequence, a transmembrane domain, a protein purification ligand, or a combination thereof.

Still another embodiment of the invention provides a method for determining the presence of an antibody or antigen-binding fragments thereof that are specific for *E. canis*, in a test sample. The method comprises:

(a) contacting the test sample with one or more purified polypeptides that have at least 95% identity to SEQ ID NOs:22-33 wherein the one or more purified polypeptides are about 15 to about 75 amino acids in length, and wherein the one or more first purified polypeptides specifically bind an antibody that is specific for *E. canis*, under conditions suitable for specific binding of the one or more purified polypeptides to the antibodies or antigen-binding fragments thereof, and (b) detecting the presence of specific binding of the one or more purified polypeptides to the antibodies or antigen-binding fragments thereof.

The presence of specific binding of the one or more purified polypeptides to the antibodies or antigen-binding fragments indicates the presence of the antibodies or antigen-binding fragments thereof specific for *E. canis* in the test sample. The one or more purified polypeptides can be linked to a heterologous amino acid sequence, an indicator reagent, an amino acid spacer, an amino acid linker, a signal sequence, a stop transfer sequence, a transmembrane domain, a protein purification ligand, or a combination thereof. The method can further comprise detecting the amount of specific binding. The one or more purified polypeptides can be immobilized to a solid support.

Even another embodiment of the invention provides a composition comprising:

(a) one or more purified polypeptides consisting of SEQ ID NO:22-33; or (b) one or more purified polypeptides having at least 95% identity to SEQ ID NOs:22-33 wherein the one or more purified polypeptides are about 15 to about 75 amino acids in length, and wherein the one or more purified polypeptides specifically bind an antibody that is specific for *E. canis;*

(c) SEQ ID NO:33, wherein the X at position 1 is absent or C, the X at position 4 is H or Q, the X at position 25 is D or G, and the X at position 36 is E or G;

(d) amino acids 1-27 of SEQ ID NO:33, wherein the X at position 1 is C, the X at position 4 is H, the X at position 25 is D or G;

(e) amino acids 13-41 of SEQ ID NO:33, wherein the X at position 25 is D or G, the X at position 36 is E or G; and a C is optionally present at the amino terminus;

(f) amino acids 24-49 of SEQ ID NO:33, wherein the X at position 25 is D or G, the X at position 36 is E or G, and a C is optionally present at the amino terminus;

(g) amino acids 1-27 of SEQ ID NO:33, wherein the X at position 1 is C or absent, and wherein the X at position 25 is D or G;

(h) amino acids 13-41 of SEQ ID NO:33, wherein the X at position 25 is D or G, the X at position 36 is E or G, and a C is optionally present at the amino terminus;

(i) amino acids 24-49 of SEQ ID NO:33, wherein the X at position 25 is D or G, the X at position 36 is E or G, and a C is optionally present at the amino terminus;

(j) amino acids 13-27 of SEQ ID NO:33, wherein the X at position 25 is D or G, and a C is optionally present at the amino terminus;

(k) amino acids 24-41 of SEQ ID NO:33, wherein the X at position 25 is D or G, the X at position 36 is E or G, and a C is optionally present at the amino terminus;

(l) amino acids 13-41 of SEQ ID NO:33, wherein the X at position 25 is D or G, the X at position 36 is E or G, and a C is optionally present at the amino terminus;

(m) amino acids 24-49 of SEQ ID NO:33, wherein the X at position 25 is D or G, the X at position 36 is E or G, and a C is optionally present at the amino terminus;

(n) amino acids 24-41 of SEQ ID NO:33, wherein the X at position 25 is D or G, the X at position 36 is E or G, and a C is optionally present at the amino terminus; or (o) combinations of (a)-(n).

The one or more purified polypeptides can be in a multimeric form. The one or more purified polypeptides can be linked to a heterologous protein, an indicator reagent, an amino acid spacer, an amino acid linker, a signal sequence, a stop transfer sequence, a transmembrane domain, a protein purification ligand, or a combination thereof.

Another embodiment of the invention provides a method of generating an immune response in an animal comprising administering one or more purified polypeptides having at least 95% identity to SEQ ID NOs:22-33 or a combination thereof to the animal, wherein the one or more purified polypeptides generate an immune response in the animal. The one or more purified polypeptides can be about 15 to about 75 amino acids in length. The one or more purified polypeptides can be in a multimeric form. The one or more purified polypeptides can be linked to a heterologous protein, an indicator reagent, an amino acid spacer, an amino acid linker, a signal sequence, a stop transfer sequence, a transmembrane domain, a protein purification ligand, or a combination thereof.

Still another embodiment of the invention provides a method for the prophylaxis, treatment, or amelioration of an *Ehrlichia canis* infection in an animal comprising administering to the animal:

(a) one or more purified polypeptides having at least 95% sequence identity to SEQ ID NOs:22-33, or a combination thereof; or (b) one or more nucleic acids encoding one or more purified polypeptides comprising SEQ ID NOs:22-33, or a combination thereof; or (c) one or more antibodies that specifically bind one or more purified polypeptides comprising SEQ ID NOs: 22-33, or a combination thereof;

whereby the *E. canis* infection is prevented, ameliorated, or treated.

Yet another embodiment of the invention provides a method of monitoring treatment of an *E. canis* infection in a patient comprising: (a) determining the level of anti-*E. canis* antibodies in a first sample from a patient prior to or in the early stages of a treatment for an *E. canis* infection by a method of claim 10; (b) determining the level of anti-*E. canis* antibodies in a second sample from the patient after treatment is effected by a method of claim 10; and (c) comparing the amount of anti-*E. canis* antibodies in the first sample with the amount of anti-*E. canis* antibodies in the second sample to assess a change and thereby monitor treatment.

BRIEF DESCRIPTION OF THE DRAWINGS

FIGS. 11A-C demonstrate detection of antibodies specific for *E. canis* using a polypeptide shown in SEQ ID NO: 10 in three dogs that have been vaccinated (RIBI+BCG adjuvant) for *E. canis* over a time course of infection.

DETAILED DESCRIPTION OF THE INVENTION

Figure 1:
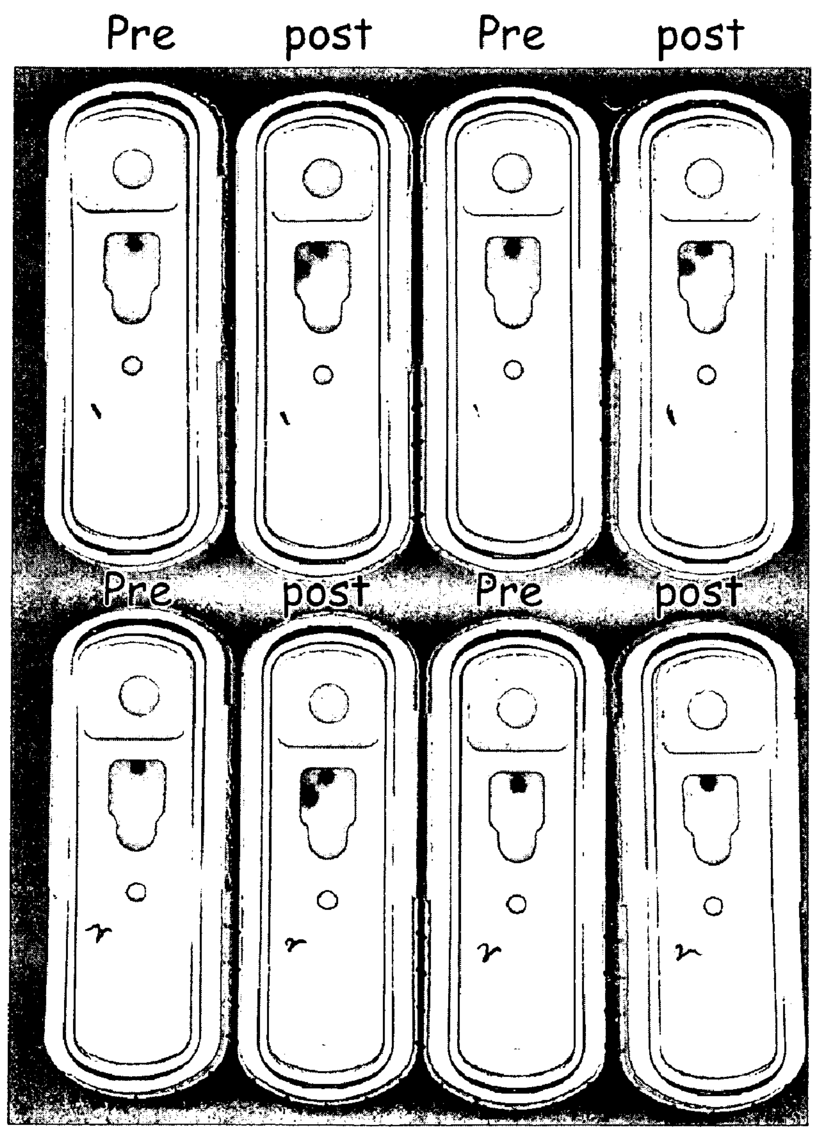
FIG. 1 shows SNAP® 3Dx® Assay (reversible flow chromatographic assay) evaluation of laboratory beagles. The SNAP® device used as described by manufacturer. "Pre" sample is from day 0. "Post" sample is from day 42. The *E. canis* positive spot became positive in all 4 dogs for the day 42 sample. Similar results were observed for the day 70 sample.

*Ehrlichia canis* antigens are disclosed that can be used to differentiate *E. canis* naturally-infected animals from animals that have been vaccinated against with *E. canis*. "Vaccinated" means the administration of a vaccine composition that can prevent or ameliorate the effects of infection by a pathogen by establishing or improving immunity to the pathogen. Vaccine compositions can comprise dead, inactivated or attenuated pathogens or purified products or portions of the pathogen. Vaccination is not necessarily 100% effective.

Before describing the present invention in detail, a number of terms will be defined. As used herein, the singular forms "a," "an", and "the" include plural referents unless the context clearly dictates otherwise.

As used herein, the term "polypeptide" refers to a compound of a single chain or a complex of two or more chains of amino acid residues linked by peptide bonds. The chain(s) may be of any length and can comprise a fusion protein. Although "protein" is often used in reference to relatively large polypeptides, and "peptide" is often used in reference to small polypeptides, usage of these terms in the art overlaps and varies. The term "polypeptide" as used herein thus refers interchangeably to peptides, polypeptides, proteins, or fusion proteins unless otherwise noted. The term "amino acid" refers to a monomeric unit of a peptide, polypeptide or protein. The term "polypeptides" can refer to one or more of one type of polypeptide (a set of polypeptides). "Polypeptides" can also refer to mixtures of two or more different types of polypeptides (a mixture of polypeptides). The terms "polypeptides" or "polypeptide" can each also mean "one or more polypeptides."

Polypeptides of the invention can be "isolated." An isolated polypeptide is a polypeptide that is not immediately contiguous with one or both of the amino and carboxy flanking amino acid sequences that it is naturally associated with. In particular, "an isolated polypeptide shown in SEQ ID NOs:22-33" means that the polypeptide is not immediately contiguous with one or both of the amino and carboxy flanking amino acid sequences that it is naturally associated with (where the polypeptide is a naturally occurring polypeptide) in an *E. canis* protein molecule.

As used herein, "antigen" as used herein refers to a molecule against which a subject can initiate a humoral and/or cellular immune response. Antigens can be any type of biologic molecule including, for example, simple intermediary metabolites, sugars, lipids, and hormones as well as macromolecules such as complex carbohydrates, phospholipids, nucleic acids and proteins. In the compositions and methods of the invention, an antigen can be a polypeptide, e.g., one comprising at least about six or more amino acids.

As used herein, a "derivative" of an *E. canis* antigen polypeptide, or an antigen or polypeptide that is "derived from" an *E. canis* antigen or polypeptide, refers to a antigen or polypeptide in which the native form has been purified, modified or altered. Such modifications include, but are not limited to: amino acid substitutions, modifications, additions or deletions; alterations in the pattern of lipidation, glycosylation or phosphorylation; reactions of free amino, carboxyl, or hydroxyl side groups of the amino acid residues present in the polypeptide with other organic and non-organic molecules; and other modifications, any of which may result in changes in primary, secondary or tertiary structure.

A "biological sample" is any sample from an animal that is expected to contain immunoglobulins. For example, a biological sample can be plasma, blood, serum, saliva, urine, feces, wound exudate, cerebrospinal fluid (CSF), semen, sputum, as well as tissue extracts, and cell extracts. In one embodiment of the invention a test sample can be obtained from an animal such as a horse, dog, cow, llama, sheep, goat, deer, elk, rodent or any other animal. A human is considered to be an animal herein. These examples are not to be construed as limiting the sample types or animals that are applicable to the present invention.

An "infection," such as in an *E. canis* infection, means that an animal has been exposed to *E. canis*, regardless of whether the animal exhibits clinical symptoms of *E. canis*. A natural infection refers to an exposure that occurs as a result of one of the natural transmission methods for *E. canis*, such as transmission by ticks. An infection does not include an exposure to *E. canis* through vaccination.

A "polypeptide or antigen that is not an element of an *E. canis* vaccine" is any *E. canis* polypeptide or antigen that is not present in a particular *E. canis* vaccine or vaccines. A "polypeptide or antigen that is not an element of an *E. canis* vaccine" is also any *E. canis* polypeptide or antigen that is not an immunogenically active portion of an *E. canis* vaccine. That is, the polypeptide or antigen may be present in the vaccine, but an immune response against the polypeptide or antigen (e.g., the generation of antibodies that specifically bind to the polypeptide or antigen) is not generated in response to administration of the *E. canis* vaccine. Elements of the vaccine(s) can be portions of a subunit vaccine that includes less than the entire bacterium; these portions can be chemically synthesized or expressed recombinantly before becoming part of the vaccine, and these portions can be encoded by one or more vectors that express an immunogenic composition in vivo.

An "antibody that is a component of an animal's immune response to an *E. canis* vaccine" refers to an antibody that is elicited as the result of a vaccination with an *E. canis* vaccine. These antibodies can be identical to or similar to antibodies elicited as the result of a natural *E. canis* infection. These antibodies will be maintained at a sufficient titer and so as to provide a protective and neutralizing effect against the bacteria. A successful vaccination produces a measurable level of the antibody (or antibodies) that is elicited by a component of the *E. canis* vaccine. Examples of *E. canis* antigens that elicit antibodies that can be a component of an animal's immune response to an *E. canis* vaccine are p28-1, p28-2, p28-3, p28-4, p28-5, p28-6, p28-7, p28-8, p28-9 (see, U.S. Pat. Nos.

6,660,269; 6,458,942; 6,403,780; 6,392,023), proA, ProB, mmpA, cytochrome oxidase (see, U.S. Pat. Publ. 20040170972), p43 (see, U.S. Pat. No. 6,355,777), which is the N-terminal portion of p153, a glycoprotein (see, U.S. Pat. Publ. 2004/0121433), p153, and p30-1, p30-2, p30-3, p30-4, p30-5, p30-6, p30-7, p30-8, p30-9, p30-10, p30-11, p30-12, p30-13, p30-14, p30-15, p30-16, p30-17, p30-18, p30-19, p30-20 (Ohashi et al. 2001, Infection and Immunity 69(4): 2083-91).

An immune response is the development in an organism of a cellular and/or antibody mediated immune response to an antigen such as a polypeptide. Usually such a response includes, but is not limited to, one or more of the following: production of antibodies, B cells, helper T cells, suppressor T cells, and/or cytotoxic T cells. An immune response can be detected using any of several assays known to those with skill in the art.

Polypeptides of the Invention

Biological samples from animals that have been vaccinated against *E. canis* have the potential for producing a positive result in a test for *E. canis* infection due to the presence of antibodies produced in response to the vaccine. In one aspect, the invention provides a method of distinguishing between animals that have been infected with *E. canis* and those that have not been infected with *E. canis*, regardless of whether the animal has been vaccinated for *E. canis*. Methods include contacting a biological sample from the animal with an antigen derived from *E. canis* that does not specifically bind to an antibody that is a component of the animal's antibody response to a particular *E. canis* vaccine, but that does specifically bind to an antibody that is generated in response to infection by *E. canis*.

The development of *E. canis* antibodies in an animal against a vaccine is dependent upon the particular vaccine used to vaccinate the animal. The difference in the immune response between animals that are vaccinated against *E. canis* and animals that are naturally or experimentally infected with *E. canis* provides a means for determining whether an animal is naturally or experimentally infected with *E. canis*, regardless of whether the animal has been vaccinated for *E. canis*. Therefore, using the methods of the invention, animals that have been infected with *E. canis* can be distinguished from animals that have not been infected with *E. canis* and/or have been vaccinated against *E. canis*. Antigens of the invention, their immunodominant regions, and epitopes can be used in the methods of the invention. These compositions can be referred to as *E. canis* DIVA antigens (Differentiate Infected from Vaccinated Animals). An *E. canis* DIVA antigen induces an immune response, e.g., the production of specific antibodies, in an animal that is different from the immune response induced in the animal by a particular *E. canis* vaccine.

Accordingly, detection of specific binding between an *E. canis* DIVA antigen and an antibody that is not a component of an animal's immune response to a particular vaccine can indicate a natural or experimental *E. canis* infection. The absence of such binding can indicate the absence of *E. canis* infection. In addition, a second, separate antigen, such as an *E. canis* antigen that specifically binds an antibody that is a component of an animal's immune response to a particular *E. canis* vaccine, can be used to detect antibodies produced in response to vaccination (herein referred to as "an *E. canis* vaccine antigen"). An *E. canis* vaccine antigen not only specifically binds an antibody that is a component of an animal's immune response to a particular *E. canis* vaccine, but can also specifically bind to antibodies that are a component of an animal's immune response to infection by *E. canis*. If an antibody specific for an *E. canis* vaccine antigen is detected, then the animal has been vaccinated and/or infected. The detection of neither antibody indicates no infection and no vaccination. As such, various combinations of separate capture reagents can lead to a determination of the vaccination and/or infection status of the test subject.

In one aspect, a method of the invention includes contacting a biological sample from an animal with an antigen that is a part of the *E. canis* bacteria, but is not an element of a particular *E. canis* vaccine. In another aspect, a method of the invention includes contacting a biological sample from an animal with an antigen that is present in or part of *E. canis* bacteria and an *E. canis* vaccine, wherein an immune response against the antigen (e.g., the generation of antibodies that specifically bind to the antigen) is generated in response to infection with the *E. canis* bacteria, but not in response to administration of the *E. canis* vaccine. In another aspect, a biological sample from an animal is analyzed to detect the presence or absence of antibodies specific for an *E. canis* DIVA antigen, and the presence or absence of antibodies specific for an *E. canis* vaccine antigen. It is then determined that the animal has not been infected and has not been or vaccinated by determining the absence of such antibodies.

In one aspect of the invention, a DIVA antigen is not an element of an *E. canis* vaccine. In another aspect of the invention, a DIVA antigen is part of an *E. canis* vaccine, but an immune response (e.g., the generation of an antibody that specifically binds the DIVA antigen) is not generated in response to administration of the *E. canis* vaccine. The vaccination or infection status of an animal can be determined by detecting whether antibodies in the sample specifically bind to one or more *E. canis* vaccine antigens and whether antibodies in the sample specifically bind to one or more DIVA antigens. If antibodies in the sample specifically bind to one or more of the vaccine antigens and specifically bind to one or more of the DIVA antigens, then the animal is infected with *E. canis* and the vaccination status of the animal is unknown. If antibodies in the sample specifically bind to one or more of the *E. canis* vaccine antigens and do not specifically bind to one or more of the DIVA antigens, then the animal is vaccinated for *E. canis* and is not infected with *E. canis*. If antibodies in the sample do not specifically bind to one or more of the *E. canis* vaccine antigens and do not specifically bind to one or more of the DIVA antigens, then the animal is not infected with *E. canis* and is not vaccinated for *E. canis*.

One aspect of the invention provides a method of distinguishing between animals that have been (a) infected with *Ehrlichia canis*; and (b) animals that have not been infected with *E. canis* regardless of their *E. canis* vaccine status. The method comprises contacting a biological sample from an animal with a first purified *E. canis* polypeptide that does not substantially specifically bind to antibodies that are a component of the animal's immune response to an *E. canis* vaccine; wherein the first purified *E. canis* polypeptide comprises SEQ ID NOs:22-33 or combinations thereof and detecting whether antibodies in the sample specifically bind to the first purified *E. canis* polypeptide. If antibodies in the sample specifically bind to the first purified *E. canis* polypeptide, then the animal is infected with *E. canis*; and if antibodies in the sample do not substantially specifically bind to the first purified *E. canis* polypeptide, then the animal is not infected with *E. canis*.

The method can further comprise determining whether antibodies in the sample specifically bind to a second purified *E. canis* polypeptide that comprises an *E. canis* vaccine antigen. If antibodies in the sample specifically bind to one or more of the *E. canis* vaccine antigens and specifically bind to one or more of the DIVA antigens, then the animal is infected with *E. canis* and the vaccination status of the animal is unknown. If antibodies in the sample specifically bind to one or more of the *E. canis* vaccine antigens and do not specifically bind to one or more of the DIVA antigens, then the animal is vaccinated for *E. canis* and is not infected with *E. canis*. If antibodies in the sample do not specifically bind to one or more of the *E. canis* vaccine antigens and do not specifically bind to one or more of the DIVA antigens, then the animal is not infected with *E. canis* and is not vaccinated for *E. canis*. In one embodiment of the invention antibodies in test samples do not substantially specifically bind to DIVA antigens and/or *E. canis* vaccine antigens. Substantially no specific binding is an amount of binding that would be considered a negative result by one of skill in the art.

One aspect of the invention provides a method of determining an animal's vaccination and infection status for *E. canis*. The method comprises:

(a) contacting a biological sample from an animal with a first purified polypeptide that does not substantially specifically bind to antibodies that are a component of the animal's immune response to an *E. canis* vaccine, wherein the first purified polypeptide comprises SEQ ID NOs:22-33 or combinations thereof, and a second polypeptide that specifically binds to an antibody that is a component of the animal's immune response to an *E. canis* vaccine;

(b) detecting whether antibodies in the sample specifically bind to the first and second purified polypeptides;

wherein if antibodies in the biological sample specifically bind to the one or more first purified *E. canis* polypeptides and specifically bind to the one or more second purified *E. canis* polypeptides, then the animal has been infected with *E. canis* and the vaccination status for *E. canis* is unknown; wherein if antibodies in the sample do not specifically bind to the one or more first purified *E. canis* polypeptides and specifically bind to the one or more second purified *E. canis* polypeptides, then the animal has not been infected with *E. canis* and has been vaccinated for *E. canis*; and wherein if antibodies in the sample do not specifically bind to the one or more first purified polypeptides and do not specifically bind to the one or more second purified polypeptides then the animal has not been vaccinated for *E. canis* and has not been infected by *E. canis*.

Table 1 demonstrates the infection and/or vaccination status of animals that can be determined with *E. canis* DIVA antigens and *E. canis* vaccine antigens. "Not Done" in Table 1 means that a particular test was not completed and therefore no result is available. For example if a biological sample from an animal is tested with an *E. canis* DIVA antigen and the result is positive and no test is completed with an *E. canis* vaccine antigen, then the animal's status would be infected, but vaccination status unknown.

TABLE 1

| Infection/Vaccination Status of Animal | Result with *E. canis* DIVA antigen | Result with *E. canis* vaccine antigen* |
|---|---|---|
| Infected, vaccination status unknown | Positive | Not Done |
| Infected, vaccination status unknown | Positive | Positive |
| Vaccinated, not infected | Negative | Positive |
| Vaccinated and/or infected | Not Done | Positive |
| Not infected, not vaccinated | Negative | Negative |
| Not infected, vaccination status unknown | Negative | Not Done |
| Not vaccinated, not infected | Not Done | Negative |

*An *E. canis* vaccine antigen specifically binds an antibody that is a component of an animal's immune response to a particular *E. canis* vaccine. An *E. canis* vaccine antigen not only specifically binds an antibody that is a component of an animal's immune response to a particular *E. canis* vaccine, but can also bind to antibodies that are a component of an animal's immune response to infection by *E. canis*.

Another aspect of the invention provides a method for determining the presence or absence of an antibody or antigen-binding fragment thereof, in a test sample, wherein the antibody or antigen-binding fragment thereof specifically binds to a purified polypeptide consisting of SEQ ID NOs:10, 22-33 or combinations thereof. The method comprises contacting the test sample with a purified polypeptide comprising SEQ ID NO:10, 22-33 or combinations thereof under conditions suitable for specific binding of the purified polypeptide to the antibody or antigen-binding fragment thereof, and detecting the presence or absence of specific binding. The presence of specific binding indicates the presence of the antibody or antigen-binding fragment thereof, and the absence of specific binding indicates the absence the antibody or antigen-binding fragment thereof.

Vaccines may not be completely effective at preventing or ameliorating infection. Therefore, it is desirable to have a method to determine if a vaccinated animal has become infected despite the vaccination. SEQ ID NOs:10, 22-33 do not detect anti-*E. canis* antibodies in dogs that have been vaccinated for *E. canis* and that are not infected with *E. canis*. SEQ ID NOs:10, 22-33 can be used to detect *E. canis* infection in dogs that have received or have not received an *E. canis* vaccine. In one embodiment of the invention, the animal becomes infected with *E. canis* after receiving an *E. canis* vaccine and detection of *E. canis* is still possible.

Another aspect of the invention comprises a composition comprising or consisting of one or more purified polypeptides comprising or consisting of SEQ ID NOs:10, 22-33 or combinations thereof. A polypeptide of the invention can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide, etc., has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure. A purified polypeptide does not include unpurified or semi-purified cell extracts or mixtures of polypeptides that are less than 70% pure.

One embodiment of the invention provides a purified polypeptide comprising SEQ ID NOs:22-33, wherein the polypeptide consists of less than about 50, 45, 40, 35, 30, 26, 25, 24, 23, 22, 21, 20, 19, 18, 17, 16, 15, 14, 13, 12, 11, 10, 9, 8, 7, 6 or less (or any range between 50 and 6) contiguous naturally occurring *Ehrlichia canis* amino acids (i.e, the purified polypeptide does not encompass the entire naturally occurring *Ehrlichia canis* polypeptide). Naturally occurring *Ehrlichia canis* amino acids are any polypeptides naturally produced by an *Ehrlichia canis* organism. In one embodiment of the invention a purified polypeptide comprises SEQ ID NOs:22-33, wherein the polypeptide comprises more than about 6, 7, 8, 9, 10, 11, 12, 13, 14, 15, 16, 17, 18, 19, 20, 21, 22, 23, 24, 25, 26, 30, 35, 40, 50, 60, 70, 80, 90, 100, or more contiguous naturally occurring *Ehrlichia canis* amino acids (or any range between about 6 and 100 amino acids).

The fact that polypeptides SEQ ID NOs:22-33 are smaller than a full length *Ehrlichia canis* polypeptide is important because smaller polypeptides can have greater specificity and/or sensitivity than full length polypeptides in detection assays. Additionally, these smaller polypeptides can be less expensive to manufacture, and may be obtained at greater purity than the full length polypeptide.

One embodiment of the invention provides a purified polypeptide that is less than about 50, 45, 40, 35, 30, 26, 25, 24, 23, 22, 21, 20, 19, 18, 17, 16, 15, 14, 13, 12, 11, 10, 9, 8, 7 or 6 contiguous naturally *Ehrlichia canis* amino acids and greater than about 6, 7, 8, 9, 10, 11, 12, 13, 14, 15, 16, 17, 18, 19, 20, 21, 22, 23, 24, 25, 26, 30, 35, 40, 50, 60, 70, 80, 90, or 100 contiguous amino acids of SEQ ID NOs:22-33 (or any range between 6 and 100 amino acids). Therefore, a polypeptide of the invention can be, for example, about 15 to about 30; about 15 to about 50; or about 15 to about 100 amino acids in length.

Variant polypeptides are at least about 79%, 80%, 81, 82, 83, 84, 85, 86, 87, 88, 89, 90, 91, 92, 93, 94, 95, 96, 97, 98, 99% or more identical to the polypeptide sequences shown in SEQ ID NOs:22-33 and are also polypeptides of the invention. Variant polypeptides have one or more conservative amino acid variations or other minor modifications and retain biological activity, i.e., are biologically functional equivalents. A biologically active equivalent has substantially equivalent function when compared to the corresponding wild-type polypeptide. In one embodiment of the invention a polypeptide has about 1, 2, 3, 4, 5, 10, 20 or less conservative amino acid substitutions.

These polypeptides may have additional amino acid residues beyond those in SEQ ID NOs:22-33. That is, the polypeptides may have additional amino acids residues added onto the 5' or 3' end of the polypeptides, while the sequence identity along 15, 16, 17, 18, 19, 20, 21, 22, 23, 24, 25, 26, 27, 28, 29, 30, 35, 40, 45, or 48 contiguous amino acids (depending on the length of the specific SEQ ID NO) of SEQ ID NOs:22-33 is at least about 95%. The additional amino acids added onto the 5' or 3' end of the polypeptides are not considered to affect the sequence identity percentage. The additional amino acids can be those that naturally occur or can be non-naturally occurring amino acids. The polypeptides can be, for example, from about 15 to about 50 or about 75 amino acids in length.

Variant polypeptides have one or more conservative amino acid substitutions, deletions additions or other minor modifications and retain biological activity, i.e., are biologically functional equivalents. A biologically active equivalent has substantially equivalent function when compared to the corresponding wild-type polypeptide.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.,* 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide or polypeptide and that gaps in identity of up to 5% of the total number of nucleotides or amino acids in the reference polynucleotide are allowed.

Variant polypeptides can generally be identified by modifying one of the polypeptide sequences of the invention, and evaluating the properties of the modified polypeptide to determine if it is a biological equivalent. A variant is a biological equivalent if it reacts substantially the same as a polypeptide of the invention in an assay such as an immunohistochemical assay, an enzyme-linked immunosorbent Assay (ELISA), a radioimmunoassay (RIA), immunoenzyme assay or a western blot assay, e.g. has 90-110% of the activity of the original polypeptide. In one embodiment, the assay is a competition assay wherein the biologically equivalent polypeptide is capable of reducing binding of the polypeptide of the invention to a corresponding reactive antigen or antibody by about 80, 95, 99, or 100%. An antibody that specifically binds a corresponding wild-type polypeptide also specifically binds the variant polypeptide.

A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A polypeptide of the invention can further comprise a signal (or leader) sequence that co-translationally or post-translationally directs transfer of the protein. The polypeptide can also comprise a linker or other sequence for ease of synthesis, purification or identification of the polypeptide (e.g., poly-His), or to enhance binding of the polypeptide to a solid support. For example, a polypeptide can be conjugated to an immunoglobulin Fc region or bovine serum albumin.

A polypeptide can be covalently or non-covalently linked to an amino acid sequence to which the polypeptide is not normally associated with in nature, i.e., a heterologous amino acid sequence. A heterologous amino acid sequence can be from a non-*E. canis* organism, a synthetic sequence, or an *E. canis* sequence not located at the carboxy or amino terminus of a polypeptide of the invention in nature. Additionally, a polypeptide can be covalently or non-covalently linked to compounds or molecules other than amino acids such as indicator reagents. A polypeptide can be covalently or non-covalently linked to an indicator reagent, an amino acid spacer, an amino acid linker, a signal sequence, a stop transfer sequence, a transmembrane domain, a protein purification ligand, or a combination thereof. A polypeptide can also be linked to a moiety (i.e., a functional group that can be a polypeptide or other compound) that enhances an immune response (e.g., cytokines such as IL-2), a moiety that facilitates purification (e.g., affinity tags such as a six-histidine tag, trpE, glutathione, maltose binding protein), or a moiety that facilitates polypeptide stability (e.g., polyethylene glycol; amino terminus protecting groups such as acetyl, propyl, succinyl, benzyl, benzyloxycarbonyl or t-butyloxycarbonyl; carboxyl terminus protecting groups such as amide, methylamide, and ethylamide). In one embodiment of the invention a protein purification ligand can be one or more C amino acid residues at, for example, the amino terminus or carboxy terminus or both termini of a polypeptide of the invention. An amino acid spacer is a sequence of amino acids that are not associated with a polypeptide of the invention in nature. An amino acid spacer can comprise about 1, 5, 10, 20, 100, or 1,000 amino acids.

If desired, a polypeptide of the invention can be part of a fusion protein, which can also contain other amino acid sequences, such as amino acid linkers, amino acid spacers, signal sequences, TMR stop transfer sequences, transmembrane domains, as well as ligands useful in protein purification, such as glutathione-S-transferase, histidine tag, and Staphylococcal protein A, or combinations thereof. More than one polypeptide of the invention can be present in a fusion protein. Fragments of polypeptides of the invention can be present in a fusion protein of the invention. A polypeptide of the invention can be operably linked to non-*Ehrlichia canis* proteins or non-*Ehrlichia canis* p16 proteins to form fusion proteins. A fusion protein of the invention can comprise one or more polypeptides shown in SEQ ID NO: 2, 4, 6, 8, 10, 12, 14, 15, 16, 17, 18, 19, 20, 21, 22, 23, 24, 25, 26, 27, 28, 29, 30, 31, 32, 33 or fragments thereof, or combinations thereof. A fusion protein does not occur in nature. The term "operably linked" means that the polypeptide of the invention and the other polypeptides are fused in-frame to each other either to the N-terminus or C-terminus of the polypeptide of the invention.

Polypeptides of the invention can be in a multimeric form. That is, a polypeptide can comprise one or more copies of SEQ ID NOs: 2, 4, 6, 8, 10, 12, 14, 15, 16, 17, 18, 19, 20, 21, 22, 23, 24, 25, 26, 27, 28, 29, 30, 31, 32, 33 or a combination thereof. A multimeric polypeptide can be a multiple antigen peptide (MAP). See e.g., Tam, J. Immunol. Methods, 196:17-32 (1996).

Polypeptides of the invention can comprise an antigen that is recognized by an antibody specific for *E. canis*. The antigen can comprise one or more epitopes (i.e., antigenic determinants). An epitope can be a linear epitope, sequential epitope or a conformational epitope. Epitopes within a polypeptide of the invention can be identified by several methods. See, e.g., U.S. Pat. No. 4,554,101; Jameson & Wolf, *CABIOS* 4:181-186 (1988). For example, a polypeptide of the invention can be isolated and screened. A series of short peptides, which together span an entire polypeptide sequence, can be prepared by proteolytic cleavage. By starting with, for example, 30-mer polypeptide fragments (or smaller fragments), each fragment can be tested for the presence of epitopes recognized in an ELISA. For example, in an ELISA assay an *E. canis* polypeptide, such as a 30-mer polypeptide fragment, is attached to a solid support, such as the wells of a plastic multi-well plate. A population of antibodies are labeled, added to the solid support and allowed to bind to the unlabeled antigen, under conditions where non-specific absorption is blocked, and any unbound antibody and other proteins are washed away. Antibody binding is detected by, for example, a reaction that converts a colorless substrate into a colored reaction product. Progressively smaller and overlapping fragments can then be tested from an identified 30-mer to map the epitope of interest.

In one embodiment of the invention, a DIVA antigen comprises an immunodominant epitope or region. That is, an epitope or region that more frequently elicits and binds to antibodies in a population thereof when compared with other epitopes. An antigen can have one or more immunodominant epitopes. Immunodominant epitopes can be mapped on, for example, a polypeptide after the polypeptide has been administered to an animal or prior to such administration. See e.g., U.S. Pat. Publ. 2004/0209324.

A polypeptide of the invention can be produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system. A polypeptide can also be chemically synthesized or obtained from *E. canis* cells.

An immunogenic polypeptide of the invention can comprise an amino acid sequence shown in SEQ ID NOs: 2, 4, 6, 8, 10, 12, 14, 15, 16, 17, 18, 19, 20, 21, 22, 23, 24, 25, 26, 27, 28, 29, 30, 31, 32, 33 or fragments thereof. An immunogenic polypeptide can elicit antibodies or other immune responses (e.g., T-cell responses of the immune system) that recognize epitopes of a polypeptide having SEQ ID NOs: 2, 4, 6, 8, 10, 12, 14, 15, 16, 17, 18, 19, 20, 21, 22, 23, 24, 25, 26, 27, 28, 29, 30, 31, 32, or 33. An immunogenic polypeptide of the invention can also be a fragment of a polypeptide that has an amino acid sequence shown in SEQ ID NOs: 2, 4, 6, 8, 10, 12, 14, 15, 16, 17, 18, 19, 20, 21, 22, 23, 24, 25, 26, 27, 28, 29, 30, 31, 32, or 33. An immunogenic polypeptide fragment of the invention can be about 50, 45, 40, 35, 30, 26, 25, 24, 23, 22, 21, 20, 19, 18, 17, 16, 15, 14, 13, 12, 11, 10, 9, 8, 7, 6 or less (or any range between about 50 and about 6) amino acids in length. An immunogenic polypeptide fragment of the invention can be more than about 6, 7, 8, 9, 10, 11, 12, 13, 14, 15, 16, 17, 18, 19, 20, 21, 22, 23, 24, 25, 26, 30, 35, 40, 50, 60, 70, 80, 90, 100, or more amino acids in length (or any range between about 6 and about 100 amino acids).

Antibodies specific for *E. canis* can be detected in biological fluids or tissues by any method known in the art using the polypeptides of the invention. The simplest methods generally are immunoassay methods. One such method is a competition-based method wherein serum samples are preincubated with an *E. canis* antigen that is not an element of an *E. canis* vaccine (e.g., an *E. canis* DIVA antigen), and then added to a solid phase, such a microtiter plate, having an immobilized monoclonal antibody specific for the *E. canis* DIVA antigen. Antibodies specific for the *E. canis* DIVA antigen in the sample will prevent the *E. canis* DIVA antigen from binding to the immobilized antibody. Detection of any binding of the *E. canis* DIVA antigen to the immobilized antibody can be determined by adding a second binding partner for the *E. canis* antigen, either directly labeled or capable of becoming labeled through binding to another binding partner having a label. A positive sample, i.e. a sample having antibodies specific for an *E. canis* DIVA antigen, is associated with a decrease in signal from the label.

In one particular embodiment, antibodies to an *E. canis* DIVA antigen in a biological sample can be detected by contacting the sample with an *E. canis* DIVA antigen and adding the sample to microtiter plate coated with an anti- DIVA antigen monoclonal antibody. Binding of the DIVA antigen to the microtiter plate can be detected by adding a rabbit polyclonal antibody against the DIVA antigen and adding an HRP-conjugated donkey anti-rabbit polyclonal antibody. Antibodies in the sample will prevent the binding of the DIVA antigen to the immobilized antibody, thereby causing a decrease in signal.

Another method for detecting antibodies specific for an *E. canis* DIVA antigen is a sandwich assay where a biological sample suspected of containing an antibody specific for an *E. canis* DIVA antigen is contacted with an immobilized *E. canis* DIVA antigen to form an immunological complex. The presence of an antibody specific for an *E. canis* DIVA antigen is determined by the detection of the binding of a labeled binding partner for the *E. canis* antibody, such as a second antibody.

In one aspect of the invention, *E. canis* DIVA antigens can be immobilized on a suitable solid support. A biological sample is brought into contact with the *E. canis* DIVA antigen, to which the anti-*E. canis* antibodies bind, if such antibodies are present in the sample. The binding can be detected by any suitable means, e.g., enzymes, radionuclides, particulates or fluorescent labels. In a suitable embodiment, the detection reagent can be associated with a protein that is the same or similar to that which is used to capture anti-*E. canis* antibodies (if present). In one particular embodiment, antibodies to *E. canis* can be detected by immobilizing an *E. canis* antigen on a solid support. Biological samples can be contacted with the solid support and, following the removal of unbound sample, binding of the *E. canis* antibodies to the antigen can be accomplished with, for example, a labeled IgG antibody.

DIVA antigens of the invention can also comprise mimitopes of DIVA antigens of the invention. A mimitope is a random peptide epitope that mimics a natural antigenic epitope during epitope presentation. Random peptide epitopes can be identified by generating or selecting a library of random peptide epitopes. The library is contacted with an antibody. Mimitopes are identified that are specifically immunoreactive with the antibody. Random peptide libraries can, for example, be displayed on phage or generated as combinatorial libraries.

*E. canis* DIVA antigens, e.g., polypeptides, can be natural, i.e., isolated from a natural source, or can be synthetic (i.e., chemically synthesized or recombinantly produced using genetic engineering techniques). Natural proteins can be isolated from the whole bacterium by conventional techniques, such as affinity chromatography. Polyclonal or monoclonal antibodies can be used to prepare a suitable affinity column by well-known techniques.

Proteins that are immunologically cross-reactive with a natural *E. canis* protein can be chemically synthesized. For example, polypeptides having fewer than about 100 amino acids, more usually fewer than about 80 amino acids, and typically fewer than about 50 amino acids, can be synthesized by the well-known Merrifield solid-phase synthesis method where amino acids are sequentially added to a growing chain. Merrifield, 1963, J. Am. Chem. Soc., 85:2149-2156). Recombinant proteins can also be used. These proteins can be produced by expression in cultured cells of recombinant DNA molecules encoding a desired portion of the *E. canis* genome. The portion of the *E. canis* genome can itself be natural or synthetic, with natural genes obtainable from the isolated bacterium by conventional techniques.

*E. canis* Polynucleotides

Polynucleotides of the invention contain less than an entire microbial genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. A nucleic acid molecule existing among hundreds to millions of other nucleic acid molecules within, for example, cDNA or genomic libraries, or gel slices containing a genomic DNA restriction digest are not to be considered an isolated polynucleotide. The polynucleotides of the invention encode the polypeptides of the invention described above. In one embodiment of the invention the polynucleotides encode polypeptides shown in SEQ ID NOs:2, 4, 6, 8, 10, 12, 14, 15, 16, 17, 18, 19, 20, 21, 22, 23, 24, 25, 26, 27, 28, 29, 30, 31, 32, 33, fragments thereof, or combinations thereof. Polynucleotides of the invention can consist of less than about 200, 120, 100, 90, 75, 60, 57, 54, 45 (or any range between 200 and 45) contiguous, naturally occurring *Ehrlichia canis* polynucleotides. Polynucleotides of the invention can consist of greater than about 45, 54, 57, 60, 75, 90, 100, 120, 150, 200, (or any range between 45 and 200), or more contiguous, naturally occurring *Ehrlichia canis* polynucleotides. The purified polynucleotides can comprise additional heterologous nucleotides (that is, nucleotides that are not from *Ehrlichia canis*) and even additional *Ehrlichia canis* amino acids as long as they do not naturally occur contiguously with *Ehrlichia canis* p16 polynucleotides or other polynucleotides of the invention. Polynucleotides of the invention can comprise other nucleotide sequences, such as sequences coding for linkers, signal sequences, TMR stop transfer sequences, transmembrane domains, or ligands useful in protein purification such as glutathione-S-transferase, histidine tag, and Staphylococcal protein A.

Polynucleotides of the invention can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules. A nucleic acid molecule existing among hundreds to millions of other nucleic acid molecules within, for example, cDNA or genomic libraries, or gel slices containing a genomic DNA restriction digest are not to be considered an isolated polynucleotide. The complete nucleotide sequence for *E. canis* is available from, e.g., GenBank as accession number NCBI: NZ_AAEJ01000001.

Polynucleotides of the invention can also comprise fragments that encode immunogenic polypeptides. Polynucleotides of the invention can encode full-length polypeptides, polypeptide fragments, and variant or fusion polypeptides.

Degenerate nucleotide sequences encoding polypeptides of the invention, as well as homologous nucleotide sequences that are at least about 80, or about 90, 96, 98, or 99% identical to the polynucleotide sequences of the invention and the complements thereof are also polynucleotides of the invention. Percent sequence identity can be calculated as described in the "Polypeptides" section. Degenerate nucleotide sequences are polynucleotides that encode a polypeptide of the invention or fragments thereof, but differ in nucleic acid sequence from the wild-type polynucleotide sequence, due to the degeneracy of the genetic code. Complementary DNA (cDNA) molecules, species homologs, and variants of *E. canis* polynucleotides that encode biologically functional *E. canis* polypeptides also are *E. canis* polynucleotides. Polynucleotides of the invention can be isolated from nucleic acid sequences present in, for example, a biological sample, such as blood, serum, saliva, or tissue from an infected individual. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A polynucleotide of the invention is operably linked when it is positioned adjacent to or close to one or more expression control elements, which direct transcription and/or translation of the polynucleotide.

Polynucleotides of the invention can be used, for example, as probes or primers, for example PCR primers, to detect the presence of *E. canis* polynucleotides in a test sample, such as a biological sample. Probes are molecules capable of interacting with a target nucleic acid, typically in a sequence specific manner, for example, through hybridization. Primers are a subset of probes that can support an enzymatic manipulation and that can hybridize with a target nucleic acid such that the enzymatic manipulation occurs. A primer can be made from any combination of nucleotides or nucleotide derivatives or analogs available in the art that do not interfere with the enzymatic manipulation.

A probe or primer can be about 10, 15, 20, 25, 30, 40, 50, 60, 70, 80, 90, 100 or more contiguous nucleotides that encode polypeptides shown in, e.g., SEQ ID NOs:22-33.

The hybridization of nucleic acids is well understood in the art. Typically a probe can be made from any combination of nucleotides or nucleotide derivatives or analogs available in the art. The ability of such probes and primers to specifically hybridize to *E. canis* polynucleotide sequences will enable them to be of use in detecting the presence of complementary sequences in a given test sample. Polynucleotide probes and primers of the invention can hybridize to complementary sequences in a test sample such as a biological sample, including saliva, sputum, blood, plasma, serum, urine, feces, cerebrospinal fluid, amniotic fluid, wound exudate, or tissue. Polynucleotides from the sample can be, for example, subjected to gel electrophoresis or other size separation techniques or can be immobilized without size separation. The polynucleotide probes or primers can be labeled. Suitable labels, and methods for labeling probes and primers are known in the art, and include, for example, radioactive labels incorporated by nick translation or by kinase, biotin labels, fluorescent labels, chemiluminescent labels, bioluminescent labels, metal chelator labels and enzyme labels. The polynucleotides from the sample are contacted with the probes or primers under hybridization conditions of suitable stringencies.

Depending on the application, varying conditions of hybridization can be used to achieve varying degrees of selectivity of the probe or primer towards the target sequence. For applications requiring high selectivity, relatively stringent conditions can be used, such as low salt and/or high temperature conditions, such as provided by a salt concentration of from about 0.02 M to about 0.15 M salt at temperatures of from about 50° C. to about 70° C. For applications requiring less selectivity, less stringent hybridization conditions can be used. For example, salt conditions from about 0.14 M to about 0.9M salt, at temperatures ranging from about 20° C. to about 55° C. The presence of a hybridized complex comprising the probe or primer and a complementary polynucleotide from the test sample indicates the presence of *E. canis* or an *E. canis* polynucleotide in the sample.

Antibodies

Antibodies of the invention are antibody molecules that specifically bind to an *E. canis* polypeptide of the invention, variant polypeptides of the invention, or fragments thereof. An antibody of the invention can be specific for an *Ehrlichia canis* polypeptide, for example, an antibody specific for one or more of SEQ ID NOs:10, 22-33. An antibody of the invention can be a polyclonal antibody, a monoclonal antibody, a single chain antibody (scFv), or an antigen-binding fragment of an antibody. Antigen binding fragments of antibodies are the antigen-binding portion of an intact antibody comprising the antigen binding site or variable region of an intact antibody, wherein the portion is free of the constant heavy chain domains of the Fc region of the intact antibody. Examples of antigen binding fragments include Fab, Fab', Fab'-SH, $F(ab')_2$ and $F_v$ fragments.

An antibody of the invention can be any antibody class, including for example, IgG, IgM, IgA, IgD and IgE. An antibody or fragment thereof binds to an epitope of a polypeptide of the invention. An antibody can be made in vivo in suitable laboratory animals or in vitro using recombinant DNA techniques. Means for preparing and characterizing antibodies are well know in the art. See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992). For example, polyclonal antibodies can be produced by administering a polypeptide of the invention to an animal, such as a human or other primate, mouse, rat, rabbit, guinea pig, goat, pig, dog, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

"Specifically binds" or "specific for" means that a first antigen, e.g., an *E. canis* polypeptide, recognizes and binds to an antibody of the invention with greater affinity than to other, non-specific molecules. "Specifically binds" or "specific for" also means a first antibody, e.g., an antibody raised against SEQ ID NOs:22-33, recognizes and binds to SEQ ID NOs: 22-33, with greater affinity than to other non-specific molecules. A non-specific molecule is an antigen that shares no common epitope with the first antigen. In a preferred embodiment of the invention a non-specific molecule is not derived from *Ehrlichia* sp., and in particular is not derived from *Ehrlichia chaffeensis* or *Ehrlichia canis*. "*Ehrlichia* sp." refers to all species of the genus *Ehrlichia*. For example, an antibody raised against a first antigen (e.g., a polypeptide) to which it binds more efficiently than to a non-specific antigen can be described as specifically binding to the first antigen. In one embodiment, an antibody or antigen-binding portion thereof of the invention specifically binds to a polypeptide of SEQ ID NOs:2, 4, 6, 8, 10, 12, 14, 15, 16, 17, 18, 19, 20, 21, 22, 23, 24, 25, 26, 27, 28, 29, or fragments thereof when it binds with a binding affinity $K_a$ of $10^7$ l/mol or more. Specific binding can be tested using, for example, an enzyme-linked immunosorbant assay (ELISA), a radioimmunoassay (RIA), or a western blot assay using methodology well known in the art.

Antibodies of the invention include antibodies and antigen binding fragments thereof that (a) compete with a reference antibody for binding to SEQ ID NOs:22-33 or antigen binding fragments thereof, (b) binds to the same epitope of SEQ ID NOs:22-33 or antigen binding fragments thereof as a reference antibody; (c) binds to SEQ ID NOs:22-33 or antigen binding fragments thereof with substantially the same $K_d$ as a reference antibody; and/or (d) binds to SEQ ID NOs:22-33 or fragments thereof with substantially the same off rate as a reference antibody, wherein the reference antibody is an antibody or antigen-binding fragment thereof that specifically binds to a polypeptide of SEQ ID NOs:22-33 or antigen binding fragments thereof with a binding affinity $K_a$ of $10^7$ l/mol or more.

Additionally, monoclonal antibodies directed against epitopes present on a polypeptide of the invention can also be readily produced. For example, normal B cells from a mammal, such as a mouse, which was immunized with a polypeptide of the invention can be fused with, for example, HAT-sensitive mouse myeloma cells to produce hybridomas. Hybridomas producing *E. canis*-specific antibodies can be identified using RIA or ELISA and isolated by cloning in semi-solid agar or by limiting dilution. Clones producing *E. canis*-specific antibodies are isolated by another round of screening. Monoclonal antibodies can be screened for specificity using standard techniques, for example, by binding a polypeptide of the invention to a microtiter plate and measuring binding of the monoclonal antibody by an ELISA assay. Techniques for producing and processing monoclonal antibodies are known in the art. See e.g., Kohler & Milstein, Nature, 256:495 (1975). Particular isotypes of a monoclonal antibody can be prepared directly, by selecting from the initial fusion, or prepared secondarily, from a parental hybridoma secreting a monoclonal antibody of a different isotype by using a sib selection technique to isolate class-switch variants. See Steplewski et al., *P.N.A.S. U.S.A.* 82:8653 1985; Spria et al., *J. Immunolog. Meth.* 74:307, 1984. Monoclonal antibodies of the invention can also be recombinant monoclonal antibodies. See, e.g., U.S. Pat. No. 4,474,893; U.S. Pat. No. 4,816,567. Antibodies of the invention can also be chemically constructed. See, e.g., U.S. Pat. No. 4,676,980.

Antibodies of the invention can be chimeric (see, e.g., U.S. Pat. No. 5,482,856), humanized (see, e.g., Jones et al., *Nature* 321:522 (1986); Reichmann et al., *Nature* 332:323 (1988); Presta, *Curr. Op. Struct. Biol.* 2:593 (1992)), or human antibodies. Human antibodies can be made by, for example, direct immortilization, phage display, transgenic mice, or a Trimera methodology, see e.g., Reisener et al., *Trends Biotechnol.* 16:242-246 (1998).

Antibodies that specifically bind *E. canis* antigens (e.g., *E. canis* polypeptides shown in SEQ ID NO:2, 4, 6, 8, 10, 12, 14, 15, 16, 17, 18, 19, 20, 21, 22, 23, 24, 25, 26, 27, 28, 29, 30, 31, 32, 33), are particularly useful for detecting the presence of *E. canis* or *E. canis* antigens in a sample, such as a serum, blood, plasma, fecal, cell, tissue, urine or saliva sample from an *E. canis*-infected animal such as a human or dog. An immunoassay for *E. canis* or an *E. canis* antigen can utilize one antibody or several antibodies. An immunoassay for *E. canis* or an *E. canis* antigen can use, for example, a monoclonal antibody specific for an *E. canis* epitope, a combination of monoclonal antibodies specific for epitopes of one *E. canis* polypeptide, monoclonal antibodies specific for epitopes of different *E. canis* polypeptides, polyclonal antibodies specific for the same *E. canis* antigen, polyclonal antibodies specific for different *E. canis* antigens, or a combination of monoclonal and polyclonal antibodies. Immunoassay protocols can be based upon, for example, competition, direct reaction, or sandwich type assays using, for example, labeled antibody. Antibodies of the invention can be labeled with any type of label known in the art, including, for example, fluorescent, chemiluminescent, radioactive, enzyme, colloidal metal, radioisotope and bioluminescent labels.

Antibodies of the invention or antigen-binding fragments thereof can be bound to a support and used to detect the presence of *E. canis* or an *E. canis* antigen, e.g., an *E. canis* DIVA antigen or *E. canis* vaccine antigen. Supports include, for example, glass, polystyrene, polypropylene, polyethylene, dextran, nylon, amylases, natural and modified celluloses, polyacrylamides, agaroses and magletite.

Antibodies of the invention can further be used to isolate *E. canis* organisms or *E. canis* antigens by immunoaffinity columns. The antibodies can be affixed to a solid support by, for example, adsorption or by covalent linkage so that the antibodies retain their immunoselective activity. Optionally, spacer groups can be included so that the antigen binding site of the antibody remains accessible. The immobilized antibodies can then be used to bind *E. canis* organisms or *E. canis* antigens from a sample, such as a biological sample including saliva, serum, sputum, blood, urine, feces, cerebrospinal fluid, amniotic fluid, wound exudate, or tissue. The bound *E. canis* organisms or *E. canis* antigens are recovered from the column matrix by, for example, a change in pH.

Antibodies of the invention can also be used in immunolocalization studies to analyze the presence and distribution of a polypeptide of the invention during various cellular events or physiological conditions. Antibodies can also be used to identify molecules involved in passive immunization and to identify molecules involved in the biosynthesis of non-protein antigens. Identification of such molecules can be useful in vaccine development. Antibodies of the invention, including, for example, monoclonal antibodies and single chain antibodies, can be used to monitor the course of amelioration of a disease caused by *E. canis*. By measuring the increase or decrease of *E. canis* antibodies specific for *E. canis* antigens in a test sample from an animal, it can be determined whether a particular therapeutic regiment aimed at ameliorating the disorder is effective. Antibodies can be detected and/or quantified using for example, direct binding assays such as RIA, ELISA, or western blot assays.

Detection

The methods of the invention can be used to detect antibodies or antigen-binding antibody fragments specific for *Ehrlichia canis* antigens or *Ehrlichia canis* polynucleotides in a test sample, such as a biological sample, an environmental sample, or a laboratory sample. A test sample can potentially comprise *Ehrlichia* sp. polynucleotides, *Ehrlichia canis* polynucleotides, *Ehrlichia* sp. polypeptides, *Ehrlichia canis* polypeptides, antibodies specific for *Ehrlichia* sp., and/or antibodies specific for *Ehrlichia canis*, unrelated polynucleotide and polypeptides, combinations thereof, or none of the above. A biological sample can include, for example, sera, blood, cells, plasma, saliva, urine, feces, or tissue from a mammal such as a horse, cat, dog or human. The test sample can be untreated, precipitated, fractionated, separated, diluted, concentrated, or purified.

In one embodiment methods of the invention comprise contacting one or more polypeptides of the invention with a test sample under conditions that allow polypeptide/antibody complexes, i.e., immunocomplexes, to form. That is, polypeptides of the invention specifically bind to antibodies specific for *Ehrlichia canis* antigens located in the sample. In one embodiment of the invention one or more polypeptides of the invention specifically bind to antibodies that are specific for *Ehrlichia canis* antigens and do not specifically bind to antigens from other pathogens, such as, e.g., *Ehrlichia chaffeensis* antigens. One of skill in the art is familiar with assays and conditions that are used to detect antibody/polypeptide complex binding. The formation of a complex between polypeptides and antibodies in the sample is detected. The formation of antibody/polypeptide complexes is an indication that *Ehrlichia canis* polypeptides are present in the sample. The lack of detection of the polypeptide/antibody complexes is an indication that *Ehrlichia canis* polypeptides are not present in the sample.

Antibodies of the invention can be used in a method of detection of *Ehrlichia canis* antigens by obtaining a test sample from, e.g., a human or animal suspected of having an *Ehrlichia canis* infection. The test sample is contacted with antibodies of the invention under conditions enabling the formation of antibody-antigen complexes (i.e., immunocomplexes). One of skill in the art is aware of conditions that enable and are appropriate for formation of antigen/antibody complexes. The amount of antibody-antigen complexes can be determined by methodology known in the art. A level that is higher than that formed in a negative control sample indicates presence of *Ehrlichia canis* antigens. A negative control sample is a sample that does not comprise any *Ehrlichia canis* polypeptides. In one embodiment of the invention the negative control contains no *Ehrlichia* sp. polypeptides. In one embodiment of the invention an antibody is specific for *Ehrlichia canis* antigens and is not specific for antigens from other pathogens, such as, e.g., *Ehrlichia chaffeensis* antigens. Alternatively, a polypeptide of the invention can be contacted with a test sample. Antibodies specific for *Ehrlichia canis* in a positive test sample will form antigen-antibody complexes under suitable conditions. The amount of antibody-antigen complexes can be determined by methods known in the art.

In one embodiment of the invention, *Ehrlichia canis* infection can be detected in a subject. A biological sample is obtained from the subject. One or more purified polypeptides comprising SEQ ID NOs:22-33 or other polypeptides of the invention are contacted with the biological sample under conditions that allow polypeptide/antibody complexes to form. The polypeptide/antibody complexes are detected. The detection of the polypeptide/antibody complexes is an indication that antibodies specific for *Ehrlichia canis* are present. The lack of detection of the polypeptide/antibody complexes is an indication that the mammal does not have antibodies specific for *Ehrlichia canis*.

In one embodiment of the invention the *Ehrlichia canis* antibodies detected by an immunoassay of the invention are IgG, IgM, IgA, IgD or IgE. In another embodiment of the invention, the antibodies used to detect *Ehrlichia canis* antigens are IgG, IgM, IgA, IgD or IgE.

In one embodiment of the invention, *Ehrlichia canis* infection can be detected in a subject by about 5 days, 6 days, 7 days, 8 days, 9 days, 10 days, 11 days, 12 days, 13 days, 14 days, 15 days, 16 days, 17 days, 18 days, 19 days, 20 days, 21 days or more after the subject acquired the *Ehrlichia canis* infection. In one embodiment of the invention, *Ehrlichia canis* infection can be detected in a subject by about 21 days, 20 days, 19 days, 18 days, 17 days, 16 days, 15 days, 14 days, 13 days, 12 days, 11 days, 10 days, 9 days, 8 days, 7 days, 6 days, 5 days, or less after the subject acquired the *Ehrlichia canis* infection.

In one embodiment of the invention, the polypeptide/antibody complex is detected when an indicator reagent, such as an enzyme conjugate, which is bound to the antibody, catalyzes a detectable reaction. Optionally, an indicator reagent comprising a signal generating compound can be applied to the polypeptide/antibody complex under conditions that allow formation of a polypeptide/antibody/indicator complex. The polypeptide/antibody/indicator complex is detected. Optionally, the polypeptide or antibody can be labeled with an indicator reagent prior to the formation of a polypeptide/antibody complex. The method can optionally comprise a positive or negative control.

In one embodiment of the invention, one or more antibodies of the invention are attached to a solid phase or substrate. A test sample potentially comprising a protein comprising a polypeptide of the invention is added to the substrate. One or more antibodies that specifically bind polypeptides of the invention are added. The antibodies can be the same antibodies used on the solid phase or can be from a different source or species and can be linked to an indicator reagent, such as an enzyme conjugate. Wash steps can be performed prior to each addition. A chromophore or enzyme substrate is added and color is allowed to develop. The color reaction is stopped and the color can be quantified using, for example, a spectrophotometer.

In another embodiment of the invention, one or more antibodies of the invention are attached to a solid phase or substrate. A test sample potentially comprising a protein comprising a polypeptide of the invention is added to the substrate. Second anti-species antibodies that specifically bind polypeptides of the invention are added. These second antibodies are from a different species than the solid phase antibodies. Third anti-species antibodies are added that specifically bind the second antibodies and that do not specifically bind the solid phase antibodies are added. The third antibodies can comprise an indicator reagent such as an enzyme conjugate. Wash steps can be performed prior to each addition. A chromophore or enzyme substrate is added and color is allowed to develop. The color reaction is stopped and the color can be quantified using, for example, a spectrophotometer.

Assays of the invention include, but are not limited to those based on competition, direct reaction or sandwich-type assays, including, but not limited to enzyme linked immunosorbent assay (ELISA), western blot, IFA, radioimmunoassay (RIA), hemagglutination (HA), fluorescence polarization immunoassay (FPIA), and microtiter plate assays (any assay done in one or more wells of a microtiter plate). One assay of the invention comprises a reversible flow chromatographic binding assay, for example a SNAP® assay (reversible flow chromatographic assay). See e.g., U.S. Pat. No. 5,726,010.

Assays can use solid phases or substrates or can be performed by immunoprecipitation or any other methods that do not utilize solid phases. Where a solid phase or substrate is used, one or more polypeptides of the invention are directly or indirectly attached to a solid support or a substrate such as a microtiter well, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). In one embodiment of the invention a substrate is sintered, fine particles of polyethylene, commonly known as porous polyethylene, for example, 10-15 micron porous polyethylene from Chromex Corporation (Albuquerque, N. Mex.). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like. Immobilization of one or more analyte capture reagents, e.g., *E. canis* polypeptides, onto a device or solid support is performed so that an analyte capture reagent will not be washed away by the sample, diluent and/or wash procedures. One or more analyte capture reagents can be attached to a surface by physical adsorption (i.e., without the use of chemical linkers) or by chemical binding (i.e., with the use of chemical linkers). Chemical binding can generate stronger attachment of capture reagents on a surface and provide defined orientation and conformation of the surface-bound molecules.

In one type of assay format, one or more polypeptides can be coated on a solid phase or substrate. A test sample suspected of containing anti-*Ehrlichia canis* antibodies or antigen-binding fragments thereof is incubated with an indicator reagent comprising a signal generating compound conjugated to an antibodies or antibody fragments specific for *Ehrlichia canis* for a time and under conditions sufficient to form antigen/antibody complexes of either antibodies of the test sample to the polypeptides of the solid phase or the indicator reagent compound conjugated to an antibody specific for *Ehrlichia canis* to the polypeptides of the solid phase. The reduction in binding of the indicator reagent conjugated to anti-*Ehrlichia canis* antibodies to the solid phase can be quantitatively measured. A measurable reduction in the signal compared to the signal generated from, e.g., a confirmed negative *Ehrlichia canis* test sample indicates the presence of anti-Ehrlichia canis antibodies in the test sample. This type of assay can quantitate the amount of anti-Ehrlichia canis antibodies in a test sample.

In another type of assay format, one or more polypeptides of the invention are coated onto a support or substrate. A polypeptide of the invention is conjugated to an indicator reagent and added to a test sample. This mixture is applied to the support or substrate. If antibodies specific for *Ehrlichia canis* are present in the test sample they will bind the one or more polypeptides conjugated to an indicator reagent and to the one or more polypeptides immobilized on the support. The polypeptide/antibody/indicator complex can then be detected. This type of assay can quantitate the amount of anti-*Ehrlichia canis* antibodies in a test sample.

In another type of assay format, one or more polypeptides of the invention are coated onto a support or substrate. The test sample is applied to the support or substrate and incubated. Unbound components from the sample are washed away by washing the solid support with a wash solution. If *Ehrlichia canis* specific antibodies are present in the test sample, they will bind to the polypeptide coated on the solid phase. This polypeptide/antibody complex can be detected using a second species-specific antibody that is conjugated to an indicator reagent. The polypeptide/antibody/anti-species antibody indicator complex can then be detected. This type of assay can quantitate the amount of anti-*Ehrlichia canis* antibodies in a test sample.

Another embodiment of the invention provides a device that is suitable for a lateral flow assay. For example, a test sample is added to a flow matrix at a first region (a sample application zone). The test sample is carried in a fluid flow path by capillary action to a second region of the flow matrix where a label capable of binding and forming a first complex with an analyte in the test sample. The first complex is carried to a third region of the flow matrix where an *E. canis* polypeptide is immobilized at a distinct location. A second complex is formed between an immobilized polypeptide and the first complex including the antibody from the sample. For example, a first complex comprising a gold sol particle and an *E. canis* polypeptide bound to an *E. canis* antibody will specifically bind and form a second complex with a second immobilized *E. canis* polypeptide or with a second antibody directed to *E. canis* antibodies. The label that is part of the second complex can be directly visualized.

In another aspect, the invention includes one or more labeled specific binding reagents that can be mixed with a test sample prior to application to a device of the invention. In this case it is not necessary to have labeled specific binding reagents deposited and dried on a specific binding reagent pad in the device. A labeled specific binding reagent, whether added to a test sample or pre-deposited on the device, can be for example, a labeled antibody that specifically binds an antibody for *E. canis*.

An *E. canis* DIVA antigen or an *E. canis* vaccine antigen, e.g., a polypeptide, can be an immobilized analyte capture reagent in a reaction zone (solid phase). A second analyte capture reagent, e.g. an anti-IgG or anti-IgM antibody, that has been conjugated to a label, can either be added to the sample before the sample is added to the device, or the second analyte capture reagent can be incorporated into the device. For example the labeled specific binding reagent can be deposited and dried on a fluid flow path that provides fluid communication between the sample application zone and the solid phase. Contact of the labeled specific binding reagent with the fluid sample results in dissolution of the labeled specific binding reagent.

The device can also include a liquid reagent that transports unbound material (e.g., unreacted fluid sample and unbound specific binding reagents) away from the reaction zone (solid phase). A liquid reagent can be a wash reagent and serve only to remove unbound material from the reaction zone, or it can include a detector reagent and serve to both remove unbound material and facilitate analyte detection. For example, in the case of a specific binding reagent conjugated to an enzyme, the detector reagent includes a substrate that produces a detectable signal upon reaction with the enzyme-antibody conjugate at the reactive zone. In the case of a labeled specific binding reagent conjugated to a radioactive, fluorescent, or light-absorbing molecule, the detector reagent acts merely as a wash solution facilitating detection of complex formation at the reactive zone by washing away unbound labeled reagent.

Two or more liquid reagents can be present in a device, for example, a device can comprise a liquid reagent that acts as a wash reagent and a liquid reagent that acts as a detector reagent and facilitates analyte detection.

A liquid reagent can further include a limited quantity of an "inhibitor", i.e., a substance that blocks the development of the detectable end product. A limited quantity is an amount of inhibitor sufficient to block end product development until most or all excess, unbound material is transported away from the second region, at which time detectable end product is produced.

The formation of a polypeptide/antibody complex or a polypeptide/antibody/indicator complex can be detected by, for example, radiometric, calorimetric, fluorometric, size-separation, or precipitation methods. Optionally, detection of a polypeptide/antibody complex is by the addition of a secondary antibody that is coupled to an indicator reagent comprising a signal generating compound. Indicator reagents comprising signal generating compounds (labels) associated with a polypeptide/antibody complex can be detected using the methods described above and include chromogenic agents, catalysts such as enzyme conjugates fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Formation of the complex is indicative of the presence of anti-*Ehrlichia canis* antibodies in a test sample. Therefore, the methods of the invention can be used to diagnose *Ehrlichia canis* infection in an animal.

The methods of the invention can also indicate the amount or quantity of anti-Ehrlichia canis antibodies in a test sample. With many indicator reagents, such as enzyme conjugates, the amount of antibody present is proportional to the signal generated. Depending upon the type of test sample, it can be diluted with a suitable buffer reagent, concentrated, or contacted with a solid phase without any manipulation. For example, it usually is preferred to test serum or plasma samples that previously have been diluted, or concentrated specimens such as urine, in order to determine the presence and/or amount of antibody present.

The invention further comprises assay kits (e.g., articles of manufacture) for detecting anti-*Ehrlichia canis* antibodies or antigen-binding antibody fragments, or *Ehrlichia canis* polypeptides in a sample. A kit comprises one or more polypeptides of the invention and means for determining binding of the polypeptide to anti-*Ehrlichia canis* antibodies or antibody fragments in the sample. A kit or article of manufacture can also comprise one or more antibodies or antibody fragments of the invention and means for determining binding of the antibodies or antibody fragments to *Ehrlichia canis* polypeptides in the sample. A kit can comprise a device containing one or more polypeptides or antibodies of the invention and instructions for use of the one or more polypeptides or antibodies for, e.g., the identification of an *Ehrlichia canis* infection in a mammal. The kit can also comprise packaging material comprising a label that indicates that the one or more polypeptides or antibodies of the kit can be used for the identification of *Ehrlichia canis* infection. Other components such as buffers, stabilizers, positive controls, negative controls, detector reagents, and the like, known to those of ordinary skill in art, can be included in such test kits. The polypeptides, antibodies, assays, and kits of the invention are useful, for example, in the diagnosis of individual cases of *Ehrlichia canis* infection in a patient, as well as epidemiological studies of *Ehrlichia canis* outbreaks. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample.

Polypeptides and assays of the invention can be combined with other polypeptides or assays to detect the presence of *Ehrlichia canis* along with other organisms. For example, polypeptides and assays of the invention can be combined with reagents that detect heartworm and/or *Borrelia burgdorferi* and/or *Ehrlichia chaffeensis* and/or *Anaplasma platys* and/or *Anaplasma phagocytophilum.*

Polynucleotides of the invention can be used to detect the presence of *Ehrlichia canis* polynucleotides in a sample. The polynucleotides can be used to detect *Ehrlichia canis* polynucleotides in a sample by a simple hybridization reaction and can also be used in, e.g., polymerase chain reactions (PCR) such as a real-time PCR reaction. Methods and compositions of the invention can also be used to differentially detect the presence *Ehrlichia canis* from other *Ehrlichia* sp., such as *Ehrlichia chaffeensis.*

PCR assays are well described in the art, including, for example, U.S. Pat. Nos. 4,683,195; U.S. Pat. No. 4,683,202; U.S. Pat. No. 4,965,188. Generally, polynucleotide primers are annealed to denatured strands of a target nucleic acid. Primer extension products are formed by polymerization of deoxynucleoside triphosphates by a polymerase. PCR then involves repetitive cycles of template nucleic acid denaturation, primer annealing and extension of the annealed primers by the action of a thermostable polymerase. The process results in exponential amplification of the target *Ehrlichia canis* nucleic acids in the test sample, which allows for the detection of target polynucleotides existing in very low concentrations in a sample.

Real-time PCR assays are based on the detection of a signal, e.g., a fluorescent reporter signal. This signal increases in direct proportion to the amount of PCR product in a reaction. Real-time PCR is any amplification technique that makes it possible to monitor the evolution of an ongoing amplification reaction. See, Quantitation of DNA/RNA Using Real-Time PCR Detection, Perkin Elmer Applied Biosystems (1999); PCR Protocols (Academic Press New York, 1989). By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed.

One embodiment of the invention provides a method for detecting and/or quantifying *Ehrlichia canis* polynucleotides in a test sample. Sense primers and antisense primers can be added to a test sample under conditions suitable for a polymerase chain reaction. The primers hybridize with *Ehrlichia canis* polynucleotides such that an amplification product is formed if *Ehrlichia canis* polynucleotides are present in the test sample. Amplification products are detected and the presence and/or quantity of *Ehrlichia canis* polynucleotides are determined. Amplification products can be detected with a polynucleotide probe that hybridizes, under conditions suitable for a polymerase chain reaction, with an *Ehrlichia canis* polynucleotide sequence. The amplification product can be quantified by measuring a detection signal from the probe and comparing said detection signal to a second probe detection signal from a quantification standard. The quantification standard can be extracted in parallel with the test sample.

Methods of Treatment, Amelioration, or Prevention of a Disease Caused by *E. canis*

In one embodiment of the invention, a DIVA polypeptide, polynucleotide or antibody of the invention could be used to treat, ameliorate, or prevent a disease caused by *E. canis*. If, however, a DIVA polypeptide is used to treat, ameliorate, or prevent a disease caused by *E. canis*, it could not, thereafter, be used as a DIVA polypeptide for the detection and differentiation of infected, non-vaccinated, and vaccinated animals because a vaccinated animal's immune system could recognize the DIVA antigen used for vaccination. However, a DIVA polypeptide that does not cross-react with antibodies to the DIVA polypeptide used for treatment, amelioration or prevention of a disease caused by *E. canis* may still be used as an *E. canis* DIVA antigen.

For example, if SEQ ID NO:2 or a fragment thereof is used as a vaccine, then SEQ ID NOs:4, 6, 8, 10, 12, 14, 15, 16, 17, 18, 19, 20, 21, 22, 23, 24, 25, 26, 27, 28, 29, 30, 31, 32, 33 or combinations thereof can be used as a DIVA polypeptide, if they do not cross-react with antibodies specific for SEQ ID NO:2. Presently, none of SEQ ID NOs:10, 22-33 are used in a commercial subunit *E. canis* vaccine and SEQ ID NOs:10, 22-33 do not detect *E. canis*-specific antibodies in animals vaccinated with whole inactivated *E. canis* cells. Therefore, DIVA polypeptide selection is not presently an issue. However, those of skill in the art are aware of the composition of *E. canis* vaccines. If a commercial *E. canis* subunit vaccine were to comprise SEQ ID NOs: 10, 22-33, then one of skill in the art would avoid use of SEQ ID NOs:10, 22-33 (if necessary due to the generation of *E. canis* antibodies specific for SEQ ID NOs:10, 22-33) to differentiate vaccination status and would instead use other *E. canis* DIVA antigens.

Therefore, the DIVA polypeptides, polynucleotides, and antibodies could be used in two different ways: (1) as compositions for the prevention, treatment, or amelioration of a disease or infection caused by *E. canis*; and (2) as an *E. canis* DIVA antigen for the detection and differentiation of animals that are vaccinated; non-vaccinated; infected or not infected with *E. canis*.

Polypeptides, polynucleotides, and antibodies of the invention can be used to treat, ameliorate, or prevent a disease caused by *E. canis*. For example, an antibody, such as a monoclonal antibody of the invention or fragments thereof, can be administered to an animal, such as a human. In one embodiment of the invention an antibody or fragment thereof is administered to an animal in a pharmaceutical composition comprising a pharmaceutically acceptable carrier. A pharmaceutical composition comprises a therapeutically effective amount of an antibody or fragments thereof. A therapeutically effective amount is an amount effective in alleviating the symptoms of *E. canis* infection or in reducing the amount of *E. canis* organisms in a subject.

Polypeptides or polynucleotides of the invention can be present in an immunogenic composition and used to elicit an immune response in a host. An immunogenic composition is capable of inducing an immune response in an animal. An immunogenic polypeptide or polynucleotide composition of the invention is particularly useful in sensitizing an immune system of an animal such that, as one result, an immune response is produced that ameliorates or prevents the effect of *E. canis* infection. The elicitation of an immune response in animal model can be useful to determine, for example, optimal doses or administration routes. Elicitation of an immune response can also be used to treat, prevent, or ameliorate a disease or infection caused by *E. canis*. An immune response includes humoral immune responses or cell mediated immune responses, or a combination thereof. An immune response can also comprise the promotion of a generalized host response, e.g., by promoting the production of defensins.

The generation of an antibody titer by an animal against *E. canis* can be important in protection from infection and clearance of infection. Detection and/or quantification of antibody titers after delivery of a polypeptide or polynucleotide can be used to identify epitopes that are particularly effective at eliciting antibody titers. Epitopes responsible for a strong antibody response to *E. canis* can be identified by eliciting antibodies directed against *E. canis* polypeptides of different lengths. Antibodies elicited by a particular polypeptide epitope can then be tested using, for example, an ELISA assay to determine which polypeptides contain epitopes that are most effective at generating a strong response. Polypeptides or fusion proteins that contain these epitopes or polynucleotides encoding the epitopes can then be constructed and used to elicit a strong antibody response.

A polypeptide, polynucleotide, or antibody of the invention can be administered to a mammal, such as a mouse, rabbit, guinea pig, macaque, baboon, chimpanzee, human, cow, sheep, pig, horse, dog, cat, or to animals such as chickens or ducks, to elicit antibodies in vivo. Injection of a polynucleotide has the practical advantages of simplicity of construction and modification. Further, injection of a polynucleotide results in the synthesis of a polypeptide in the host. Thus, the polypeptide is presented to the host immune system with native post-translational modifications, structure, and conformation. A polynucleotide can be delivered to a subject as "naked DNA."

Administration of a polynucleotide, polypeptide, or antibody can be by any means known in the art, including intramuscular, intravenous, intrapulmonary, intramuscular, intradermal, intraperitoneal, or subcutaneous injection, aerosol, intranasal, infusion pump, suppository, mucosal, topical, and oral, including injection using a biological ballistic gun ("gene gun"). A polynucleotide, polypeptide, or antibody can be accompanied by a protein carrier for oral administration. A combination of administration methods can also be used to elicit an immune response. Antibodies can be administered at a daily dose of about 0.5 mg to about 200 mg. In one embodiment of the invention antibodies are administered at a daily dose of about 20 to about 100 mg.

Pharmaceutically acceptable carriers and diluents for therapeutic use are well known in the art and are described in, for example, Remington's Pharmaceutical Sciences, Mack Publishing Co. (A. R. Gennaro ed. (1985)). The carrier should not itself induce the production of antibodies harmful to the host. Such carriers include, but are not limited to, large, slowly metabolized, macromolecules, such as proteins, polysaccharides such as latex functionalized SEPHAROSE®, agarose, cellulose, cellulose beads and the like, polylactic acids, polyglycolic acids, polymeric amino acids such as polyglutamic acid, polylysine, and the like, amino acid copolymers, peptoids, lipitoids, and inactive, avirulent virus particles or bacterial cells. Liposomes, hydrogels, cyclodextrins, biodegradable nanocapsules, and bioadhesives can also be used as a carrier for a composition of the invention.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, phosphate buffered saline, Ringer's solution, Hank's solution, glucose, glycerol, dextrose, malodextrin, ethanol, or the like, singly or in combination, as well as substances such as wetting agents, emulsifying agents, tonicity adjusting agents, detergent, or pH buffering agents. Additional active agents, such as bacteriocidal agents can also be used.

If desired, co-stimulatory molecules, which improve immunogen presentation to lymphocytes, such as B7-1 or B7-2, or cytokines such as MIP1$\alpha$, GM-CSF, IL-2, and IL-12, can be included in a composition of the invention. Optionally, adjuvants can also be included in a composition. Adjuvants are substances that can be used to nonspecifically augment a specific immune response. Generally, an adjuvant and a polypeptide of the invention are mixed prior to presentation to the immune system, or presented separately, but are presented into the same site of the animal. Adjuvants can include, for example, oil adjuvants (e.g. Freund's complete and incomplete adjuvants) mineral salts (e.g. $Alk(SO_4)_2$; $AlNa(SO_4)_2$, $AlNH_4(SO_4)$, Silica, Alum, $Al(OH)_3$, and $Ca_3(PO_4)_2$), polynucleotides (i.e. Polyic and Poly AU acids), and certain natural substances (e.g. wax D from *Mycobacterium tuberculosis*, as well as substances found in *Corynebacterium parvum, Bordetella pertussis* and members of the genus *Brucella*. Adjuvants which can be used include, but are not limited to MF59-0, aluminum hydroxide, N-acetyl-muramyl-L-threonyl-D-isoglutamine (thr-MDP), N-acetyl-nor-muramyl-L-alanyl-D-isoglutamine (CGP 11637), referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/TWEEN® 80 emulsion.

The compositions of the invention can be formulated into ingestible tablets, buccal tablets, troches, capsules, elixirs, suspensions, syrups, wafers, injectable formulations, mouthwashes, dentrifices, and the like. The percentage of one or more polypeptides, polynucleotides, or antibodies of the invention in such compositions and preparations can vary from 0.1% to 60% of the weight of the unit.

Administration of polypeptides, polynucleotides, or antibodies can elicit an immune response in the animal that lasts for at least 1 week, 1 month, 3 months, 6 months, 1 year, or longer. Optionally, an immune response can be maintained in an animal by providing one or more booster injections of the polypeptide, polynucleotide, or antibodies at 1 month, 3 months, 6 months, 1 year, or more after the primary injection. If desired, co-stimulatory molecules or adjuvants can also be provided before, after, or together with the compositions.

A composition of the invention comprising a polypeptide, polynucleotide, antibody, or a combination thereof is administered in a manner compatible with the particular composition used and in an amount that is effective to elicit an immune response as detected by, for example, an ELISA. A polynucleotide can be injected intramuscularly to a mammal, such as a baboon, chimpanzee, dog, or human, at a dose of 1 ng/kg, 10 ng/kg, 100 ng/kg, 1000 ng/kg, 0.001 mg/kg, 0.1 mg/kg, or 0.5 mg/kg. A polypeptide or antibody can be injected intramuscularly to a mammal at a dose of 0.01, 0.05, 0.5, 0.75, 1.0, 1.5, 2.0, 2.5, 5 or 10 mg/kg.

Polypeptides, polynucleotides, or antibodies, or a combination thereof can be administered either to an animal that is not infected with *E. canis* or can be administered to an *E. canis*-infected animal. The particular dosages of polynucleotide, polypeptides, or antibodies in a composition will depend on many factors including, but not limited to the species, age, gender, concurrent medication, general condition of the mammal to which the composition is administered, and the mode of administration of the composition. An effective amount of the composition of the invention can be readily determined using only routine experimentation.

A method of monitoring an *E. canis* infection in a patient is also provided. The method includes determining the level of anti-*E. canis* antibodies in a sample of a biological fluid from a patient suffering from or at risk of an *E. canis* infection at a first time point using polypeptides of the invention. The level of anti-*E. canis* antibodies is determined in one or more samples of the biological fluid from the patient at one or more different time points. The levels of anti-*E. canis* antibodies are determined at different time points such that the *E. canis* infection is monitored. The level or amount of anti-*E. canis* antibodies provide an indication of the success of treatment or therapy, or of progression of the infection.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Preparation of Formalin Inactivated *E. Canis* for Immunization into Dogs

*E. canis* was grown in canine cell culture using methods described in the literature. See e.g., Breitschwerdt, Antimicrobial Agents and Chemotherapy, 1998, Vol 42:362-368.

Using light microscopy, 030 cells were estimated to be greater than 80% infected by *E. canis*. Two liters of *E. canis* infected cell culture were collected, centrifuged and the pellet retained yielding 7.31 gms of material (wet weight). It is presumed water made up 80% of the weight of the material, giving an estimated dry weight of 1.462 gms (20% of the weight of the material). The cell pellet was resuspended to 20 mg/ml in PBS (dry weight) for a total volume of 73 ml.

To this resuspended cell pellet, 0.73 ml of formalin solution was added (Sigma Catalog HT50-1-2 Formalin Solution 10%, neutral buffered) for a final formaldehyde concentration of 0.04%. The solution was stirred overnight at 4° C. The inactivated mixture was centrifuged and the cell pellet retained. The pellet was washed by resuspension into 250 mls of PBS. The material was collected by centrifugation and the wash was repeated one time.

The washed cell pellet was resuspended into 73 mls of PBS. The sample was aliquoted to 73 screw cap vials and frozen at −80° C. Each vial contains 20 mgs (dry weight) of formalin inactivated *E. canis* cell culture, suitable for combining with the appropriate adjuvant for immunization into animals.

Example 2

Preparation of Formalin Inactivated *E. canis* with Two Different Adjuvants, Protocol for the Immunization of Beagles with *E. canis* Antigen, and Testing of Sera from Immunized Beagles Using SNAP® 3Dx® (Reversible Flow Chromatographic Assay)

The preparation of antigen with aluminum hydroxide adjuvant is a technique well known to those skilled in the art. For example see “Antibodies, A Laboratory Manual”, Cold Spring Harbor Press, 1988, pp 99.

For immunization into dogs (laboratory beagles), two sets of doses were prepared with aluminum hydroxide adjuvant prepared as described above and two sets of doses were prepared with Ribi adjuvant (Corixa Corp., Seattle Wash.) using the protocol described by the manufacturer. Each dose contained approximately 20 mg of formalin inactivated *E. canis* cell culture (dry weight).

Kennel kept laboratory beagles were selected for immunization with the *E. canis* formalin inactivated antigen. Two groups of two dogs each; with each group using a different adjuvant were dosed with the formalin inactivated *E. canis* preparation (aluminum oxide or Ribi). On day 0 all 4 dogs were found to be sero-negative using both the SNAP® 3Dx® (reversible flow chromatographic assay) diagnostic as well as western blot analysis using *E. canis* organism.

The IACUC committee of Covance Research Products Inc. approved the protocol for immunization of laboratory beagles. Dogs were vaccinated on days 0, 28 and 56 with weekly 1 ml bleeds being monitored using SNAP® 3Dx® (reversible flow chromatographic assay). All dogs were dosed with the appropriate test article subcutaneously in the dorsoscapular area. All four animals seroconverted to a positive test on SNAP®3Dx® (reversible flow chromatographic assay) *E. canis* by day 42. Production bleeds were taken on days 42 and 70 (approximately 50 ml blood that yielded approximately 25 ml sera).

FIG. 1 shows SNAP®3Dx® Assay (reversible flow chromatographic assay) evaluation of laboratory beagles. The SNAP® device (reversible flow chromatographic assay) was used as described by manufacturer. “Pre” sample is from day 0. “Post” sample is from day 42. The *E. canis* positive spot becomes positive in all 4 dogs for the day 42 sample. Similar results were observed for the day 70 sample.

Experiments with a third vaccine comprising a third adjuvant, BCG, (Calbiochem of EMD Biosciences, Inc. San Diego, Calif.) revealed similar results. Preparation of the third vaccine was identical to the preparations described for the Ribi adjuvant vaccine described above except: 1) formalin inactivation was for 24 hrs at 4 C, and 2) 1 mg of BCG was added. The vaccination schedule was day 0, day 14, with weekly bleeds assayed for reactivity with *E. canis* proteins.

Example 3

Enrichment of *E. canis* from Cell Culture Using PERCOLL® Gradients

For DNA isolation and western blot analysis, *E. canis* was enriched from cell culture using PERCOLL® density gradients. The process of isolating intracellular pathogens from cell culture, such as Ehrlichia, is a technique well known to those skilled in the art. For example, see Akira et al. (1982) Purification of *Rickettsia tsutsugamushi* by PERCOLL® density gradient centrifugation, Microbiol. Immunol., 26:321-328.

A typical *E. canis* enrichment began with 1.5 liters of infected cell culture (see above). The cells were centrifuged 6,000×g, the cell pellet retained and the supernatant discarded. The cell pellet was resuspended into 20 ml of PBS that was followed by a second centrifugation. The supernatant was discarded and supernatant retained. The pellet was then resuspended into 20 ml of PBS, sonicated for 5 seconds at 20 kHz, power setting 1.5 using a Branson sonicator. The sample was then centrifuged at 500×g for 5 minutes to pellet large debris.

PERCOLL® was added to the supernatant to a final concentration of 32% (4.5 ml of PERCOLL® with 10 ml of sample). The sample was loaded into Oak Ridge tubes compatible with a 70.1 Ti ultracentrifuge rotor, and centrifuged for 30 minutes at 63,000×g. The opaque band was collected using a Pasteur pipette. The opaque band is highly enriched for Ehrlichia (confirmed using light microscopy of the collected sample). After a 1:4 dilution with PBS, the sample was aliquoted and centrifuged at 12,000×g. The supernatant was discarded and the *Ehrlichia* pellet stored at −80° C.

Example 4

Testing of Sera or Plasma from Vaccinated and Infected Dogs by Western Blot

The use of 1-dimensional SDS-PAGE gel analysis and 2-dimensional gel analysis (1$^{st}$ dimension isoelectric focusing, 2$^{nd}$ dimension SDS-PAGE) is well known to those skilled in the art. For example see Current Protocols in Molecular Biology, eds. F. M. Ausubel et al., John Wiley & Sons Inc., 1997, pages 10.2.2-10.3.11. The use of western blots to analyze proteins separated using these methods are well known to those skilled in the art. For example see Current Protocols in Molecular Biology, eds. F. M. Ausubel et al., John Wiley & Sons Inc., 1997, pages 10.8.1-10.8.116.

Figure 2:
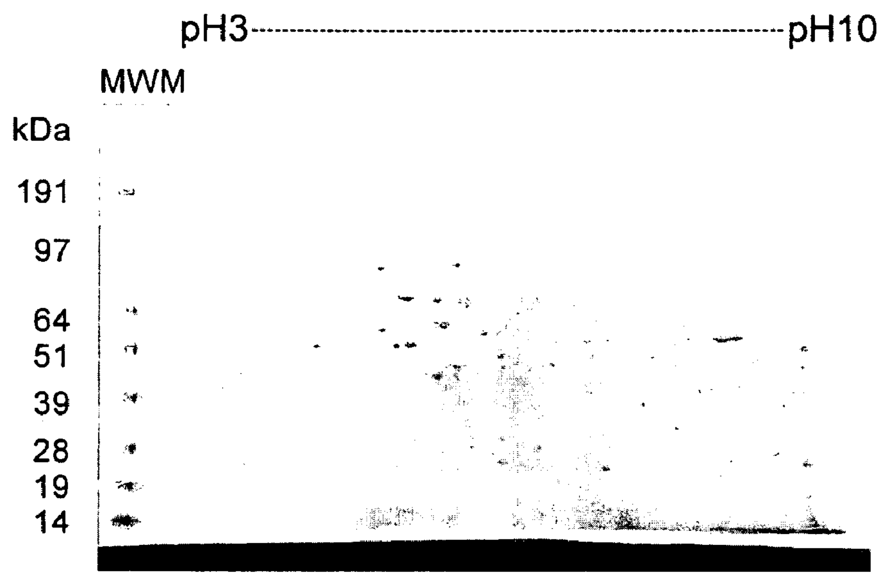
FIG. 2 shows a gel of *E. canis* proteins separated using 2D gel electrophoresis. Stained with BIOSAFE™ Coomassie Blue (Bio-Rad Inc.).
Figure 3:
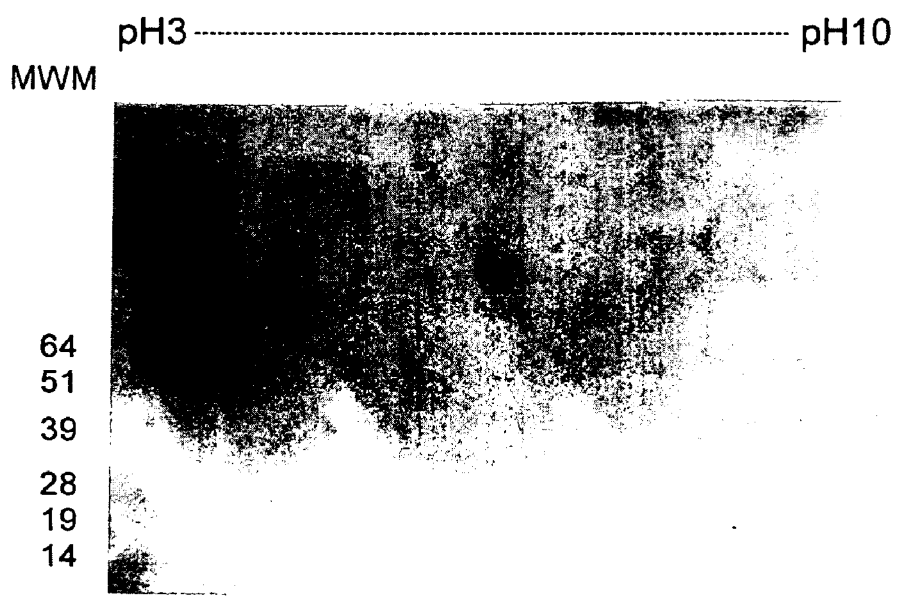
FIG. 3 shows a western blot of *E. canis* proteins using dog sera harvested at day 0. The plasma dilution is 1:100. These dogs were negative for reactivity with *E. canis* antigens.
Figure 4:
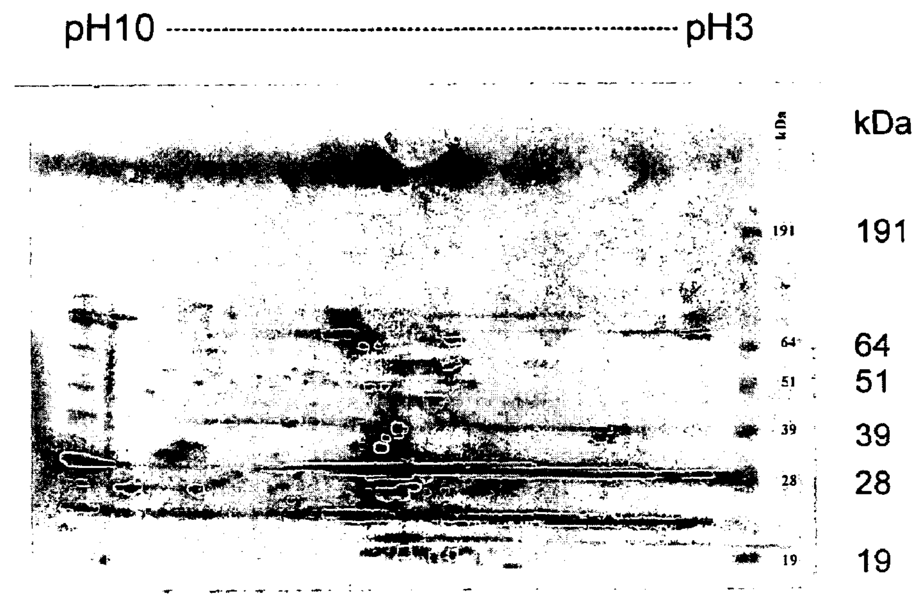
FIG. 4 shows a western blot of *E. canis* proteins using dog sera from a pool of four vaccinated animals. The sera dilution is 1:100.
Figure 5:
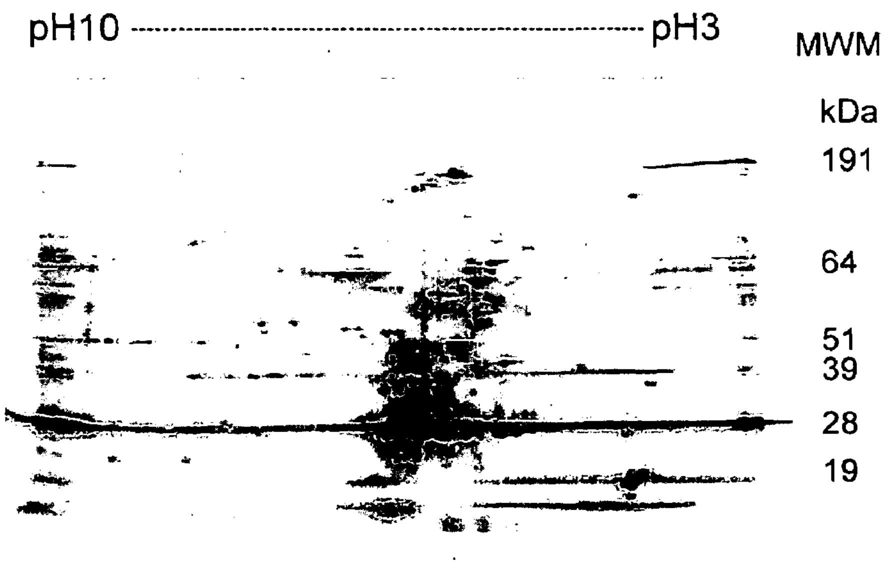
FIG. 5 shows a western blot of *E. canis* proteins using dog plasma from a pool of infected animals. The sera dilution is 1:1000.

Initial work was performed using western analysis of proteins separated with 1D gels (data not shown), followed by western analysis of proteins separated using 2D gels. Proteins from whole *E. canis* harvested from cell culture were analyzed using 2D gel electrophoresis (materials and reagents used as described by the manufacturer; Bio-Rad Life Sciences Research, Hercules, Calif. 94547). The amount of sample to load per gel was determined empirically (see FIG. 2). The proteins were blotted to nitrocellulose and probed using canine sera from laboratory beagles at day 0, dogs vaccinated with formalin inactivated *E. canis* antigen (see above), or sera from animals infected with *E. canis* (see FIGS. 3, 4 & 5).

Positive canine sera and plasma was isolated from dogs infected with *E. canis. E. canis* infection was verified by western analysis of lymphocytes harvested from whole blood from these dogs, and confirmed by use of the IDEXX SNAP®3Dx® assay (reversible flow chromatographic assay) with canine sera or plasma (commercially available from IDEXX Laboratories Inc., used as described by the manufacturer).

For western blot analysis proteins were separated using 1D SDS-PAGE or 2D isoelectric focusing/SDS-PAGE gels followed by electo-blotting of the proteins from the gels to nitrocellulose. The nitrocellulose blots were incubated in a blocking solution of 2.5% non fat dry milk dissolved into Tris buffered saline (pH 7.5), 0.05% TWEEN® 20 (polysorbate). Canine sera or plasma was diluted to the titer as described into buffer containing an *E. coli* lysate to block non-specific binding with 30% normal calf sera and incubated for 2 hrs at room temperature or over night at 4° C. After washing 3 times in TBS-TWEEN® (polysorbate) (0.05%), the blots were transferred to a buffer containing 50% fetal calf sera, 50% TBS-TWEEN® (polysorbate)-Kathon (0.05% & 0.5% respectively) to prevent nonspecific binding of a rabbit anti-canine Fc polyclonal antibody conjugated to horseradish peroxidase (Jackson Immuno Research, West Grove, Pa. 19390). The rabbit anti-canine Fc polyclonal antibody conjugate was diluted 1:5,000. The gels were washed 3 times with TBS TWEEN® (polysorbate) (0.05%), one time with TBS, and the presence of HRP detected using ECL western Blotting Detection Reagents (Amersham Biosciences, Piscataway, N.J. 08855-1327) used as described by manufacturer. Digital images of exposed X-ray film were captured using a GelDoc 2000 (Bio-Rad Inc.).

Example 5

Isolation of DNA from *E. canis* and Construction of a Lambda Expression Library and Screening of the *E. canis* Lambda Expression Library for Clones Having DIVA Activity The preparation and screening of lambda expression libraries is a technique well known to those skilled in the art. For example, see Current Protocols in Molecular Biology, eds. F. M. Ausubel et al., John Wiley & Sons Inc., 1997, pages 5.1 through 5.8.6. For the construction of the expression library, genomic DNA was purified from *E. canis* isolated from cell culture by PERCOLL® gradient centrifugation (see above). DNA was purified using a genomic DNA purification kit from Qiagen Sciences (Germantown, Md.). A Lambda ZAP® II predigested EcoRI/CIAP Vector Kit (Stratagene Corp., La Jolla, Calif. 92037) was used as specified by the manufacturer for construction of the library. *E. canis* genomic DNA was partially digested with TSP509 and fragments ranging from 2-6 kb were isolated using agarose gel electrophoresis and ligated into the lambda vector. Phage were packaged and grown as specified by the manufacturer.

Approximately 120,000 individual lambda plaques were screened for binding to sera isolated from dogs identified as positive for infection with *E. canis*, but negative for reactivity with sera from animals vaccinated with formalin inactivated *E. canis* (see above). From the initial screen 84 individual plaques were identified as having this activity.

Lambda plaques were subjected to two rounds of plaque purification and retested to verify positive reactivity with sera from *E. canis* infected animals, negative reactivity when screened with sera from vaccinated animals.

Isolated lambda plaques were screened for cross reactivity with sera from animals identified as being seropositive for *Anaplasma phagocytophilia, Borrelia burgdorferi* (causative agent of Lyme disease), *Rickettsia rickettsii* (causative agent of Rocky Mountain Spotted Fever), *Leptospira interrogans* and *Dirofilaria immitis* (causative agent of canine heartworm).

At the end of the screening process, 43 lambda plaques were found to react with sera from animals infected with *E. canis* that did not react with sera from vaccinated dogs or sera from dogs infected with other canine pathogens (see above).

Using the ZAP® feature of the cloning vector as per the manufacturers instructions, inserts into the lambda vector were converted to plasmids. The plasmids were transformed into the *E. coli* strain XL-1 blue for protein expression and analysis of encoded proteins by western blot. The ends of the *E. canis* DNA inserts were subjected to DNA sequence analysis using T7 and T3 sequencing primers.

Sequence information from both the T7 and T3 reactions for all 43 clones was submitted for BLAST analysis to the NCBI website. Results were tabulated in an excel format. Based on sequence identity between the clone and the available shotgun genome sequence for *E. canis* (NCBI: NZ_AAEJ01000001), segments of genomic DNA for each clone were identified. Individual clones sharing common genes were grouped for further analysis by western blot using pools of infected and vaccinated canine sera. Based on similar banding patterns, duplicate clones were eliminated. Any clones showing reactivity to both sets of sera were eliminated. As a result of this analysis, 23 clones were selected for further evaluation. The grouping of the clones and the common antigen per group is shown in Table 2.

TABLE 2

| Common Antigen | Clone Number(s) |
|---|---|
| 120 kDa Antigen | 2, 10, 17, 33, 35, 79 |
| Heat Shock Proteins | 4, 9, 24, 66 |
| ATPase | 7, 84 |
| Ribosomal Protein L1 | 21, 47, 65 |
| 200 kDa Antigen | 26, 55, 76 |
| Hypothetical Protein | 75 |
| Pyruvate Dehydrogenase | 5 |
| Ribosomal Protein (50S) | 6 |
| Unknown | 57 |
| Transcriptional Regulator | 82 |

Example 6

Figure 6:
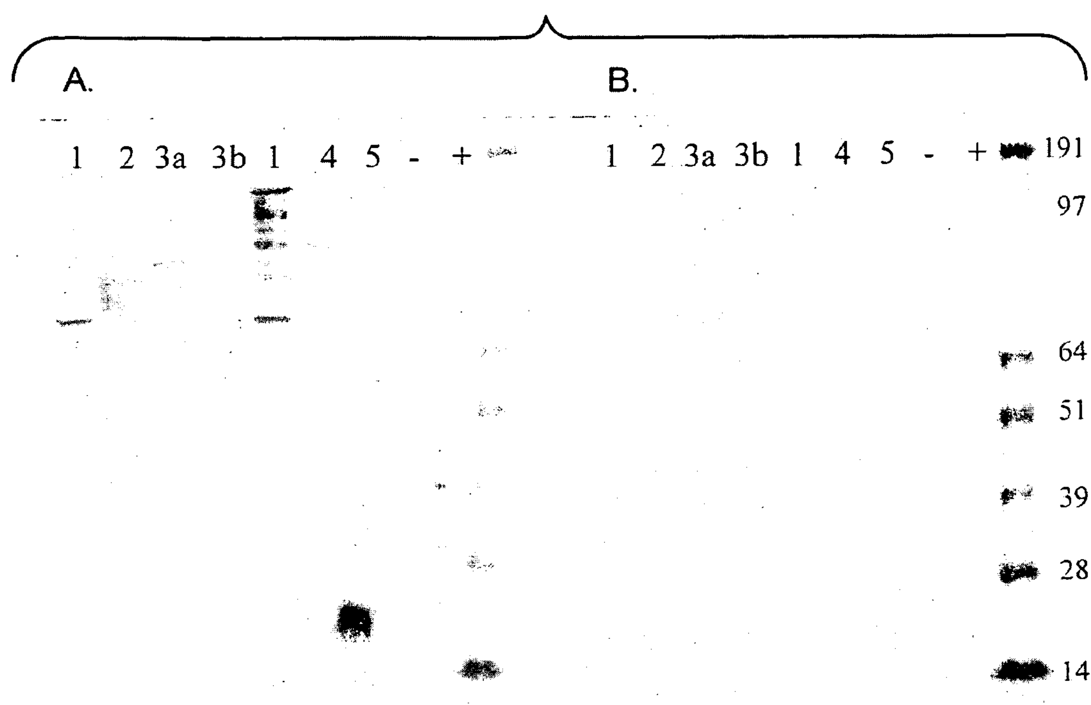
FIG. 6 shows a western blot of six different *E. canis* DIVA antigens expressed in *E. coli* and probed with either dog sera from a pool of four infected animals (A) or dog sera pooled from four vaccinated animals (B). Sera dilutions were 1:100 for vaccinated animals or 1:500 for the infected animals. The DIVA antigens represented include: (1) 200 kDa antigen, (2) Ribosomal protein L1, (3a and 3b) "ATPase"—two different segments, (4) 120 kDa antigen, (5) Heat shock proteins/p16 antigen.

Western Blot Analysis Using Individual *E. canis* Positive Canine Serum Samples All 23 clones were analyzed on individual SDS-PAGE gels. Each gel was transferred to nitrocellulose and subjected to western blotting using individual samples of canine sera from dogs that were only positive for *E. canis* infections by ELISA/SNAP® (reversible flow chromatographic assay) testing. Canine serum was diluted 1:500 in the same diluent described in Example 4 containing *E. coli* lysate and reactivity was detected using standard colorometric horseradish peroxidase techniques (Opti-4CN, Bio-Rad). A total of thirteen individual canine serum samples were evaluated. Blots were compared across samples to determine the number of dogs showing reactivity to a predominant band or set of bands per clone. The results are summarized in Table 3 and FIG. 6 (clones listed in bold are depicted in the figure).

TABLE 3

| Common Antigen | Clone Number(s) | Positive Reactors |
|---|---|---|
| 120 kDa Antigen | 2, 10, **17**, 33, 35 | 13/13 |
| Heat Shock Proteins | **9** | 12/13 |
| ATPase | **7**, **84** | 12/13 |
| Ribosomal Protein L1 | 21, 47, **65** | 12/13 |
| 200 kDa Antigen | **26**, **55**, 76 | 12/13 |

All 23 clones were also analyzed by western blot using pooled canine sera that had tested positive for other vector-borne infectious diseases. Samples testing positive by ELISA or SNAP® (reversible flow chromatographic assay) for the following single infections were evaluated: Heartworm, Lyme, *Anaplasma phagocytophilum*, or *E. ewingii*. None of the clones identified in the table above showed cross-reactivity with positive canine sera for these other vector-borne infections.

Example 7

Identification of Relevant Gene Segments Encoding *E. canis* Diva Antigens a. 120 kDa Antigen This antigen was previously described by Yu et al. (J Clin Microbiol. 2000 January; 38(1):369-74; see also, McBride et al., 2000 Infec. Immun. 68:13) and shown to be useful in the diagnosis of *E. canis* infections in dogs. This antigen has been described as both "p120" and "p140" *E. canis* antigen. See, id. Yu et al. explains that a recombinant protein expressed by the p120 gene has a molecular size of 140 kDa on a sodium dodecyl sulfate gel, which is larger than the predicted molecular mass of the protein. See, Yu et al., page 373. The Walker group (Yu et al, and McBride et al.) refer to the protein both as *E. canis* p120 and p140. Therefore, this disclosure uses both p120 and p140 interchangeably to describe this protein. The accession number for the *E. canis* p120/140 gene is AF112369 and the associated protein is AAD34330. See also, accession no. YP302666. Clones 2, 10, 17, and 33 contain full-length segments of the 120 kDa antigen gene. Clone 35 may contain a truncation of this gene. (See, SEQ ID NOs:1 and 2).

This gene was amplified from *E. canis* genomic DNA and subcloned into a pET expression system with a 6-His tag according to the manufacturer's instructions (Invitrogen). Sequencing results of this plasmid exactly matched the gene sequence encoding the protein shown in SEQ NO:ID 2, from amino acids 58 to 589. Protein lysates from BL21 bacteria induced to express this protein were analyzed by western blotting with infected canine sera and compared to western blots probed with sera from animals vaccinated with formalin inactivated *E. canis* cells. Consistent with previous findings, only sera from infected dogs recognized this protein of the expected molecular weight (data not shown).

P120 has a 36 amino acid motif that is repeated 14 times. See, SEQ ID NO:15. The repeated portion (underlined region in SEQ ID NO:15 is a 60 kD peptide). SEQ ID NO:16 shows the aligned 14 repeats. SEQ ID NO:17 shows the consensus sequence of the 14 repeats.

One embodiment of the invention provides a polypeptide comprising:

KEEX$_1$TPEVX$_2$AEDLQPAVDX$_3$SX$_4$EHSSSEVGX$_5$KVSX$_6$TS (SEQ ID NO:17).

Where $X_1$=S or N $X_2$=K or R $X_3$=G, D, or S $X_4$=V or I $X_5$=E or K $X_6$=E or K Another embodiment of the invention provides a multimeric polypeptide where SEQ ID NO:17 is repeated two or more times. The multimeric polypeptide can also comprise one or more heterologous polypeptides.

In another embodiment, the invention provides a polypeptide of SEQ ID NO:21, XPEVKAEDLQPAVDGSVEHX, wherein each of the X's=0, 1, 2, 3, 4, 5, 6, 7, 8, 9, 10, 11, 12, 13, 14, or 15 amino acids.

b. 200 kDa Antigen

This antigen was previously described by McBride et al. (J Clin Microbiol. 2001 January; 39(1):315-22) and shown to be useful in the diagnosis of ehrlichiosis. The accession number for this gene is AF252298 and associated protein AAK01145. A portion of this protein sequence is associated with a published patent (SEQ ID NO:2 of U.S. Pat. No. 6,355,777, accession number AAE96254). We have identified a different region of this protein that serves as diagnostic antigen for ehrlichiosis and a DIVA reagent. The portion of the gene spans from nucleotide 1081 of AF252298 through to the end, nucleotide 4266. (See SEQ ID NOs:3 and 4).

This gene was amplified from *E. canis* genomic DNA and subcloned into a pET expression system with a 6-His tag according to the manufacturer's instructions (Invitrogen). Sequencing results of this plasmid exactly matched the gene sequence encoding the protein shown in SEQ ID NO:4, from amino acids 1 to 1061. Protein lysates from BL21 bacteria induced to express this protein were analyzed by western blotting with infected canine sera and compared to western blots probed with sera from animals vaccinated with formalin inactivated *E. canis*. Consistent with previous findings, only sera from infected dogs recognized this protein of the expected molecular weight (data not shown).

c. ATPase

This gene (Locus tag "Ecan02000699") has been predicted by automated computational analysis of the shotgun genome sequence of *E. canis*. It codes for a protein of more than 4000 amino acids (ZP_00210575). The *E. canis* DIVA screen identified two separate regions of this gene and its associated protein as potential immunodominant antigens and DIVA reagents. The segments of the protein identified in clones 84 and 7 are amino acids 1984-2774 and 2980-3740, respectively, of accession number 46308382. (See SEQ ID NOs: 5, 6, 7, 8).

Both fragments of this gene was amplified from *E. canis* genomic DNA and subcloned separately into a pET expression system with a 6-His tag according to the manufacturer's instructions (Invitrogen). Sequencing results of this plasmid exactly matched the gene sequences associated with the proteins shown SEQ ID NOs:6 and 8, from amino acids 1 to 782 and 1 to 746 respectively. Protein lysates from BL21 bacteria induced to express these proteins were analyzed by western blotting with infected canine sera and compared to western blots probed with sera from animals vaccinated with formalin inactivated *E. canis*. Consistent with previous findings, only sera from infected dogs recognized these proteins of the expected molecular weight (data not shown).

d. Heat Shock Proteins

Although this clone contained a gene for the heat shock protein, GrpE, the gene sequence coding for the immunodominant antigen arises from a hypothetical protein sequence predicted by the automated computational analysis of the genome. Based on the molecular weight and pI of the protein, the gene of interest in clone 9 is locus number "Ecan02000495" and the associated protein 46308954.

Because this protein is only predicted from the computer annotation of the genome and has not been previously identified from *E. canis* organisms as an immunodominant protein, this is the first evidence that this gene is expressed in *E. canis* and stimulates an immune response in the infected canine host. The protein will be identified as the p16 antigen (see SEQ ID NO: 9 and 10).

Figure 7:
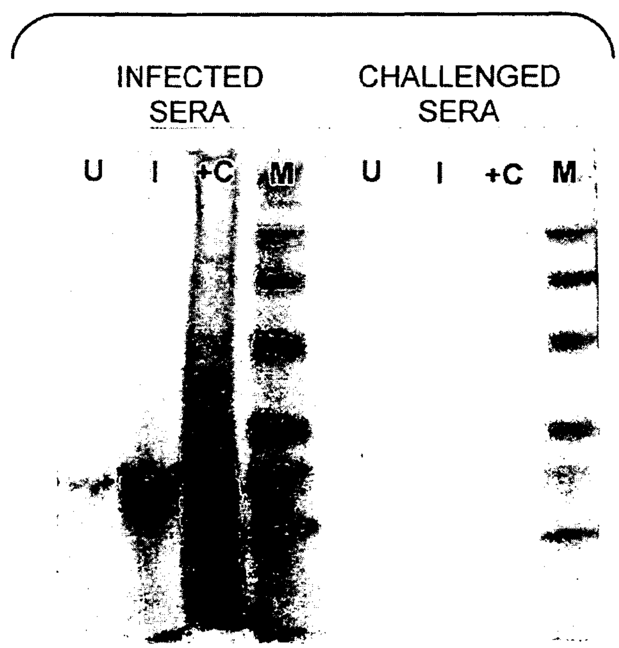
FIG. 7 demonstrates that cloned p16 antigen is recognized by sera from dogs infected with *E. canis* but not those that were vaccinated (shown as "challenged sera"). Lysates from uninduced (U) or induced (I) bacteria transformed with a vector expressing the p16 antigen or the original genomic fragment (+C) were separated by SDS-PAGE and transferred to nitrocellulose for western blot analysis.

This gene was amplified from the pBlueScript vector containing the genomic DNA of interest and subcloned into a pET expression system with a 6-His tag according to the manufacturer's instructions (Invitrogen). Sequencing results of this plasmid exactly matched the gene sequence associated with locus number "Ecan02000495". Protein lysates from BL21 bacteria induced to express this protein were analyzed by western blotting with infected canine sera and compared to western blots probed with sera from animals vaccinated with formalin inactivated *E. canis*. Consistent with previous findings, only sera from infected dogs recognized this protein of the expected molecular weight (see FIG. 7).

e. Ribosomal Protein L1

This gene is identified by the locus tag "Ecan02000476" from the *E. canis* genome. The associated protein has the accession number ZP_00211130 (see SEQ ID NOs:11 and 12). The identification of this protein has been predicted based on automated computational analysis of the genome. A BLAST analysis of this protein reveals that the sequence is about 70% identical to a surface protein of *E. chaffeensis* (Accession number 4894576). Immunoreactivity to the *E. chaffeensis* protein has previously been reported by Yu et al., (J Clin Microbiol. 1999 August; 37(8):2568-75). The *E. chaffeensis* protein (Accession number 4894576) is referred to as the 106 kDa protein precursor.

f. Possible Non-120 kDa Antigens

Within the genomic fragment containing the gene for the 120 kDa antigen, other genes are present that may also be immunodominant and DIVA reagents. For instance, clone 10 produces a different banding pattern on western blots probed with infected sera, compared to clones containing the 120 kDa antigen alone. Clone 10 contains genetic information for the VirD4 components of a Type IV secretory pathway and this gene sequence is identified by the locus tag "Ecan02000624". This gene codes for a protein of 723 amino acids (ZP_00211244), but only a portion of this protein appears to be expressed by clone 10, as determined by the molecular weight of the protein identified on the gel (see SEQ ID NOs:13 and 14).

Example 8

Evaluation of *E. canis* P140 Peptides

Sera from beagles immunized with formalin inactivated *E. canis* (vaccine samples) were tested using a microtiter-plate based immunoassay prepared using synthetic peptides derived from *E. canis* p140 protein (also known as p120, see Example 7).

Preparation of Formalin Inactivated *E. Canis* and Immunization of Beagles were Described in Examples 1 and 2. Samples from immunized beagles were tested using microtiter-plate based immunoassays prepared using synthetic peptides (SEQ ID NO:18, SEQ ID NO:19 and SEQ ID NO:20) in indirect and direct assay formats.

Indirect Assay Format

Samples were tested using microtiter-plate based immunoassays prepared using the synthetic peptides (SEQ ID NO:18, SEQ ID NO:19 and SEQ ID NO:20). Individual peptides were immobilized on microtiter wells by direct adsorption. A dilution of the test sample (1:100) was added to the microtiter well and unbound antibody was removed by washing. Antibody bound to the immobilized peptide was detected by reaction with an anti-species, in this case canine, horseradish peroxidase (HRPO) conjugate (1:2000 dilution), washing and addition of a HRPO substrate. The absorbance (A650) of individual microtiter wells was determined using a microtiter plate reader.

Direct Assay Format

Individual peptides (SEQ ID NO:18, SEQ ID NO:19 and SEQ ID NO:20) were conjugated to bovine serum albumin and immobilized on microtiter wells by direct adsorption. Synthetic peptides (SEQ ID NO:18, SEQ ID NO:19 and SEQ ID NO:20) were conjugated to an indicator reagent, horseradish peroxidase (HRPO). The test sample and the immunoassay peptide/indicator were added to a microtiter well coated with the corresponding peptide, which was incubated and washed. Antibody bound to the immobilized peptide and the peptide/indicator reagent was detected by addition of an HRPO substrate reagent. The absorbance (A650) of individual microtiter wells was determined using a microtiter plate reader.

Assay results are shown in Table 4. The positive control (PC, ID 1049:16E) and negative control (NC, 3818:57B) were known *E. canis* positive and negative serum samples, respectively. All samples were tested using the commercially available SNAP® 4Dx® test (reversible flow chromatographic assay) for *E. canis* antibody. Results for sequential temporal samples from 6 dogs (CVYDEH, CWMBDC, CVXCSM, CWMAXK, CVSCVA and CVXCAP) receiving the formalin inactivated *E. canis* antigen formulated using different adjuvants are shown for day 0 to day 42 post-immunization. Results of the SNAP® 4Dx® test demonstrate that an antibody response was induced in the vaccinated animals. None of the serum samples from vaccinated animals was reactive in the direct assay format. Several samples (for example from dog CWMAXK) had high background reactions in the indirect assay format.

The results demonstrate that antibody induced as a result of immunization using formalin inactivated vaccine was significantly non-reactive to the synthetic peptides derived from an *E. canis* p140 protein. (SEQ ID NO:18, SEQ ID NO:19 and SEQ ID NO:20).

TABLE 4

Reaction of sera from dogs immunized with formalin inactivated *E. canis* antigen measured using microtiter assays prepared using peptides derived from *E. canis* p140 protein. (SEQ ID NO: 18, SEQ ID NO: 19 and SEQ ID NO: 20).

| | | Indirect Plate Results (A650) | | | Direct Plate Results (A650) | | |
|---|---|---|---|---|---|---|---|
| Sample | 4Dx ® *E. canis* Result | SEQ ID NO: 18 | SEQ ID NO: 19 | SEQ ID NO: 20 | SEQ ID NO: 18 | SEQ ID NO: 19 | SEQ ID NO: 20 |
| 1049:16E (PC) | 0.72 | 2.071 | 2.075 | 1.867 | 2.049 | 1.821 | 1.495 |
| 3818:57B (NC) | N | 0.051 | 0.058 | 0.050 | 0.034 | 0.033 | 0.035 |
| CVYDEH day 0 | N | 0.050 | 0.062 | 0.045 | 0.034 | 0.034 | 0.035 |
| day 7 | N | 0.048 | 0.052 | 0.042 | 0.033 | 0.032 | 0.036 |
| day 14 | N | 0.051 | 0.055 | 0.048 | 0.036 | 0.034 | 0.038 |
| day 21 | N | 0.044 | 0.062 | 0.051 | 0.035 | 0.034 | 0.040 |
| day 28 | 0.04 (vw+) | 0.054 | 0.073 | 0.055 | 0.036 | 0.033 | 0.034 |
| day 35 | 0.07 (vw+) | 0.049 | 0.058 | 0.047 | 0.033 | 0.035 | 0.039 |
| day 42 | N | 0.051 | 0.059 | 0.053 | 0.034 | 0.035 | 0.040 |
| CWMBDC day 0 | 0.08 | 0.054 | 0.085 | 0.082 | 0.035 | 0.033 | 0.038 |
| day 7 | 0.20 | 0.064 | 0.078 | 0.072 | 0.038 | 0.035 | 0.035 |
| day 14 | 0.30 | 0.058 | 0.081 | 0.085 | 0.038 | 0.033 | 0.040 |
| day 21 | 0.24 | 0.051 | 0.101 | 0.078 | 0.037 | 0.040 | 0.039 |
| day 28 | 0.22 | 0.049 | 0.082 | 0.073 | 0.034 | 0.036 | 0.033 |
| day 35 | 0.17 | 0.043 | 0.068 | 0.081 | 0.033 | 0.040 | 0.035 |
| day 42 | 0.11 | 0.044 | 0.071 | 0.074 | 0.031 | 0.034 | 0.031 |
| CVXCSM day 0 | N | 0.049 | 0.082 | 0.051 | 0.033 | 0.035 | 0.034 |
| day 7 | N | 0.038 | 0.076 | 0.052 | 0.034 | 0.033 | 0.037 |
| day 14 | N | 0.044 | 0.069 | 0.049 | 0.033 | 0.032 | 0.038 |
| day 21 | 0.10 (w+) | 0.038 | 0.054 | 0.045 | 0.035 | 0.035 | 0.036 |
| day 28 | 0.10 (w+) | 0.044 | 0.060 | 0.049 | 0.036 | 0.033 | 0.035 |
| day 35 | 0.08 (vw+) | 0.040 | 0.062 | 0.053 | 0.034 | 0.035 | 0.041 |
| day 42 | 0.05 (vw+) | 0.041 | 0.057 | 0.049 | 0.033 | 0.035 | 0.036 |
| CWMAXK day 0 | 0.07 (vw+) | 0.043 | 0.078 | 0.054 | 0.034 | 0.039 | 0.037 |
| day 7 | 0.41 | 0.082 | 0.475 | 0.413 | 0.034 | 0.034 | 0.045 |
| day 14 | 0.44 | 0.049 | 0.782 | 0.607 | 0.034 | 0.035 | 0.044 |
| day 21 | 0.36 | 0.092 | 0.587 | 0.440 | 0.033 | 0.037 | 0.038 |
| day 28 | 0.39 | 0.063 | 0.407 | 0.258 | 0.037 | 0.034 | 0.038 |
| day 35 | 0.41 | 0.056 | 0.286 | 0.212 | 0.036 | 0.034 | 0.037 |
| day 42 | 0.35 | 0.048 | 0.196 | 0.155 | 0.034 | 0.034 | 0.041 |
| CVSCVA day 0 | 0.10 (w+) | 0.039 | 0.084 | 0.084 | 0.033 | 0.033 | 0.038 |
| day 7 | 0.37 | 0.040 | 0.107 | 0.066 | 0.032 | 0.032 | 0.036 |
| day 14 | 0.14 | 0.053 | 0.151 | 0.062 | 0.035 | 0.033 | 0.039 |
| day 21 | 0.33 | 0.057 | 0.131 | 0.072 | 0.035 | 0.033 | 0.034 |
| day 28 | 0.29 | 0.049 | 0.104 | 0.058 | 0.035 | 0.034 | 0.036 |
| day 35 | 0.36 | 0.043 | 0.108 | 0.079 | 0.034 | 0.039 | 0.040 |
| day 42 | 0.32 | 0.047 | 0.117 | 0.044 | 0.033 | 0.036 | 0.037 |
| CVXCAP day 0 | N | 0.041 | 0.065 | 0.040 | 0.032 | 0.035 | 0.032 |
| day 7 | 0.34 | 0.058 | 0.106 | 0.068 | 0.036 | 0.033 | 0.033 |
| day 14 | 0.30 | 0.087 | 0.150 | 0.112 | 0.034 | 0.035 | 0.039 |
| day 21 | 0.35 | 0.065 | 0.120 | 0.086 | 0.039 | 0.036 | 0.041 |
| day 28 | 0.19 | 0.054 | 0.103 | 0.059 | 0.035 | 0.036 | 0.032 |
| day 35 | 0.18 | 0.046 | 0.092 | 0.047 | 0.033 | 0.033 | 0.039 |
| day 42 | 0.19 | 0.051 | 0.067 | 0.047 | 0.035 | 0.035 | 0.038 |

Example 9

Sera from known *E. canis* positive and negative dogs was tested using a microtiter-plate based immunoassay prepared using the synthetic peptides obtained from *E. canis* protein p140 protein (also known as p120, see Example 7).

*E. canis* positive and negative field samples were obtained and tested using the SNAP® 4Dx® test (reversible flow chromatographic assay) for antibody to *E. canis*. Samples were then tested using indirect and direct microtiter plate format assays produced using synthetic peptides derived from the *E. canis* P140 protein (SEQ ID NO:18, SEQ ID NO:19 and SEQ ID NO:20).

Indirect Assay Format

Samples were tested using microtiter-plate based immunoassays prepared using the synthetic peptides (SEQ ID NO:18, SEQ ID NO:19 and SEQ ID NO:20). Individual peptides were immobilized on microtiter wells by direct adsorption. A dilution of the test sample (1:100) was added to the microtiter well and unbound antibody was removed by washing. Antibody bound to the immobilized peptide was detected by reaction with an anti-species, in this case canine, horseradish peroxidase (HRPO) conjugate (1:2000 dilution), washing and addition of a HRPO substrate. The absorbance (A650) of individual microtiter wells was determined using a microtiter plate reader.

Direct Assay Format

Individual peptides (SEQ ID NO:18, SEQ ID NO:19 and SEQ ID NO:20) were conjugated to bovine serum albumin and immobilized on microtiter wells by direct adsorption. The synthetic peptides (SEQ ID NO:18, SEQ ID NO:19 and SEQ ID NO:20) were conjugated to the indicator reagent, horseradish peroxidase (HRPO). The test sample and the immunoassay peptide/indicator were added to a microtiter well coated with the corresponding peptide, which was incubated and washed. Antibody bound to the immobilized peptide and the peptide/indicator reagent was detected by addition of an HRPO substrate reagent. The absorbance (A650) of individual microtiter wells was determined using a microtiter plate reader.

Table 4 shows results for *E. canis* positive and negative field samples tested using the indirect assay format. The positive control (PC, ID 1049:16E) and negative control (NC, 3818:57B) were known *E. canis* positive and negative serum samples, respectively. Samples were determined to be *E. canis* antibody positive or negative using the SNAP® 4Dx® test (reversible flow chromatographic assay). Assay results are shown for microtiter plate format assays made using peptide reagents (SEQ ID:18, SEQ ID:19 and SEQ ID:20).

Table 5 shows results for *E. canis* positive and negative field samples tested using the direct assay format. The positive control (PC, ID 1049:16E) and negative control (NC, 3818:57B) were known *E. canis* positive and negative serum samples, respectively. Samples were determined to be *E. canis* antibody positive or negative using the SNAP® 4Dx® test (reversible flow chromatographic assay). Assay results are shown for microtiter plate format assays made using peptide reagents (SEQ ID:18, SEQ ID:19 and SEQ ID:20).

TABLE 5

*E. canis* positive and negative field samples tested using the indirect microtiter plate format assay constructed using P140 peptides (SEQ ID NO: 18, SEQ ID NO: 19 and SEQ ID NO: 20).

| | | | Absorbance at 650 nM | | |
|---|---|---|---|---|---|
| | Sample | 4Dx ® Result | SEQ ID No: 18 | SEG ID NO: 19 | SEQ ID no: 20 |
| | 1049:16E (PC) | | 2.292 | 2.735 | 2.584 |
| | 3818:57B (NC) | | 0.051 | 0.065 | 0.045 |
| EC+ | HP 127 | 0.07 | 0.042 | 0.050 | 0.038 |
| EC+ | HP 143 | 0.08 | 2.867 | 2.825 | 2.731 |
| EC+ | HP 147 | 0.09 | 2.370 | 2.661 | 2.658 |
| EC+ | HP 151 | 0.21 | 2.176 | 2.093 | 2.535 |
| EC+ | HP 161 | 0.18 | 1.708 | 2.178 | 2.551 |
| EC+ | HP 165 | 0.08 | 2.690 | 2.492 | 2.525 |
| EC+ | HP 172 | 0.07 | 0.229 | 0.902 | 2.197 |
| EC+ | HP 185 | 0.38 | 2.497 | 2.622 | 2.704 |
| EC+ | HP 186 | 0.26 | 2.899 | 2.979 | 2.794 |
| EC+ | HP 188 | 0.40 | 2.482 | 2.578 | 2.898 |
| EC+ | HP 190 | 0.21 | 2.484 | 2.534 | 2.632 |
| EC+ | HP 192 | 0.18 | 1.473 | 2.132 | 2.526 |
| EC+ | HP 194 | 0.43 | 2.583 | 2.429 | 2.539 |
| EC+ | HP 197 | 0.22 | 2.150 | 2.239 | 2.537 |
| EC+ | HP 201 | 0.36 | 2.449 | 2.472 | 2.519 |
| EC+ | HP 206 | 0.10 | 2.477 | 2.247 | 2.549 |
| EC+ | HP 207 | 0.08 | 2.030 | 2.359 | 2.369 |
| EC+ | HP 209 | 0.20 | 0.262 | 0.218 | 1.102 |
| EC+ | HP 213 | 0.21 | 1.471 | 1.662 | 2.406 |
| EC+ | HP 215 | 0.19 | 2.144 | 2.431 | 2.721 |
| EC− | HP 116 | 0.02 | 0.110 | 0.065 | 0.070 |
| EC− | HP 119 | 0.02 | 0.102 | 0.091 | 0.079 |
| EC− | HP 120 | 0.01 | 0.058 | 0.063 | 0.045 |
| EC− | HP 121 | 0.02 | 0.054 | 0.064 | 0.057 |
| EC− | HP 122 | 0.03 | 0.053 | 0.059 | 0.040 |
| EC− | HP 124 | 0.02 | 0.055 | 0.061 | 0.052 |
| EC− | HP 128 | 0.02 | 0.068 | 0.072 | 0.054 |
| EC− | HP 129 | 0.02 | 0.056 | 0.057 | 0.044 |
| EC− | HP 130 | 0.01 | 0.049 | 0.048 | 0.039 |
| EC− | HP 131 | 0.01 | 0.051 | 0.053 | 0.043 |
| EC− | HP 132 | 0.03 | 0.057 | 0.061 | 0.038 |
| EC− | HP 134 | 0.02 | 0.059 | 0.084 | 0.114 |
| EC− | HP 137 | 0.03 | 0.043 | 0.046 | 0.037 |
| EC− | HP 138 | 0.01 | 0.055 | 0.063 | 0.048 |
| EC− | HP 139 | 0.01 | 0.064 | 0.062 | 0.056 |
| EC− | HP 140 | 0.00 | 1.574 | 2.444 | 2.491 |
| EC− | HP 142 | 0.02 | 0.065 | 0.068 | 0.069 |

TABLE 5-continued

*E. canis* positive and negative field samples tested using the indirect microtiter plate format assay constructed using P140 peptides (SEQ ID NO: 18, SEQ ID NO: 19 and SEQ ID NO: 20).

| | | | Absorbance at 650 nM | | |
|---|---|---|---|---|---|
| | Sample | 4Dx ® Result | SEQ ID No: 18 | SEG ID NO: 19 | SEQ ID no: 20 |
| EC− | HP 144 | 0.02 | 0.080 | 0.079 | 0.081 |
| EC− | HP 145 | 0.01 | 1.564 | 1.934 | 2.095 |
| EC− | HP 148 | 0.01 | 0.037 | 0.043 | 0.043 |

TABLE 6

*E. canis* positive and negative field samples tested using the direct microtiter plate format assay constructed using P140 peptides (SEQ ID NO: 18, SEQ ID NO: 19 and SEQ ID NO: 20).

| | | 3Dx ® | Absorbance at 650 nM | | |
|---|---|---|---|---|---|
| Sample | | SNAP S-Bkg | SEQ ID NO: 18 | SEQ ID NO: 19 | SEQ ID NO: 20 |
| 1049:16E (PC) | | 0.72 | 2.753 | 2.079 | 2.018 |
| 3818:57B (NC) | | Neg | 0.034 | 0.035 | 0.036 |
| 1049:16A | *E. canis* pos | 0.28 | 0.201 | 0.173 | 1.448 |
| 1049:16G | *E. canis* pos | 0.50 | 0.034 | 0.034 | 0.039 |
| 1049:16Q | *E. canis* pos | 0.39 | 2.308 | 1.933 | 2.151 |
| 1049:16U | *E. canis* pos | 0.56 | 0.627 | 2.038 | 2.254 |
| 1061:03B | *E. canis* pos | 0.49 | 0.083 | 0.338 | 0.889 |
| 1061:03I | *E. canis* pos | 0.27 | 2.766 | 2.593 | 1.646 |
| 1177:21D | *E. canis* pos | 0.15 | 0.042 | 0.046 | 0.126 |
| 1177:21G | *E. canis* pos | 0.41 | 1.087 | 1.675 | 1.835 |
| 1177:21K | *E. canis* pos | 0.34 | 0.681 | 1.930 | 2.010 |
| 1177:63O | *E. canis* pos | 0.41 | 0.146 | 0.112 | 1.587 |
| 1183:85A | *E. canis* pos | 0.49 | 2.768 | 2.757 | 2.476 |
| 1256:31I | *E. canis* pos | 0.23 | 0.044 | 0.086 | 0.143 |
| 813:91F | *E. canis* pos | 0.41 | 1.239 | 1.570 | 1.993 |
| 813:91I | *E. canis* pos | 0.41 | 0.212 | 0.517 | 1.646 |
| EC 10 | *E. canis* pos | 0.37 | 0.236 | 0.302 | 0.465 |

The results demonstrate that antibody induced as a result of natural infection was reactive to the synthetic peptides derived from the *E. canis* p140 protein. (SEQ ID NO:18, SEQ ID NO:19 and SEQ ID NO:20).

Example 10

Testing of Sera from Known *E. canis* Positive and Negative Dogs Using a Microtiter-plate Based Immunoassay Prepared Using the Synthetic Peptides (SEQ ID NO:22, SEQ ID NO:23 and SEQ ID NO:24) Obtained from the *E. canis* Protein p16 Protein. Assays were Performed Using the Indirect Assay Format Making Use of Anti-Canine HRPO Conjugate as the Indicator.

Sera from six *E. canis*-antibody positive and three *E. canis*-antibody negative canines were obtained from Sinclair Research (Columbia, Mo.). Serum samples were found to be positive or negative by testing using the licensed reversible flow chromatographic binding assay IDEXX SNAP® 4Dx® test (reversible flow chromatographic assay) for *E. canis* antibody. Reversible flow chromatographic SNAP® assay (reversible flow chromatographic assay) results are shown in Table 7.

Samples were tested using microtiter-plate based immunoassays prepared using synthetic peptides (SEQ ID NO:22, SEQ ID NO:23 and SEQ ID NO:24) derived from the *E. canis* p16 surface protein. The synthetic peptide was immobilized in Immulon microtiter wells at 0.25 ug/ml (SEQ ID NOs: 22 and 23, or at 0.5 ug/ml (SEQ ID NO: 24)). A dilution of the test sample (1:100) was added to the microtiter well and unbound antibody was removed by washing. Antibody bound to the immobilized peptide was detected by reaction with an anti-species, in this case canine, horseradish peroxidase (HRPO) conjugate (1:2000 dilution), washing and addition of HRPO substrate. The absorbance at 650 nm (A650) of fluid in individual microtiter wells was determined using a microtiter-plate reader.

Results:

Results for positive and negative samples are shown in Table 7. Positive samples HP-319, HP-322, HP-326, HP-342, HP-354, HP-358 were reactive to the peptide sequences shown in SEQ ID NO:22, SEQ ID NO:23 and SEQ ID NO:24. Negative samples HP-302, HP-303 and HP-306 were nonreactive to the peptide sequences shown in SEQ ID NO:22, SEQ ID NO:23 and SEQ ID NO:24.

Conclusions:

The results demonstrate that antibody induced as a result of natural infection was reactive to the synthetic peptides derived from the *E. canis* p16 protein (SEQ ID NO:22, SEQ ID NO:23 and SEQ NO:24) in the indirect assay format described above.

TABLE 7

Assay results for positive and negative canine samples using *E. canis* synthetic peptide (SEQ ID NO: 22, SEQ ID NO: 23 and SEQ ID NO: 24) coated microtiter wells and anti-species conjugate as indicator. A650 is absorbance at 650 nm. The "4Dx ® SNAP ®" (reversible flow chromatographic assay) column presents the results from the reversible flow chromatographic SNAP ® 4Dx ® assay (reversible flow chromatographic assay).

| | | Plate Results (A650) | | | | | |
|---|---|---|---|---|---|---|---|
| | 4Dx | SEQ ID NO: 22 | | SEQ ID NO: 23 | | SEQ ID NO: 24 | |
| Sample | SNAP | A650 | Result | A650 | Result | A650 | Result |
| 1049:16E (PC) | pos | 1.733 | pos | 2.309 | pos | 1.943 | pos |
| 3818:57B (NC) | neg | 0.046 | neg | 0.044 | neg | 0.041 | neg |
| HP-319 | pos | 1.274 | pos | 1.765 | pos | 0.755 | pos |
| HP-322 | pos | 1.247 | pos | 1.996 | pos | 0.692 | pos |
| HP-326 | pos | 1.656 | pos | 2.159 | pos | 0.991 | pos |
| HP-342 | pos | 0.704 | pos | 1.480 | pos | 0.277 | pos |
| HP-354 | pos | 1.220 | pos | 1.745 | pos | 0.573 | pos |
| HP-358 | pos | 1.890 | pos | 2.270 | pos | 0.342 | pos |
| HP-302 | neg | 0.043 | neg | 0.043 | neg | 0.032 | neg |
| HP-303 | neg | 0.036 | neg | 0.039 | neg | 0.029 | neg |
| HP-306 | neg | 0.044 | neg | 0.039 | neg | 0.039 | neg |

Example 11

Testing of Sera from Known *E. canis* Positive and Negative Dogs Using a Microtiter-plate Based Immunoassay Prepared Using the Synthetic Peptides (SEQ ID NO:22, SEQ ID NO:23 and SEQ ID NO:24) Derived from the *E. canis* p16 Protein Sequence. Assays were Performed Using the Direct Assay Format Making Use of HRPO-labeled Peptide as the Indicator.

Sera from seven *E. canis*-antibody positive and three *E. canis*-antibody negative canines were obtained from field dogs. Serum samples were found to be positive or negative by testing using the licensed reversible flow chromatographic IDEXX SNAP® 3Dx® (reversible flow chromatographic assay) for *E. canis* antibody. Assay results are shown in Table 8.

Samples were tested using a microtiter-plate based immunoassay prepared using the synthetic peptides (SEQ ID NO:22, SEQ ID NO:23 and SEQ NO:24) derived from the *E. canis* P16 surface protein. The synthetic peptides were immobilized on microtiter plate wells at 1 ug/ml. Separate quantities of the synthetic peptides were conjugated to the indicator reagent horseradish peroxidase (HRPO). The test sample and the peptide:HRPO conjugate (1 ug/ml) were added to the peptide-coated microtiter well, which was incubated and washed. Sample antibody bound to the immobilized peptide and the peptide::HRPO conjugate was immobilized in the microtiter well. This complex was detected by addition of an HRPO substrate reagent. The optical density of individual microtiter wells was determined using a microtiter plate reader.

Results:

Results for positive and negative samples are shown in Table 8. Positive samples 813:91I, 1049:16A, 1049:16U, 1061:03I, 1177:21G, 1177:21K and 1177:63O were reactive to the peptide sequences shown in SEQ ID NO:22, SEQ ID NO:23 and SEQ ID NO:24. Negative samples 3818:57A, 3818:57C and 3818:57D were nonreactive to the peptide sequences shown in SEQ ID NO:22, SEQ ID NO:23 and SEQ ID NO:24.

Conclusions:

The results demonstrate that antibody induced as a result of natural infection was reactive to the synthetic peptides derived from the *E. canis* p16 protein (SEQ ID NO:22, SEQ ID NO:23 and SEQ NO:24) in the direct assay format described above.

TABLE 8

Assay results for positive and negative canine field samples using *E. canis* synthetic peptide-coated microtiter wells (SEQ ID NO: 22, SEQ ID NO: 23 and SEQ ID NO: 24) and *E. canis* synthetic peptide-conjugates (SEQ ID NO: 22, SEQ ID NO: 23 and SEQ ID NO: 24) as indicators. A650 is absorbance at 650 nm. The "3Dx ® SNAP ®" (reversible flow chromatographic assay) column presents the results from the reversible flow chromatographic SNAP ® 3Dx ® assay (reversible flow chromatographic assay).

| | | Plate Results (A650) | | | | | |
|---|---|---|---|---|---|---|---|
| | 3Dx | SEQ ID NO: 22 | | SEQ ID NO: 23 | | SEQ ID NO: 24 | |
| Sample | SNAP | A650 | Result | A650 | Result | A650 | Result |
| 1049:16E (PC) | pos | 2.497 | pos | 2.908 | pos | 1.367 | pos |
| 3818:57B (NC) | neg | 0.038 | neg | 0.041 | neg | 0.056 | neg |
| 813:91I | pos | 1.244 | pos | 1.828 | pos | 0.651 | pos |
| 1049:16A | pos | 0.547 | pos | 0.819 | pos | 0.116 | pos |
| 1049:16U | pos | 2.653 | pos | 3.531 | pos | 1.031 | pos |
| 1061:03I | pos | 0.665 | pos | 1.801 | pos | 0.127 | pos |
| 1177:21G | pos | 1.484 | pos | 2.353 | pos | 0.444 | pos |
| 1177:21K | pos | 2.612 | pos | 3.049 | pos | 1.077 | pos |
| 1177:63O | pos | 0.290 | pos | 2.091 | pos | 0.215 | pos |
| 3818:57A | neg | 0.039 | neg | 0.037 | neg | 0.041 | neg |
| 3818:57C | neg | 0.038 | neg | 0.036 | neg | 0.042 | neg |
| 3818:57D | neg | 0.037 | neg | 0.037 | neg | 0.040 | neg |

Example 12

Assay Results for Sera from 6 Dogs Experimentally Infected with *E. canis* Using Synthetic Peptide (SEQ ID NO:23) Coated Microtiter Plates and Anti-canine conjugate as indicator Six naïve dogs were experimentally infected with the Louisiana isolate of *E. canis*. Serum samples were obtained on days 3, 7, 10, 13, 17, 21, 24, 28 and 35 post infection. Samples were tested using microtiter-plate based immunoassays prepared using the p16-2 synthetic peptide (SEQ ID NO:23) derived from the *E. canis* p16 surface protein. The synthetic peptide was immobilized in microtiter wells, a dilution of the test sample (1:100) was added to the microtiter well and unbound antibody was removed by washing. Antibody bound to the immobilized peptide was detected by reaction with an anti-canine, horseradish peroxidase (HRPO) conjugate (1:2000 dilution), washing and addition of HRPO substrate. The optical density of individual microtiter wells was determined using a microtiter plate reader.

Results:

Assay results are shown in Table 9. All 6 dogs converted from a negative status to a positive status following experimental infection as measured by the commercially available reversible flow chromatographic SNAP® 4Dx® assay (reversible flow chromatographic assay). Sera from all dogs reacted to the *E. canis* p16-peptide shown in SEQ ID NO:23 at various times post infection. The times between experimental infection and initial reaction to the SEQ ID NO:23 peptide were as follows: Dog 108532, 17 days post-infection; Dog 115853, 13 days post-infection; Dog 265006, 17 days post-infection; Dog 268830, 13 days post-infection; Dog 285307, 13 days post-infection and Dog 533573, 13 days post-infection.

Conclusions:

The results demonstrate that antibody induced as a result of experimental infection was reactive to the synthetic peptide derived from the *E. canis* p16 protein (SEQ ID NO:23).

TABLE 9

Assay results using for serum from dogs experimentally infected using *E. canis* synthetic peptide (SEQ ID NO: 23) coated microtiter plates and anti-species conjugate as indicator. A650 is absorbance at 650 nm. The "4Dx ® SNAP ®" (reversible flow chromatographic assay) column presents the results from the reversible flow chromatographic SNAP ® 4Dx ® assay (reversible flow chromatographic assay).

| Canine | Sample | Time Point | 4Dx SNAP EC | SEQ ID NO: 23 A650 | SEQ ID NO: 23 Result |
|---|---|---|---|---|---|
| | 1049:16E | PC | | 2.253 | + |
| | 21172M | NC | | 0.035 | N |
| | | Cutoff | | 0.070 | |
| 108532 | E1-0 | d3 | Neg | 0.034 | N |
| | E1-1 | d7 | Neg | 0.035 | N |
| | E1-2 | d10 | Neg | 0.037 | N |
| | E1-3 | d13 | Neg | 0.069 | N |
| | E1-4 | d17 | Neg | 1.501 | + |
| | E1-5 | d21 | Neg | 1.662 | + |
| | E1-6 | d24 | +(.04) | 1.572 | + |
| | E1-7 | d28 | +(.06) | 1.604 | + |
| | E1-8 | d35 | +(.10) | 2.056 | + |
| 115853 | E2-0 | d3 | Neg | 0.034 | N |
| | E2-1 | d7 | Neg | 0.033 | N |
| | E2-2 | d10 | Neg | 0.039 | N |
| | E2-3 | d13 | Neg | 1.246 | + |
| | E2-4 | d17 | Neg | 1.393 | + |
| | E2-5 | d21 | Neg | 1.227 | + |
| | E2-6 | d24 | +(.04) | 1.549 | + |
| | E2-7 | d28 | +(.03) | 1.580 | + |
| | E2-8 | d35 | +(.04) | 1.939 | + |
| 265006 | E3-0 | d3 | Neg | 0.042 | N |
| | E3-1 | d7 | Neg | 0.035 | N |
| | E3-2 | d10 | Neg | 0.038 | N |
| | E3-3 | d13 | Neg | 0.052 | N |
| | E3-4 | d17 | Neg | 0.944 | + |
| | E3-5 | d21 | Neg | 1.031 | + |
| | E3-6 | d24 | Neg | 0.962 | + |
| | E3-7 | d28 | Neg | 0.840 | + |
| | E3-8 | d35 | +(.05) | 1.303 | + |
| 268830 | E4-0 | d3 | Neg | 0.037 | N |
| | E4-1 | d7 | Neg | 0.034 | N |
| | E4-2 | d10 | Neg | 0.038 | N |
| | E4-3 | d13 | Neg | 0.112 | + |
| | E4-4 | d17 | Neg | 1.432 | + |
| | E4-5 | d21 | +(.05) | 1.364 | + |
| | E4-6 | d24 | +(.05) | 1.167 | + |
| | E4-7 | d28 | +(.09) | 1.412 | + |
| | E4-8 | d35 | +(.12) | 1.986 | + |
| 285307 | E5-0 | d3 | Neg | 0.036 | N |
| | E5-1 | d7 | Neg | 0.046 | N |
| | E5-2 | d10 | Neg | 0.044 | N |
| | E5-3 | d13 | Neg | 1.018 | + |
| | E5-4 | d17 | Neg | 1.597 | + |
| | E5-5 | d21 | +(.05) | 1.478 | + |
| | E5-6 | d24 | +(.04) | 1.282 | + |
| | E5-7 | d28 | +(.04) | 1.329 | + |
| | E5-8 | d35 | +(.10) | 1.838 | + |
| 533573 | E6-0 | d3 | Neg | 0.037 | N |
| | E6-1 | d7 | Neg | 0.035 | N |
| | E6-2 | d10 | Neg | 0.032 | N |
| | E6-3 | d13 | Neg | 0.909 | + |
| | E6-4 | d17 | Neg | 1.832 | + |
| | E6-5 | d21 | +(.08) | 1.883 | + |
| | E6-6 | d24 | +(.08) | 1.964 | + |
| | E6-7 | d28 | +(.06) | 1.963 | + |
| | E6-8 | d35 | +(.15) | 2.166 | + |

Example 13

Preparation of Formalin Inactivated *E. canis* for Immunization into Dogs

*E. canis* was grown in canine cell culture using methods described in the literature. See Breitschwerdt, Antimicrobial Agents and Chemotherapy, 1998, Vol 42:362-368. Using light microscopy, 030 cells were estimated to be greater than 80% infected by *E. canis*. Two liters of *E. canis* infected cell culture were collected, centrifuged and the pellet retained yielded 7.31 gms of material (wet weight). It is presumed water made up 80% of the weight of the material, giving an estimated dry weight of 1.462 gms (20% of the weight of the material). The cell pellet was resuspended to 20 mg/ml in PBS (dry weight) for a total volume of 73 ml.

To this resuspended cell pellet, 0.73 ml of formalin solution was added (Sigma Catalog HT50-1-2 Formalin Solution 10%, neutral buffered) for a final formaldehyde concentration of 0.04%. The solution was stirred 12 to 24 hrs at 4° C. The inactivated mixture was centrifuged and the cell pellet retained. The pellet was washed by resuspension into 250 mls of PBS. The material was collected by centrifugation and the wash was repeated one time.

The sample was aliquoted to 73 screw cap vials and frozen at −80° C. Each vial contains 20 mgs (dry weight) of formalin inactivated *E. canis* cell culture, suitable for combining with the appropriate adjuvant for immunization into animals.

Example 14

Preparation of Formalin Inactivated *E. canis* with Two Different Adjuvants and Protocol for the Immunization of Beagles with *E. canis* Antigen.

For immunization into kennel-housed dogs (laboratory beagles) formalin inactivated *E. canis* antigen was formulated using three different adjuvants. Formalin inactivated *E. canis* antigen was prepared with Ribi adjuvant (Corixa Corp., Seattle Wash.) using the protocol described by the manufacturer. Each dose contained approximately 20 mg of formalin inactivated *E. canis* cell culture (dry weight). An additional formulation of immunogen was prepared using a combination of the Ribi adjuvant (described above) and the adjuvant BCG (1 mg per dose) (Calbiochem of EMD Biosciences, Inc., San Diego, Calif.). Two groups consisting of three dogs each were dosed 4 times over a period of 170 days (days 0, 14, 156, 170) using inactivated *E. canis* containing either Ribi adjuvant alone or Ribi adjuvant and BCG adjuvant in combination. In an effort to produce a vaccine-induced hyperimmune state, all dogs received a single dose (day 247) of formalin inactivated *E. canis* formulated using the adjuvant TiterMax® (CytRx Corp., Norcross, Ga.) or the adjuvant TiterMax® and the adjuvant BCG in combination using the manufacturer's instructions. Dogs were administered vaccines according to the following schedule:

| | Vaccine Administered/Day of Vaccination | | | |
|---|---|---|---|---|
| Dog ID | *E. canis*/Ribi | *E. canis*/ Ribi + BCG | *E. canis*/ TiterMax | *E. canis*/ TiterMax + BCG |
| CVYDEH | 0, 14, 156, 170 | | 247 | |
| CWMBDC | 0, 14, 156, 170 | | 247 | |
| CVXCSM | 0, 14, 156, 170 | | 247 | |
| CWMAXK | | 0, 14, 156, 170 | | 247 |
| CVSCVA | | 0, 14, 156, 170 | | 247 |
| CVXCAP | | 0, 14, 156, 170 | | 247 |

The IACUC committee of Covance Research Products Inc. approved the protocol for immunization of laboratory beagles. All dogs were dosed with the appropriate test article subcutaneously in the dorsoscapular area. On day 0 all 6 dogs were found to be sero-negative using both the reversible flow chromatographic SNAP® 3Dx® diagnostic (reversible flow chromatographic assay) as well as western blot analysis using *E. canis* organism. All six animals seroconverted to a positive test on the reversible flow chromatographic SNAP®3Dx® *E. canis* assay (reversible flow chromatographic assay) by day 42. Production bleeds were taken on days 226, 261, 268 and 282. (approximately 50 ml blood that yielded approximately 25 ml sera).

Example 15

Testing of Sera from Beagles Immunized with Formalin Inactivated *E. canis* (Vaccine Samples) Using a Microtiter-plate Based Immunoassay Prepared Using the Synthetic Peptides (SEQ ID NO:22, SEQ ID NO:23, SEQ ID NO:24) Obtained from the *E. canis* Protein p16 Protein Preparation of the formalin inactivated *E. canis* and immunization of beagles were described in Examples 13 and 14. Samples from immunized beagles were tested using the direct microtiter-plate based immunoassays prepared using the synthetic peptides (SEQ ID NO:22, SEQ ID NO:23 and SEQ ID NO:24).

Direct Assay Format

Samples were tested using microtiter-plate based immunoassays prepared using the synthetic peptides (SEQ ID NO:22, SEQ ID NO:23 and SEQ ID NO:24). The synthetic peptides were immobilized on microtiter plate wells at 1.0 ug/ml. Separate quantities of the synthetic peptides were conjugated to the indicator reagent horseradish peroxidase (HRPO). The test sample and the immunoassay peptide/indicator were added to the peptide-coated microtiter well, which was incubated and washed. Antibody bound to the immobilized peptide and the peptide/indicator reagent was immobilized in the microtiter well. This complex was detected by addition of an HRPO substrate reagent. The optical density of individual microtiter wells was determined using a microtiter plate reader.

Results

Assay results are shown in Table 10. The positive control (PC, ID 1049:16E) and negative control (NC, 3818:57 B) were known *E. canis* positive and negative serum samples, respectively. All samples were tested using the commercially available the reversible flow chromatographic SNAP® 4Dx® test (reversible flow chromatographic assay) for *E. canis* antibody. Results for sequential temporal samples from the 6 dogs (CVYDEH, CWMBDC, CVXCSM, CWMAXK, CVSCVA and CVXCAP) receiving the formalin inactivated *E. canis* antigen formulated using different adjuvants are shown for day 226, day 261, day 268 and day 282 post-immunization. Results of the reversible flow chromatographic SNAP® 4Dx® test demonstrate that an antibody response was induced in the vaccinated animals. None of the serum samples from vaccinated animals was reactive in the peptide (SEQ ID NO:22, SEQ ID NO:23 and SEQ ID NO:24) microtiter plate-format assay.

TABLE 10

Assay results using for serum from dogs immunized with formalin inactivated *E. canis* antigen measured using *E. canis* synthetic peptide (SEQ ID NO: 22, SEQ ID NO: 23, SEQ ID NO: 24) coated microtiter plates synthetic peptide-conjugate as indicator.
OD is optical density. The "4Dx ® SNAP ®" (reversible flow chromatographic assay) column presents the results from the reversible flow chromatographic SNAP ® 4Dx ® assay (reversible flow chromatographic assay).

| | | | Plate Results | | | | | |
|---|---|---|---|---|---|---|---|---|
| | | 4Dx SNAP | SEQ ID NO: 22 | | SEQ ID NO: 23 | | SEQ ID NO: 24 | |
| Adjuvant | Sample | OD/(result) | OD | RESULT | OD | RESULT | OD | RESULT |
| | 1049:16E (PC) | 0.72 | 2.276 | | 2.865 | | 1.021 | |
| | 3818:57B (NC) | neg | 0.043 | neg | 0.044 | neg | 0.042 | neg |
| Ribi | CVYDEH day 226 | neg | 0.038 | neg | 0.056 | neg | 0.037 | neg |
| | day 261 | 0.07 (pos) | 0.037 | neg | 0.046 | neg | 0.035 | neg |
| | day 268 | 0.17 (pos) | 0.045 | neg | 0.057 | neg | 0.038 | neg |
| | day 282 | 0.18 (pos) | 0.035 | neg | 0.048 | neg | 0.034 | neg |
| Ribi | CWMBDC day 226 | 0.08 (pos) | 0.050 | neg | 0.052 | neg | 0.043 | neg |
| | day 261 | 0.45 (pos) | 0.044 | neg | 0.090 | neg | 0.039 | neg |
| | day 268 | 0.40 (pos) | 0.039 | neg | 0.064 | neg | 0.038 | neg |
| | day 282 | 0.30 (pos) | 0.038 | neg | 0.058 | neg | 0.040 | neg |
| Ribi | CVXCSM day226 | neg | 0.034 | neg | 0.038 | neg | 0.042 | neg |
| | day 261 | neg | 0.044 | neg | 0.073 | neg | 0.071 | neg |
| | day 268 | 0.14 (pos) | 0.042 | neg | 0.038 | neg | 0.041 | neg |
| | day 282 | 0.23 (pos) | 0.044 | neg | 0.038 | neg | 0.054 | neg |
| Ribi + BCG | CWMAXK day 226 | 0.07 (pos) | 0.038 | neg | 0.035 | neg | 0.039 | neg |
| | day 261 | 0.26 (pos) | 0.043 | neg | 0.037 | neg | 0.036 | neg |
| | day 268 | 0.36 (pos) | 0.045 | neg | 0.043 | neg | 0.034 | neg |
| | day 282 | 0.34 (pos) | 0.038 | neg | 0.036 | neg | 0.034 | neg |
| Ribi + BCG | CVSCVA day 226 | .10 (pos) | 0.039 | neg | 0.036 | neg | 0.041 | neg |
| | day 261 | 0.51 (pos) | 0.041 | neg | 0.036 | neg | 0.036 | neg |
| | day 268 | 0.45 (pos) | 0.043 | neg | 0.035 | neg | 0.035 | neg |
| | day 282 | 0.47 (pos) | 0.036 | neg | 0.037 | neg | 0.036 | neg |
| Ribi + BCG | CVXCAP day 226 | neg | 0.041 | neg | 0.036 | neg | 0.034 | neg |
| | day 261 | 0.51 (pos) | 0.054 | neg | 0.046 | neg | 0.047 | neg |
| | day 268 | 0.42 (pos) | 0.041 | neg | 0.045 | neg | 0.043 | neg |
| | day 282 | 0.48 (pos) | 0.035 | neg | 0.034 | neg | 0.036 | neg |

Conclusions

The results demonstrate that antibodies induced as a result of immunization using formalin inactivated *E. canis* antigen were reactive on the reversible flow chromatographic SNAP® 4Dx® test (reversible flow chromatographic assay) which would indicate that an anti-*E. canis* antibody response was initiated. These same samples were nonreactive to the synthetic peptides derived from the *E. canis* P16 protein (SEQ ID NO:22, SEQ ID NO:23, SEQ ID NO:24).

Sera from dogs immunized with formalin inactivated *E. canis* antigen were nonreactive to the peptides derived from the *E. canis* P16 protein (SEQ ID NO:22, SEQ ID NO:23, SEQ ID NO:24). The synthetic peptides (SEQ ID NO:22, SEQ ID NO:23, SEQ ID NO:24) were nonreactive to antibody induced as a result of vaccination.

Example 15

Monitoring Treatment of *E. canis* Infection

Six dogs were experimentally infected with *E. canis*. Doxycycline was administered at 28 days post-infection. Antibodies specific for *E. canis* were detected using SEQ ID NO:23 with an indirect assay protocol. Polypeptides shown in SEQ ID NO:23 were immobilized on microtiter wells by direct adsorption. A dilution of the test sample (1:100) was added to the microtiter well and unbound antibody was removed by washing. Antibody bound to the immobilized peptide was detected by reaction with an anti-species, in this case rabbit anti-canine horseradish peroxidase (HRPO) conjugate (1:1000 dilution). The absorbance (A650) of individual microtiter wells was determined using a microtiter plate reader. The negative cutoff was 2× the negative control O.D. value.

Figure 8:
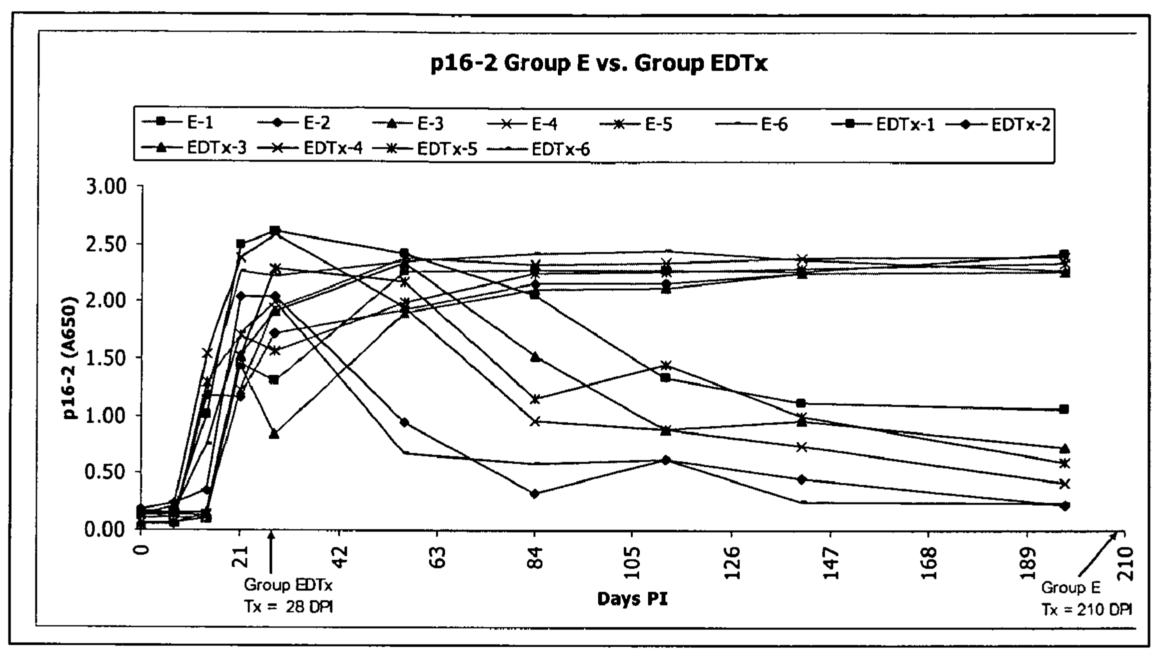
FIG. 8 demonstrates detection of antibodies specific for *E. canis* using a polypeptide shown in SEQ ID NO:23 in dogs over a time course including infection, treatment, and recovery.
Figure 9A:
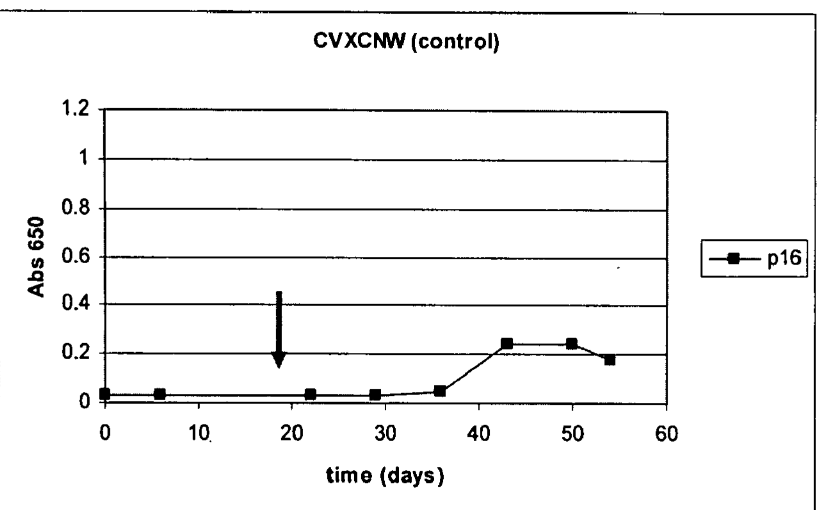
FIGS. 9A-B demonstrate detection of antibodies specific for *E. canis* using a polypeptide shown in SEQ ID NO:10 in two dogs that have not been vaccinated for *E. canis* over a time course of infection.
Figure 9B:
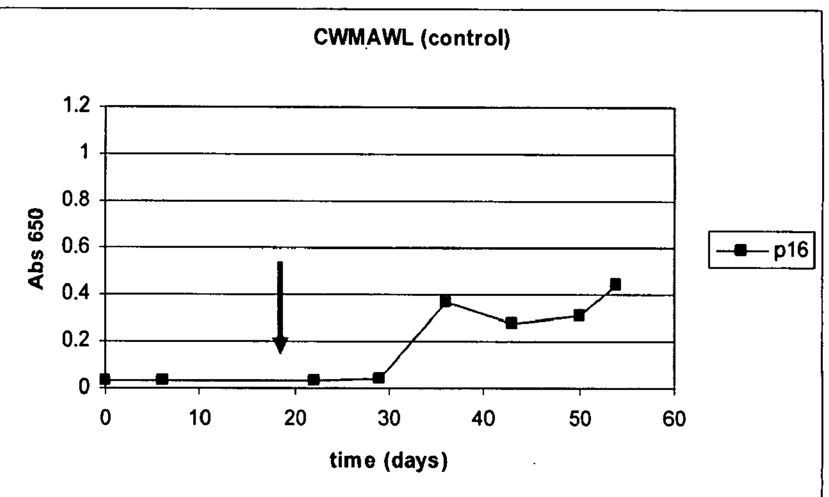
Figure 10A:
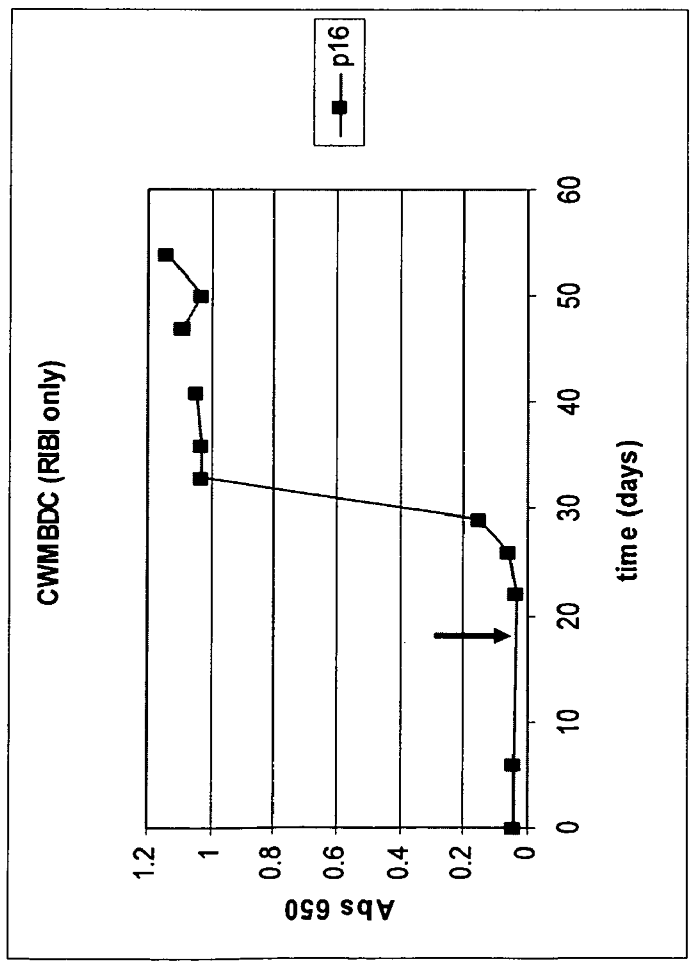
FIGS. 10A-C demonstrate detection of antibodies specific for *E. canis* using a polypeptide shown in SEQ ID NO:10 in three dogs that have been vaccinated (RIBI adjuvant) for *E. canis* over a time course of infection.
Figure 10B:
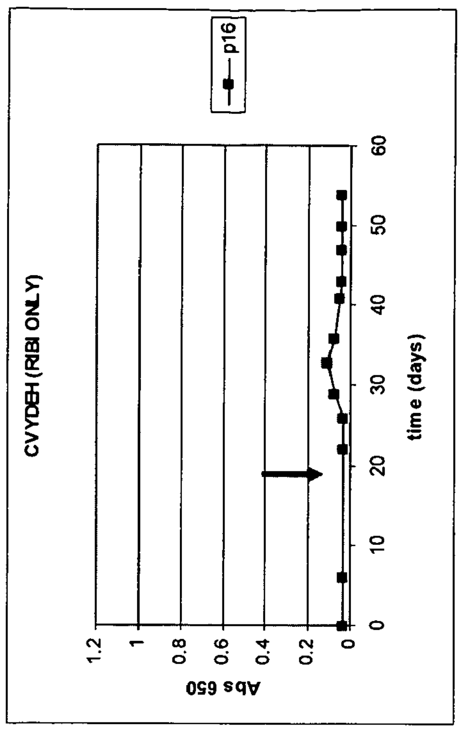
Figure 10C:
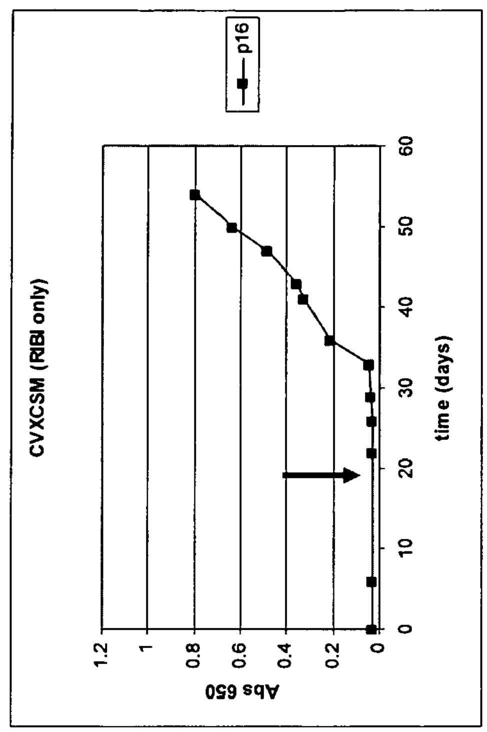
Figure 11A:
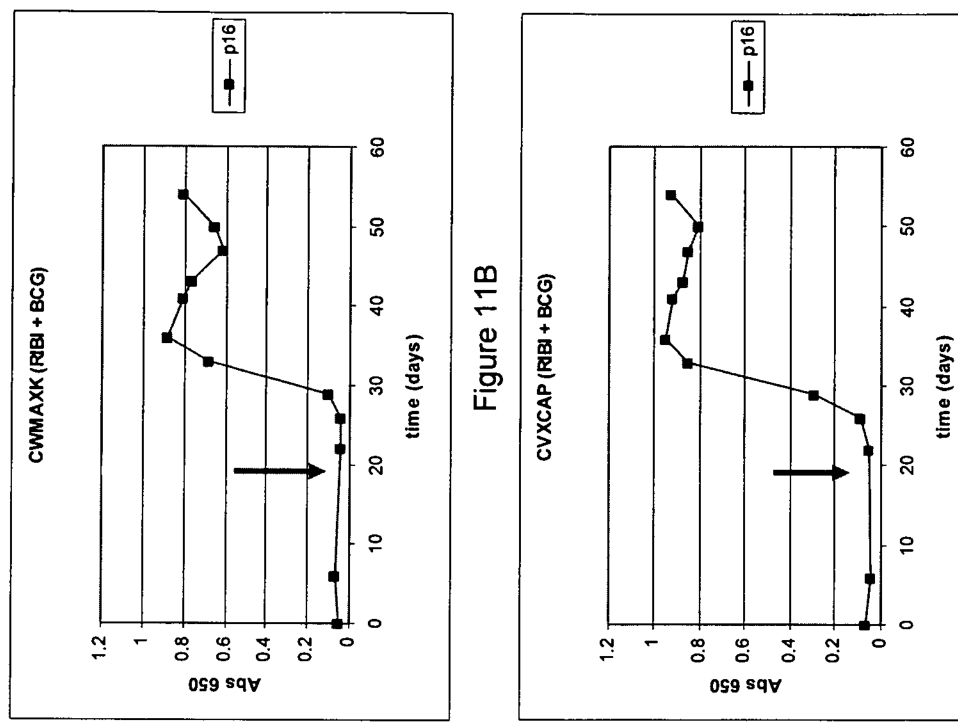
Figure 11A:
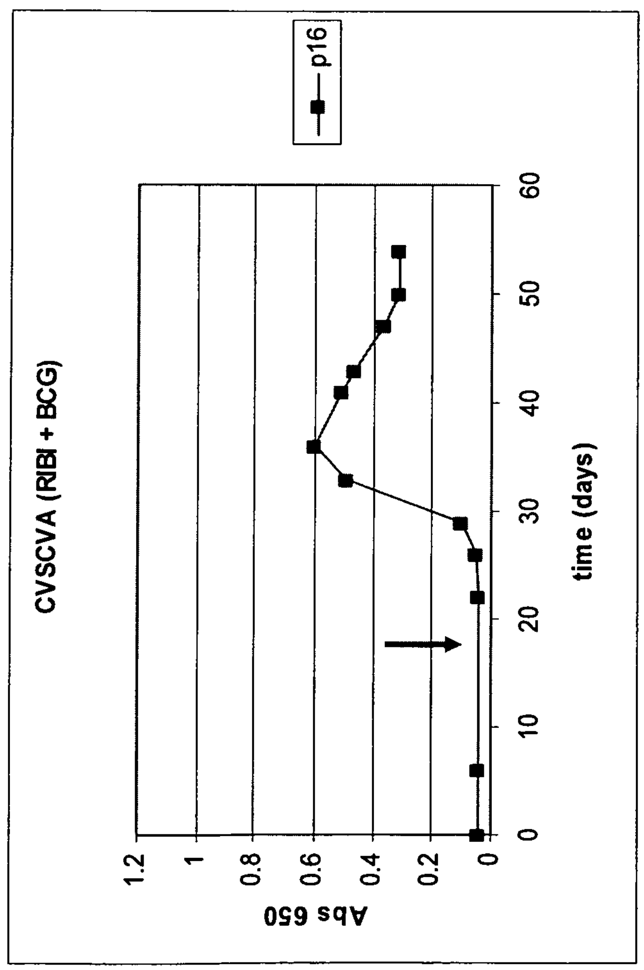

The results are shown in FIG. 8. The E-1, E-2, E-3, E-4, E-5, and E-6 dogs were experimentally infected with *E. canis*, but were not treated for the infection. FIG. 8 demonstrates that the level of antibodies that bind to SEQ ID NO:23 increased considerably after experimental infection and did not decrease during the time course of the experiment. The EDTx-1, EDTx-2, EDTx-3, EDTx-4, EDTx-5, and EDTx-6 dogs were experimentally infected with *E. canis* and then treated with doxycycline at 28 days-post infection. FIG. 8 demonstrates that the level of antibodies that bind to SEQ ID NO:23 increased considerably after experimental infection and decreased after administration of doxycycline. Therefore, SEQ ID NO:23 can be used to monitor the progression, the response to treatment, or the efficacy of treatment of *E. canis* infection.

Example 16 Differentiation of Dogs that have been Vaccinated for *E. canis* and Dogs that have been Vaccinated for *E. canis*, but have Become Infected with *E. canis*

Vaccines may not be completely effective at preventing infection. Therefore, it is desirable to have a method to determine if a vaccinated animal has become infected despite the vaccination. Immunoassays using p16 as a detection agent do not detect anti-*E. canis* antibodies in dogs that have been vaccinated for *E. canis* and that are not infected with *E. canis*. It has now been discovered that an *E. canis* p16 protein (SEQ ID NO:10) can be used to detect *E. canis* infection in dogs that have received an *E. canis* vaccine.

Six dogs that had been vaccinated for *E. canis* and two unvaccinated dogs were challenged with *E. canis* infected K9 cells in 10% DMSO. Each dog was tested over time for anti-*E. canis* antibodies with an immunoassay comprising SEQ ID NO:10. All of the vaccinated dogs and the two control dogs became infected with *E. canis*. The *E. canis* infections were confirmed with two independent infection markers. The immunoassays were able to detect the *E. canis* infection in the vaccinated and non-vaccinated dogs. All of the immunoassay signals were significantly above background signals. See FIGS. 9A-B, 10A-C, and 11A-C.

Sequences:

```
SEQ ID NO: 1 120kDa Antigen Nucleotide Sequence
ORIGIN
   1 ATGGATATTG ATAACAATAA TGTGACTACA TCAAGTACGC AAGATAAAAG TGGGAATTTA

  61 ATGGAAGTGA TTATGCGTAT ATTAAATTTT GGTAATAATT CAGATGAGAA AGTAAGCAAT

 121 GAAGACACTA AAGTTCTTGT AGAGAGTTTA CAACCTGCTG TGAATGACAA TGTAGGAAAT

 181 CCATCAAGTG AAGTTGGTAA AGAAGAAAAT GCTCCTGAAG TTAAAGCGGA AGATTTGCAA

 241 CCTGCTGTAG ATGGTAGTGT AGAACATTCA TCAAGTGAAG TTGGGAAAAA AGTATCTGAA

 301 ACTAGTAAAG AGGAAAGTAC TCCTGAAGTT AAAGCAGAAG ATTTGCAACC TGCTGTAGAT

 361 GGTAGTATAG AACATTCATC AAGTGAAGTT GGAGAAAAAG TATCTAAAAC TAGTAAAGAG

 421 GAAAGTACTC CTGAAGTTAA AGCAGAAGAT TTGCAACCTG CTGTAGATGA TAGTGTGGAA

 481 CATTCATCAA GTGAAGTTGG AGAAAAAGTA TCTGAAACTA GTAAAGAGGA AAATACTCCT

 541 GAAGTTAAAG CAGAAGATTT GCAACCTGCT GTAGATGGTA GTATAGAACA TTCATCAAGT

 601 GAAGTTGGAG AAAAAGTATC TAAAACTAGT AAAGAGGAAA GTACTCCTGA AGTTAAAGCA

 661 GAAGATTTGC AACCTGCTGT AGATGATAGT GTGGAACATT CATCAAGTGA AGTTGGAGAA

 721 AAAGTATCTG AAACTAGTAA AGAGGAAAAT ACTCCTGAAG TTAAAGCAGA AGATTTGCAA

 781 CCTGCTGTAG ATGGTAGTGT GGAACATTCA TCAAGTGAAG TTGGAGAAAA AGTATCTAAA

 841 ACTAGTAAAG AGGAAAGTAC TCCTGAAGTT AAAGCAGAAG ATTTGCAACC TGCTGTAGAT

 901 GATAGTGTGG AACATTCATC AAGTGAAGTT GGAGAAAAAG TATCTGAAAC TAGTAAAGAG

 961 GAAAATACTC CTGAAGTTAG AGCAGAAGAT TTGCAACCTG CTGTAGATGG TAGTGTAGAA

1021 CATTCATCAA GTGAAGTTGG AGAAAAAGTA TCTGAAACTA GTAAAGAGGA AAGTACTCCT

1081 GAAGTTAAAG CAGAAGATTT GCAACCTGCT GTAGATAGTA GTATAGAACA TTCATCAAGT

1141 GAAGTTGGGA AAAAAGTATC TGAAACTAGT AAAGAGGAAA GTACTCCTGA AGTTAAAGCA

1201 GAAGATTTGC AACCTGCTGT AGATGGTAGT GTAGAACATT CATCAAGTGA AGTTGGAGAA

1261 AAAGTATCTG AAACTAGTAA AGAGGAAAAT ACTCCTGAAG TTAAAGCAGA AGATTTGCAA

1321 CCTGCTGTAG ATGGTAGTGT AGAACATTCA TCAAGTGAAG TTGGAGAAAA AGTATCTGAA

1381 ACTAGTAAAG AGGAAAATAC TCCTGAAGTT AAAGCGGAAG ATTTGCAACC TGCTGTAGAT

1441 GGTAGTGTAG AACATTCATC AAGTGAAGTT GGAGAAAAAG TATCTGAAAC TAGTAAAGAA

1501 GAAAGTACTC CTGAAGTTAA AGCAGAAGAT TTGCAACCTG CTGTAGATGA TAGTGTAGAA

1561 CATTCATCAA GTGAAGTTGG AGAAAAAGTA TCTGAAACTA GTAAAGAAGA AAGTACTCCT

1621 GAAGTTAAAG CGGAAGATTT GCAACCTGCT GTAGATGGTA GTGTGGAACA TTCATCAAGT

1681 GAAGTTGGAG AAAAAGTATC TGAGACTAGT AAAGAGGAAA GTACTCCTGA AGTTAAAGCG
```

-continued

```
1741 GAAGTACAGC CTGTTGCAGA TGGTAATCCT GTTCCTTTAA ATCCTATGCC TTCAATTGAT

1801 AATATTGATA CTAATATAAT ATTCCATTAC CATAAAGACT GTAAAAAAGG TTCAGCTGTA

1861 GGAACAGATG AAATGTGTTG TCCTGTATCA GAATTAATGG CTGGGGAACA TGTTCATATG

1921 TATGGAATTT ATGTCTATAG AGTTCAATCA GTAAAGGATT TAAGTGGTGT ATTTAATATA

1981 GATCATTCTA CATGTGATTG TAATTTAGAT GTTTATTTTG TAGGATACAA TTCTTTTACT

2041 AACAAAGAAA CAGTTGATTT AATATAA
```

SEQ ID NO: 2 120kDa Antigen Protein Sequence
ORIGIN

```
  1 MDIDNNNVTT SSTQDKSGNL MEVIMRILNF GNNSDEKVSN EDTKVLVESL QPAVNDNVGN

 61 PSSEVGKEEN APEVKAEDLQ PAVDGSVEHS SSEVGKKVSE TSKEESTPEV KAEDLQPAVD

121 GSIEHSSSEV GEKVSKTSKE ESTPEVKAED LQPAVDDSVE HSSSEVGEKV SETSKEENTP

181 EVKAEDLQPA VDGSIEHSSS EVGEKVSKTS KEESTPEVKA EDLQPAVDDS VEHSSSEVGE

241 KVSETSKEEN TPEVKAEDLQ PAVDGSVEHS SSEVGEKVSK TSKEESTPEV KAEDLQPAVD

301 DSVEHSSSEV GEKVSETSKE ENTPEVRAED LQPAVDGSVE HSSSEVGEKV SETSKEESTP

361 EVKAEDLQPA VDSSIEHSSS EVGKKVSETS KEESTPEVKA EDLQPAVDGS VEHSSSEVGE

421 KVSETSKEEN TPEVKAEDLQ PAVDGSVEHS SSEVGEKVSE TSKEENTPEV KAEDLQPAVD

481 GSVEHSSSEV GEKVSETSKE ESTPEVKAED LQPAVDDSVE HSSSEVGEKV SETSKEESTP

541 EVKAEDLQPA VDGSVEHSSS EVGEKVSETS KEESTPEVKA EVQPVADGNP VELNEMESID

601 NIDTNIIFHY HKDCKKGSAV GTDEMCCPVS ELMAGEHVHM YGIYVYRVQS VKDLSGVFNI

661 DHSTCDCNLD VYFVGYNSFT NKETVDLI.
```

SEQ ID NO 3 200kDa Antigen nucleotide sequence from 1081 to end
ORIGIN

```
   1  AATTTAGAT TTTGGACTTG TAGATGGAGA TGGTAAAAAT CCTTTACATC ATGCTGTTGA

  61 ACATTTGCCA CCTGTTATAC TTAAGGGCGT AATGGACCAT GTAAAAAATA GTAGTGAGTT

 121 TCAAGATTTA GTAAATGATC CTGATTATTT TGGAAATACT ATAGCTCATT ATGCAGTTAA

 181 GAATAAAAAT GCTGATTTAA CATTGTTTAA CATGCTGAAA GCTTCAGGAG CTGATTTAAA

 241 TGTTAGGAAT GTAGTTGGTC GAGCTCCAAT ACATGTTGCT TCTTCTAATG GTAAGGCTAA

 301 TGCAGTTTCT GGACTTGTAT CATGTGGTAT TGACGTTAAT TCTCAAGATG TGAATGGAGA

 361 TACACCACTT CATATTGCTG TTGAAGGCGG TAGTATGGAG ACGGTATTAG CAGTGTTAAA

 421 TCAGAGAGGT GCTGATGTTA GTGTCCAGAA TAACGATGGA GTTACACCTA TGCTTAGTGC

 481 TGCTAAATAT GGAGATATAG GTGTAATAAA AGCTTTAGGT TCAGCTAAAC CAAATATTAA

 541 AGGTGAAGAC ACTGTTGCTA AATCATTGCT GATGGAGGAT TACAAAGGTT TTACACCCTT

 601 GCATTTTGTA GCTGGTGGTG GTAGCAGAGA TACATTCCGT GTCGTAAGAA AAAATTATGA

 661 AAAATGTCAT GACTTAGCTA CTATTAGGGC AGCTTTAATG CAAGATAGAA GTGGTGGTGA

 721 GCTTGTAAAT TTAGGGGATT TTGAAAGTGA AAATATATTG GGTTCGCCAA ATGCAAAATT

 781 CTTGCAGCAT ATTCAATCAG CAAATTTTGG TTTTTCTCCA GCGCATTGTG CTATAGTATC

 841 GTCTAATCAC AATGTAATGA AAGATATCTT AAATTTTGTT GGGGATTCGT TACACCTACC

 901 AAGTGAGCGT GGGTATAATG CAATGCAGGT TGCTGCTTTG TTTGGTGACA AAGAAGCAGT

 961 GAAAATGCTT GCTAAAAGTG CTAAGCCAAG TGATCTTAAT TTTAAGACTT CAGCAACTCC

1021 TACTCCGTTA AATCTTGCAT GTCTTAGAGG TGATAATGAG GTAGTACGTG GGTTAGTAGG

1081 TCAACATGGT ATTGACATTA ACCAACGTAT GGGAAGTGAT AAAAACACTG TATTGCATTA

1141 TGCAATCAGC AAAGGAGATA GTTTTCTTGT GCAAAAGATA TTAGCTCATA CTGGAGTTGA
```

-continued

```
1201 TGTTAATTGT GAGAATAACC TAGGTCAAAC GCCTTTACAT TTAGCAGTTG AGGGAGGAGA
1261 TCCTAAGATA GTATCTTCTC TTCTTAAAGC TGGTGCAGTA GTTAATCGTC TGGATGATAA
1321 TGGTAGATCT GTACTTTCTT CTGCGATAGT TCCAGGTAGA AAAGAAAAGG GAGTGCTGGG
1381 TATAGTTAAT AAATTGCTGG ATAGAGGTGC AGATATTAAT TTAGATGGAG ACCACAATAT
1441 ACTTTTTGAT CAGTGTCTAA GGGGTGGATA TAATAATGTA TTAGATAAGT TAATACAACA
1501 AGGGGTTGAA GTTAATCGAA ATAGTGAAAT ACGTCCAATG GTTTATGCTG CAATATCTGG
1561 TAATGAGCAT GCTATCAAAT CATTAGCTAA TGCTGGTGGA GATGTTAATG AAGTAGTAAA
1621 TAATCCATCT AGTAGGCATT CAGGAAATCC TTTAATTATG GTTGCAGTAG CAGATGGTAA
1681 TGCAGGTCTT CTTAAAACAT TAGTTTCTGA AGGATGTGAT GTTGGTAAAT CTGGAAAAGA
1741 TGGTAATACA GCGTTACATT ATGCTGTTAG TCATTCAGAT AAAGAGTTTG GTAATAAAGC
1801 TATAAAGATA TTAATTTCAC GTAATAGTGT TGGGACTAAT AGAGATATTC TTACTCAAAA
1861 GAATAACGCA GGTGATACAC CTTTACATGA AGCTCTTAAG TCAGGTAATA TTAATTCTGT
1921 ACAGAATATC TTAAGTGCTG TACATCCAAG ATACGCAAAG GAGATATTAA CAGCCAGAGA
1981 CAAAGAAGGG TACACACCAA TGCATTATAC TGTTGGAGTA AATAATGTTG ATGTTGGTAG
2041 AAGTATTCTA GAGTCTATGC TCTCTAAAGG TGTGAATAAT CTTGGAGAGA TTGTTGGAGC
2101 ACAGGATAGT AATTTTCGAA CACCTCTGCA TGCTGCTATT AAAATATCTG ATTATCGTGC
2161 TGCGGACATG ATAATAGGTA GCTTATCGAA AACAGAATTG TCAAAGTTAT CGCAATTAAC
2221 AGATATTAAC GGGGATACAC CACTACATCT TTCTTGTCAG TCTGGTAATG TCGAGATGAC
2281 ACAATTCTTT CTTGGAGGTT TGGATAAACG TGAATTACCT AAGACATTAA AGATAGCAAA
2341 TAAAAATGGA GATACTCCTT TACATGATGC TATAAGAAAT GATGATATTA AATCTGCAAA
2401 AATGATGATT AGGAATTGTA ACAAAGAAGA ACTTGCTAAT GTATTAAAAT GTAAAGATAG
2461 TTTTGGTAAT ACAGTATTGC ATACTATTGC TGACCAAGTT ATTGCGAATC CAGAATCAAA
2521 GAAAGACCTT GATGGTTTGA TGAATTTAGC AGTGAAAAGG CTAAAGAATC AAGATCTGAA
2581 AGATCTAGTT AATACGCGAA ATAACTCTGA CGATACTGTT GCACATTGTG CTCTTTTATC
2641 GGATATGAAA TATGCTCAAA AGATACTTAA ATCATGTAAC CATGATACAT TAGTGAGAGG
2701 AAATAGTAAT AATCAATCTT TATCAGAGTG TATTCGTGAT GATAGTAAAT ATAAAAAAGG
2761 TGGAATTTTT AGTAAGTCTT TATTTTCAAA ATTAAAGAAA CTTGAGGCAC GAGCTGCCAG
2821 CGCTAGTTAT GAAGAATTAT CTAGTATCAG TAGTGGTAGT GATGTTTCTT CTGTATCAAC
2881 AAATAGCACA GAAGTAAGTG CAGTACCTGA AGTGGCAAGA AGTAGTGGTG CTGTGTCGTT
2941 CAAACATGTG CAAGAAACAG GAGTTGACAC GTCTGGTCCT TCTGATATAG AAAGTTTAGA
3001 GAGATTATCT GATACTAGTC TTGGGTCAAA TGATTTTGAT CAGCGAATGG CAGATTTAGA
3061 TCAAGAAATA GCAAATATTG TTAGTGGTTT ACCAGAAGTT ACCCAGGTAG CTGTAAGTCA
3121 ACAACAAGCA GCATCTCCTA GTTCAGGTCA AGCTGCTGGT GTGCAACAAA AAGAGATGCA
3181 GAGATAA
```

SEQ ID NO: 4 200kDa Antigen Partial Protein Sequence
ORIGIN

```
  1 NLDFGLVDGD GKNPLHHAVE HLPPVILKGV MDHVKNSSEF QDLVNDPDYF GNTIAHYAVK
 61 NKNADLTLFN MLKASGADLN VRNVVGRAPI HVASSNGKAN AVSGLVSCGI DVNSQDVNGD
121 TPLHIAVEGG SMETVLAVLN QRGADVSVQN NDGVTPMLSA AKYGDIGVIK ALGSAKPNIK
181 GEDTVAKSLL MEDYKGFTPL HFVAGGGSRD TFRVVRKNYE KCHDLATIRA ALMQDRSGGE
241 LVNLGDFESE NILGSPNAKF LQHIQSANFG FSPAHCAIVS SNHNVMKDIL NFVGDSLHLP
```

-continued

```
 301 SERGYNAMQV AALFGDKEAV KMLAKSAKPS DLNFKTSATP TPLNLACLRG DNEVVRGLVG

 361 QHGIDINQRM GSDKNTVLHY AISKGDSFLV QKILAHTGVD VNCENNLGQT PLHLAVEGGD

 421 PKIVSSLLKA GAVVNRLDDN GRSVLSSAIV PGRKEKGVLG IVNKLLDRGA DINLDGDHNI

 481 LFDQCLRGGY NNVLDKLIQQ GVEVNRNSEI RPMVYAAISG NEHAIKSLAN AGGDVNEVVN

 541 NPSSRHSGNP LIMVAVADGN AGLLKTLVSE GCDVGKSGKD GNTALHYAVS HSDKEFGNKA

 601 IKILISRNSV GTNRDILTQK NNAGDTPLHE ALKSGNINSV QNILSAVHPR YAKEILTARD

 661 KEGYTPMHYT VGVNNVDVGR SILESMLSKG VNNLGEIVGA QDSNFRTPLH AAIKISDYRA

 721 ADMIIGSLSK TELSKLSQLT DINGDTPLHL SCQSGNVEMT QFFLGGLDKR ELPKTLKIAN

 781 KNGDTPLHDA IRNDDIKSAK MMIRNCNKEE LANVLKCKDS FGNTVLHTIA DQVIANPESK

 841 KDLDGLMNLA VKRLKNQDLK DLVNTRNNSD DTVAHCALLS DMKYAQKILK SCNHDTLVRG

 901 NSNNQSLSEC IRDDSKYKKG GIFSKSLFSK LKKLEARAAS ASYEELSSIS SGSDVSSVST

 961 NSTEVSAVPE VARSSGAVSF KHVQETGVDT SGPSDIESLE RLSDTSLGSN DFDQRMADLD

1021 QEIANIVSGL PEVTQVAVSQ QQAASPSSGQ AAGVQQKEMQ R.
```

SEQ ID NO: 5 ATPase - Clone 84 Fragment Nucleotide Sequence
ORIGIN

```
   1 AATTATGCTG AAACTACTTT ATCATTTGGT GAATCTCGAG CAGAAGGACG TGAATCTCCA

  61 TCAAGTGCAT TTGTTCAAAC TGGTCAATCA GAAGTACCTC GGAGTGAGGC TGCAGAGCCA

 121 TTAATTCAAT TTCCTCATGA TGAAGAAAGT ACTGCATTAG GTTCTCAAGC AACTATGACA

 181 GGAGTGTCTA CTCAGGCTAG TCCGTCAGCA GCATATCAGG ATGATAGTGA AATATCACGT

 241 ATGAGGTCTA TGGCAGGAAC ATCTGCTCAA GCTGATCAAT CAGCAGTACA TCGTCGGAGT

 301 GGTACAGCAT TAGAGCCATT AATTGAATTG CCTGATGAAG AAGAAAATGC TGCATTAGAT

 361 TTTCAAACAG CTATGACAGG AGTGCCTACT CAGGCTAGTC CGTCAGCAGT ACATCGGAGT

 421 GGTGTTGCAT CAGATCCTAC GCTACCTGAT GATGAAAGAA TTGATGTTCC ATCAGTTTCA

 481 TCTCAAGTTG TAAGACCTTT TAGTGATGGT GAAGATTATT CAGTATATGA TAAATCAGGT

 541 GTAGTAAGTG GTCATGAAAG ACCTGTTTCT TCTAGAGATT CAAGACAATT GGATGCATTT

 601 GGTGATCCAT CAGATGATTT ATTGCCGGAG AGTGAAATTA TTGTTAGCAG CAGTAAGAAA

 661 GCAATATTAG ATAGCCAAAA TGAAATAGAA TCTCTTATTC AGAGTGGAGA TACTTCTAGA

 721 TGTATTAGGG CAATTAATAG TGCTCCTAGT GCGTCAGTGT TTCAACTGAA GACTTTATCG

 781 AATGATATAT CTATTGCTGG ACGTGCTTTT TTAAATGGTA ATATTGATTT AATAGAAGCT

 841 TGTATGAATT CTGGCAAGAA ATTAAATCCA AATATTACTG ATAATGAAAA AAATACTCTA

 901 TTACATCAAT TTGTAGGATA TTTTGAACGC GATCCGAGAA TGTTGCTTGA TGCAGGAATG

 961 CGTAATCTGT TTTTGAGATT ATGCATGGAT TATGGTTTCG ATATTAATCA TAAAAATAGT

1021 AATGGTAATA CAGTACTTGA TAGATTAAAT GATTTAGTAG AAGGGTTAAG TAGTTCGCAA

1081 GTTGATCTTG AAAGTAGTGG TATTGATGAG TTTATGATCT CATTGTTAGC TCATTCTAGA

1141 ATGAGTGATC AAGCAGTAAA GAATATTGCT ACTGCGCAAA ATGAGTTTTT TGCACGTGAT

1201 TCTGTTTATA ATATTAGTCG TTTAGTTGAT ACTTCTATAG TTTTGCAGAA TAAATTCAGT

1261 GAAGTATTTT ATGAAGTCTG TGGACGTATT TTATCTGAAG AAGCTGGTAA ACATAAGGGT

1321 GTTGCTGAAG CAAATTATTC AAGATTGAAT AAAATATTAA ATGATGAATG TCTTAGAAAG

1381 ACTTTAGCTA ATACAGATGC CGATGGAAAT AATGTTTTAC AGAGATTGTG TCAAGATATT

1441 GCTTCTGGAA AAATCAATGC TCGTGATGAC AGAGTATTAA AACTTTTTGA GACAATTATA

1501 TCTAATTTAA AAGACAAAGA TAAAGCATTA CTAGAGGATT TATTATTTAA TAATAGAAAC
```

-continued

```
1561 TCAAGATTTG AAAATTGCAT TGAAGCTATA CCACGTATTC CTGGTGCCGA TGCTCTATTT
1621 AAAAAACTAG AAGAGTTATT ATTAAAAAAG AAAATAGCAG AGTCTTGTGA TTTTAATTCT
1681 ATGTTAGTGA ATTGTGCTGA GTCTGCTAAT GATAATTTAT ATAATTACCT GCGCACTAAT
1741 TATGCAGTTA TTGGTATAAA TAACGTAGAT ATAAATGGCA ATTCATCCCT ATGTAAAGCT
1801 GTTGTTACTG GGTCACAAGG TATTGTTAAA GCAGTATTAT CAACTGGAAC TAATATTAAT
1861 AGGAAAGATA AAAATGGTAA TACACCTTTA CATGCATTGT TAATTTTTAT GATGTCTAAC
1921 CCTGAACTTG TCAAGGAGCA ACATATTTCA CTTGTGAAAT TCTTAGCGTC TCGTGGAGCT
1981 TTACTTAATG TAAAAAATAA TATGAATATT TCTCCAATTA TGCTTGCAGA ATCTATTGAT
2041 AAGAAAGAGG AACTTGCTAA GAAATTTACA AATCAAAAAG TTAGTATTTT AGAATCTTTA
2101 ATAGCTGGTA GTGAAGAACA TTTAGGGCTT AAATCCAAAT GTATATCTGA GTTAAAGCCT
2161 TATATAGAAT TAGGAAAAGG CATGAAGTAC GAAGATATAC ATGCTGATGT AATAGGTGGT
2221 GTATTATCTG CTGATATGTG TAATGCTAGA TTGCAGATAG GTAAATTATT AAATGGTGAT
2281 TTTTGTAAAG AAAATGAATT AAAGACAGTA AAATTTAATT TTTCTGATAC AAATAAGGGT
2341 TATGTACAAA ATGTTGGTAA AAAAAGAAAT TAT
```

SEQ ID NO: 6 ATPase - Clone 84 Fragment Protein Sequence
ORIGIN

```
  1 NYAETTLSFG ESRAEGRESP SSAFVQTGQS EVPRSEAAEP LIQFPHDEES TALGSQATMT
 61 GVSTQASPSA AYQDDSEISR MRSMAGTSAQ ADQSAVHRRS GTALEPLIEL PDEEENAALD
121 FQTAMTGVPT QASPSAVHRS GVASDPTLPD DERIDVPSVS SQVVRPFSDG EDYSVYDKSG
181 VVSGHERPVS SRDSRQLDAF GDPSDDLLPE SEIIVSSSKK AILDSQNEIE SLIQSGDTSR
241 CIRAINSAPS ASVFQLKTLS NDISIAGRAF LNGNIDLIEA CMNSGKKLNP NITDNEKNTL
301 LHQFVGYFER DPRMLLDAGM RNLFLRLCMD YGFDINHKNS NGNTVLDRLN DLVEGLSSSQ
361 VDLESSGIDE FMISLLAHSR MSDQAVKNIA TAQNEFFARD SVYNISRLVD TSIVLQNKFS
421 EVFYEVCGRI LSEEAGKHKG VAEANYSRLN KILNDECLRK TLANTDADGN NVLQRLCQDI
481 ASGKINARDD RVLKLFETII SNLKDKDKAL LEDLLFNNRN SRFENCIEAI PRIPGADALF
541 KKLEELLLKK KIAESCDFNS MLVNCAESAN DNLYNYLRTN YAVIGINNVD INGNSSLCKA
601 VVTGSQGIVK AVLSTGTNIN RKDKNGNTPL HALLIFMMSN PELVKEQHIS LVKFLASRGA
661 LLNVKNNMNI SPIMLAESID KKEELAKKFT NQKVSILESL IAGSEEHLGL KSKCISELKP
721 YIELGKGMKY EDIHADVIGG VLSADMCNAR LQIGKLLNGD FCKENELKTV KFNFSDTNKG
781 YVQNVGKKRN Y
```

SEQ ID NO: 7 ATPase - Clone 7 Fragment Nucleotide Sequence
ORIGIN

```
  1 GTAAAAAAAT TAAGATTATT ATTAAATTCA ATAAGTGAGT TACCGCAAGA ATTAAAAGAT
 61 CAAATTTTAA GTACTAGAAG TACTATAGAT AAATTACGAA ATAGAATTAA TGCCTGCATA
121 AAGTCTGACG ATAGAGAAGG TATTGCACAT GCTGTAGAAT CTATGGCTAG TTCTTATTGT
181 GAATTATTAG GACATTGTAG ATTAATTTTT AAGAAATTAT ATGATGAAAA TGCTGATAAA
241 AGTTTGCTAG AATTATGTAT TAAAGAATAT CAATCTGATT TAAACAAATT ATTGGAACAA
301 GGTATTGATA TATGTGCTTC AGAAGTCTCA TCAGAATGTA AGGATTTAGT TTGTAAAGTA
361 TGTGAAGATG AATTTGAGAA ATATGACTCT TTATCTAAAG TACAAAGATT CAGGGAATTA
421 TCTGGTGAAA TTGCTGATTT GGATGATAAA TTAACAAGAA GGGCTTCTTT TGTTGAGACT
481 TTTGGATTAT TTAGCAGTAG ATTAAGACAT TATAGGGAAA TTTTAGGAGA TGGTGATTTA
541 AAATTTCGAG AGAGGATAGT TGAAAAATAT CAAGAGGATT TAAAGGAATT ATTAGAATTA
```

-continued

```
 601 TCTGTTGATC TTCATTTGTT AATAAATTTA CCAGCATTAG AAGATTTACG CGATCATAGA
 661 AATTTAGTGC ATAGAGCATG TAATGCTGAA ATTGAAAAAT ATCTAACTTT ATTTGATGAT
 721 CAACAATTAC GTACATTATC GCAAGAAGTG AATAATGCTC ATGGTGAATT GATACAGATG
 781 TTTTCTAAGT TTAGTATATT TGTTGATGGC GTTACTGGTA TTGAACAGAG CACATCTCAA
 841 GTAGAGCACC CTCGTTCTGA TATTGCTAAA AGAGATACTA CAACACCAAA GCAACGTGTT
 901 GTGCAAGGTA AAGATGATAT ACAATCTAGT GATAGTGATA GTGATAGTGA TAGTAAATAC
 961 GGTGATGATG ATAGTAAAAA AGCATCAGTT AGTGCACCTG CTGTTGACCA AGTTGTACCT
1021 GTAGCTGATG TTCAACCTGA ACCTCAGCTA GGTGAAGGAT TGGAAACATT AGAGTCTAGT
1081 ATAGCTGAAG GACCTGAGTT GCCTGGTGAT GCATCTACTG CTAAGCAATC TATACCTTTT
1141 GCGATAACAC CATCAAGTCC TGAGACAGTT GATGAAAAAC TTGAAAGTTC TGGTGTTAGT
1201 CAAGATGGTA TTACAACACC AGGACAACGT GTTGTGCAAG GTAAAGATGA TATACAATCT
1261 AGTGATAGTG ATAGTGATAG TAAATACGGT GATGATGATA GTAAAAAAGC ATCAGCTAGT
1321 GCACCTGCTG TTGACCAAGT TGTACCTGTA GCTGATGTTC AACCTGAACC TCAGCTAGGT
1381 GAAAAATTGG AAACATTAGA GTCTAGTATA ACTAAAGGAC CTGAGTTGCC TGGTGATGCA
1441 TCTACTGCTA AGCAATCTAT ACCTTTTGCG ATAACACCAT CAAGTCCTGA GACAGTTGAT
1501 GAAAAACTTG AAAGTTCTGG TGTTAGTCAA GATGGTATTA CAACACCAGG ACAACGTGTT
1561 GTGCAAGGTA AAGATGATAT ACAATCTAGT GATAGTGATA GTGATAGTAA ATACGGTGAT
1621 GATGATAGTA AAAAAGCATC AGCTAGTGCA CCTGCTGTTG ACCAAGTTGT ACCTTCTGAC
1681 ACTCGTGCAG ATGGAGTATC AGAACCATTA GCATCTCATG TGGATCAAGG ATCTGATGTA
1741 CCTGGTGATG CATCTGTTGA TGGTGTTGAT TTAAGATTAG GACGGTTATC TACTGAGCAA
1801 AGTGGATTGT TGCCACGTCA TGAACAAAAT GTAAGAGCAT TTATTTTAGA ACAGAGTTTG
1861 TTAGATCAAT TATATATGGA CTATATAGAT TTACACCCTG ATCAGAAAAG TTGTGAAGCT
1921 TATAATTCAG CATTGCATGG ATATAATACA AGATTAGAGT TACAGAAGGA ATATAACAGG
1981 ATTTTTGAAT CACATGAATC AGCATCTCCA AATGAAATTA ATAGTTTTTC ACAAAAATAT
2041 AGAGCAGCAT TAAGAGATGT TGCGCAGGAT ATTGTTAATC AGGGTCCAAT GTTTTATTCT
2101 TCTAGAGATG CAATGCTATT AAGGGCTAGA GTAGACACAT TGTGTGATAT GTGTCGTTCA
2161 ATACGTAATC TGTATATGGT TGAATTAGAT GCCATAGATA AAGAAGAAAA ATCGTTACAA
2221 TCTGATATGA AATCTGCAAG TTCTAGTGAT AAAAAGTTGA TACAAGAAAA AATAAAATTA
2281 CTT
```

SEQ ID NO:8 ATPase - Clone 7 Fragment Protein Sequence
ORIGIN

```
  1 VKKLRLLLNS ISELPQELKD QILSTRSTID KLRNRINACI KSDDREGIAH AVESMASSYC
 61 ELLGHCRLIF KKLYDENADK SLLELCIKEY QSDLNKLLEQ GIDICASEVS SECKDLVCKV
121 CEDEFEKYDS LSKVQRFREL SGEIADLDDK LTRRASFVET FGLFSSRLRH YREILGDGDL
181 KFRERIVEKY QEDLKELLEL SVDLHLLINL PALEDLRDHR NLVHRACNAE IEKYLTLFDD
241 QQLRTLSQEV NNAHGELIQM FSKFSIFVDG VTGIEQSTSQ VEHPRSDIAK RDTTTPKQRV
301 VQGKDDIQSS DSDSDSDSKY GDDDSKKASV SAPAVDQVVP VADVQPEPQL GEGLETLESS
361 IAEGPELPGD ASTAKQSIPF AITPSSPETV DEKLESSGVS QDGITTPGQR VVQGKDDIQS
421 SDSDSDSKYG DDDSKKASAS APAVDQVVPV ADVQPEPQLG EKLETLESSI TKGPELPGDA
481 STAKQSIPFA ITPSSPETVD EKLESSGVSQ DGITTPGQRV VQGKDDIQSS DSDSDSKYGD
541 DDSKKASASA PAVDQVVPSD TRADGVSEPL ASHVDQGSDV PGDASVDGVD LRLGRLSTEQ
```

-continued

```
601 SGLLPRHEQN VRAFILEQSL LDQLYMDYID LHPDQKSCEA YNSALHGYNT RLELQKEYNR

661 IFESHESASP NEINSFSQKY RAALRDVAQD IVNQGPMFYS SRDAMLLRAR VDTLCDMCRS

721 IRNLYMVELD AIDKEEKSLQ SDMKSASSSD KKLIQEKIKL L
```

SEQ ID NO: 9: p16 Antigen Nucleotide Sequence

```
ORIGIN
   1 ATGTTACACG TTCAAAATCA TGTTGATCAA CATACAAATC ATATAGAACA TGATGATTAC

  61 CATTTTACTG GTCCTACTAG TTTTGAAGTT AATCTTTCTG AAGAAGAAAA AATGGAGTTA

 121 CAAGAAGTAT CTTCTATTGA TAGTGTAGGA TGCGAAGATT GTGATCCAAA TTGTCGTTAT

 181 CCTTTAGAAT TAGTAGAATG TCAGCGTATT GAGGAAAGAC CAGTATGCAA TGCAGGTTTA

 241 GAGAGCTTGA CTGTTGATGC ATATCAATTA GGATTGTTGT TAGGTGGTTT TTTAAGTGCT

 301 ATGAATTACA TATCTTATAG CTATCCTTGT TATTATTATG ATTGTTGTGA TAGAAATTAT

 361 TACGACTGTT GTCATAAGAA TGCGTGTTAT TACAACTGTT GTGATTGTGC GTAA
```

SEQ ID NO: 10 p16 Antigen Protein Sequence

```
ORIGIN
   1 MLHVQNHVDQ HTNHIEHDDY HFTGPTSFEV NLSEEEKMEL QEVSSIDSVG CEDCDPNCRY

  61 PLELVECQRT EERPVCNAGL ESLTVDAYQL GLLLGGFLSA MNYTSYSYPC YYYDCCDRNY

 121 YDCCHKNACY YNCCDCA.
```

SEQ ID NO: 11 Ribosomal Protein L1 Nucleotide Sequence

```
ORIGIN
   1 ATGACGATTT TCTTAGAAAG TGATGATGAT AAGAGTAACT TTAAGAAGAC ATTGGAGAAC

  61 GGTACTAAAG ACAAGACAAA TCTAGATAAT ACTTATTATG ACTATCATCA TGAAGATGAT

 121 ATGGGAAATA CTGAATATCA TTATGTGAGT TTGGATAGAG TGGATCATGT TAAGATGCCT

 181 GAAGAGCCTG TAGGTTATGG TGGAGATACT TTACCTATTG TTCCTACTAC AGCTGCTAGT

 241 GTATCTGGTA GTGATGCAGG CGTTGCTGTA GGTAATGTTA AAGATTTTGA AGATAATGTT

 301 TTTCATCATA CATCTACTAT AAGAAACGAT GAATTGAAGA TAGATTTACG AATACATACT

 361 TTAAAGGATT TATCTGATAA AAGATTACGT GAAATTGAAA AGGGATTTAA TGATACGGTA

 421 ACAAAATTTA AAAATAATTT TGGGTTAGAA CCAAATGATG GAGAAACTAT TTTTGATTTA

 481 TACCTTTTTG ATGATAAGGA ACAATATAAT TATTATGGAA AGCTTTATAA CTTAGGAATT

 541 AGTGGATCTG GAGGTATGAC TTTCTATGGA AATGCTAATG TTCCATATAA AATTTATGTA

 601 CATCAATATG GTGAAATATT GAATTTAAAA CATGAATTAA CTCATGCATT AGAAAGTTAT

 661 GCATCTGGAC ATAAATTGCA TGGTTCTGAC GTAAATAGCA GAATATTTAC GGAAGGATTA

 721 GCTGATTATA TCCAAGAAGA TAATAGTTTT ATTATGAGAG GATTAAAGGA TCGAGAGATC

 781 ACTTCAGATG TATTGAAAGA TTCTTCTGGT AATGTAGATC ATTTAAGTGG TGTTGCAGTG

 841 AATGAAAATC AGAGGTTAAG TTATAGTATA GGACATGCAT TTGTAAGCTT TTTACAAGAG

 901 AAATATCCTA AGTTAATTTC GGAATATTTA AACGCATTAA AAGAGGATAA TATTATTCGT

 961 GCTAAAGAAA TAATTAGTAT GGATAAGTAT CCAGATTTTG AGCCGTGGGT GAAGTCTAAA

1021 GACATTAGTT TATATTTAGA AAATATGAAT GTATTAAAGT TAGGATTAGG TGAGAAAATG

1081 TTTTCTGCTG AAAGTGCTAG CTATTTTGAA GATCAAGGTG TCAATAAAGA ATATTACCAT

1141 GAAAATATTT ATGATATGAG TGGTAAACTA GTAGGTGAAA TGTCACCTGT AGTGCATTAT

1201 GCACAAAAAA ATGTGATTCG TATTTGGAAT ATTGCAAGTC CTGATATGAT AGAGGTGCGA

1261 CCAGAATATA ACTTTCTGAA ATTGGTAACT ACTCCATCTG GTAAGTCTGC ATATGTATAT

1321 TGTGATAAGA ATGGGCATGA GTATTTTAAT ACTAAAGATT ACATAGATTC TGCGTTTAAT

1381 ATATTGGCAA GATATGATGT TAAGCTTCGT GAAAGTAGTG ATGCTTTGGA TATTAGAGGT
```

-continued

```
1441 CGTTACTCAG ATGCTGCTAA AGTGTTTAGT AAGCTGCCTA ATGCGGATTT GCTGTTGGAT

1501 AAGTTTTTAG AAAAAATAGG TTATAGTAGT TATAAGCAGA TAATAATGAG TAATCCAGAA

1561 CAGCTTAATT CTATTAAGGC TTATGTAGTA AAAGAAGTGT TTGAAAATTT TAGGGAATCT

1621 GAGGTCAAAA AGGTGTTGAG TGGTGAGTCT CATCCGGAAG TAAGAAATGT ATTAATGGAT

1681 CTTACCTATG TTGATTTAAA GAGTGTTATA GGAGTAAATG GTGCAGATAT TGACAGTATT

1741 ATTTCTAATC CAGATGTAAT GTTGCGTACT GCTGTGTTAG GTAAAGGAAA TGCAAGTGGG

1801 ATATCTCTAT ATGTAGATGA TCAGAAAGTT GGTGAGCTGT CAACTGAAGC AGGTTATTGT

1861 GTTAAAAATC TTGATACTGG TAAAGTGTAT TTTATGTTCC ATAATGTTGT TGGAATGATA

1921 GCAAGTGGTT ATGAAGACAG AGCATATATG GTTGTATTAG AAAAAGATGG TAAGTTTACT

1981 ACTGCTCTAG TTAATAATAT ACAAAAAGCA GCAGATGGAA ATGTTGTATG GGATAATCAA

2041 TTTAATCATC CGAATATTAA TAACTTGCAC TCAAATTATA AGGAGCTGTT GTTAAATGAT

2101 GCTTCAGTTA AAGATTACTC TCATCTTGCG GATGTGAAAT TTAATAAAGA TGATACAGTA

2161 ATTGTTAAAG GTGAATTATT AGATGATAAA GGTACTGTAA GTGTAGATGA TGATGTACAT

2221 CGTGCAGTTG TTAAGCATGA TGATCAAATA CTACATCAGT TTAAGAGTAT GTCTTTTTAC

2281 ATTACTGAAC CATCAGCTGA TTCAGGTGAC AATTATGGAA GTGATTTTTT CATTTCTGAT

2341 GAAGGAAAAA ATCTTAGATT TCAACTTCCT AAAGCTATTA CGCATTTGAA ATTGGTTAAT

2401 GTTAATGGAA ATAATAAGTT GGTACCATGT ACTAAAGATG GGAATGAACA TCCTGAAGGT

2461 ATGCCATCTG ATTTAACGGA TGAATATAGA TATATAGATC CTATTTTTGC TCATACATTT

2521 GAGAAACAAA GTTATTCTAA AAATAGTATT AGTGTTGGGT TAGTGGACTT CAGTAAATAT

2581 AAAGAAGGAT CTATGTTTAA ATTACAGCAT TATTCTGATG ATTATCATAT TCATAAGGAT

2641 GAACAAGGTA ATGTTATTAG GCCTAATAAC AGATCTTACG TTACAAAAGT GGATTTAGTA

2701 TATGATGATA AAGTTATTGG GATGTTGTCT GATAGTATAA ATCAATTTCA GGGTGATATT

2761 TTCATTTCTG CAAGCCTTAA TTATAGCCAC AATGATTTTC TTTCATCTAA GTACTTTCAG

2821 AAAGTTAATA TTGAGGCGTT AGAAAATGGA ATATATAGTG GAAGATATGA TGTAGGAGAT

2881 GGTGACCAAA TAGCAGGTCT TAATACTGAT ACAGGTTATA GTGATAAAGC TATTTTTTAC

2941 TTTAAAAATG ATAGCGCATC TACTGATATG CCGGCTAGTG ATGTTACTAC TATTTTACCT

3001 TATATAAATG AGCTTTAA
```

SEQ ID NO: 12 Ribosomal Protein L1 Protein Sequence
ORIGIN

```
  1 MTIFLESDDD KSNFKKTLEN GTKDKTNLDN TYYDYHHEDD MGNTEYHYVS LDRVDHVKMP

 61 EEPVGYGGDT LPIVPTTAAS VSGSDAGVAV GNVKDFEDNV FHHTSTIRND ELKIDLRIHT

121 LKDLSDKRLR EIEKGFNDTV TKFKNNFGLE PNDGETIFDL YLFDDKEQYN YYGKLYNLGI

181 SGSGGMTFYG NANVPYKIYV HQYGEILNLK HELTRALESY ASGHKLHGSD VNSRIFTEGL

241 ADYIQEDNSF IMRGLKDREI TSDVLKDSSG NVDHLSGVAV NENQRLSYSI GHAFVSFLQE

301 KYPKLISEYL NALKEDNIIR AKEIISMDKY PDFEPWVKSK DISLYLENMN VLKLGLGEKM

361 FSAESASYFE DQGVNKEYYH ENIYDMSGKL VGEMSPVVHY AQKNVIRIWN IASPDMIEVR

421 PEYNFLKLVT TPSGKSAYVY CDKNGHEYFN TKDYIDSAFN ILARYDVKLR ESSDALDIRG

481 RYSDAAKVFS KLPNADLLLD KFLEKIGYSS YKQIIMSNPE QLNSIKAYVV KEVFENFRES

541 EVKKVLSGES HPEVRNVLMD LTYVDLKSVI GVNGADIDSI ISNPDVMLRT AVLGKGNASG

601 ISLYVDDQKV GELSTEAGYC VKNLDTGKVY FMFHNVVGMI ASGYEDRAYM VVLEKDGKFT

661 TALVNNIQKA ADGNVVWDNQ FNHPNINNLH SNYKELLLND ASVKDYSHLA DVKFNKDDTV
```

-continued

```
721 IVKGELLDDK GTVSVDDDVH RAVVKHDDQI LHQFKSMSFY ITEPSADSGD NYGSDFFISD

781 EGKNLRFQLP KAITHLKLVN VNGNNKLVPC TKDGNEHPEG MPSDLTDEYR YIDPIFAHTF

841 EKQSYSKNSI SVGLVDFSKY KEGSMFKLQH YSDDYHIHKD EQGNVIRPNN RSYVTKVDLV

901 YDDKVIGMLS DSINQFQGDI FISASLNYSH NDFLSSKYFQ KVNIEALENG IYSGRYDVGD

961 GDQIAGLNTD TGYSDKAIFY FKNDSASTDM PASDVTTILP YINEL.
```

SEQ ID NO: 13 Type IV Secretory Protein VirD4 Nucleotide Sequence
ORIGIN

```
   1 ATGGATAGTA TAAGTGCAAA TCACATACGC AATATTTTAT TCCTTGTTTT AGGCGCATTT

  61 TTTGGACTGG AATTTTGCTT TTATTTATCA GGTGTATTAT TCATCTTAAT GGTCTGGGGA

 121 CCAAATTACC TAGATTTTAA TGCTATAAAT CCCAGTTTGA GTGATTTTCC AGACAGAATT

 181 TGGCCAACTA TTTTTGACTA TGTACAACAT TGGTGGAAGA ACCCTTCTGC ATACGATGCA

 241 GTTTTATTAC TTAAGCTAAT AACGTCATTA TGTACACCAG TAGGTATTCT AAGCATAGTA

 301 TTATGGAACC TTAGAAATAT ATTATTCGAT TGGAGGCCAT TTAAGAAGAA AGAATCACTG

 361 CATGGAGATT CAAGATGGGC AACAGAAAAA GATATTCGCA AAATAGGATT ACGTAGTAGA

 421 AAAGGAATAT TATTAGGGAA AGACAAGAGA GGATATCTCA TTGCAGATGG ATATCAACAT

 481 GCATTGTTAT TTGCACCAAC TGGATCCGGA AAAGGTGTAG GTTTTGTAAT ACCAAACTTA

 541 TTATTCTGGG AAGATTCTGT AGTAGTACAC GATATAAAAT TAGAGAACTA TGATCTTACA

 601 AGTGGGTGGA GAAAAAAAAG GGGACAAGAA GTTTTCGTGT GGAACCCAGC ACAACCTGAC

 661 GGTATAAGTC ACTGTTACAA CCCATTAGAT TGGATAAGCT CTAAGCCTGG ACAAATGGTA

 721 GATGATGTAC AAAAAATTGC CAATCTAATA ATGCCTGAAC AAGATTTTTG GTATAACGAA

 781 GCACGTAGTT TATTTGTAGG AGTAGTATTA TACTTACTAG CAGTACCAGA AAAAGTAAAA

 841 TCCTTTGGAG AAGTTGTAAG AACAATGCGC AGCGATGACG TAGTCTACAA CTTAGCAGTA

 901 GTACTAGACA CAATAGGGAA AAAGATTCAC CCAGTTGCAT ACATGAATAT AGCTGCATTT

 961 TTACAAAAAG CAGACAAAGA ACGCTCAGGT GTTGTATCAA CTATGAACTC ATCTTTAGAA

1021 TTATGGGCAA ACCCATTAAT AGATACAGCA ACAGCATCAA GTGATTTTAA TATTCAAGAA

1081 TTTAAAAGGA AAAAAGTAAC AGTATATGTT GGATTAACAC CAGATAATTT AACTCGTCTT

1141 AGACCTTTAA TGCAGGTATT TTATCAACAA GCTACAGAAT TTTTATGTAG AACTTTACCA

1201 TCAGATGATG AACCATATGG TGTACTGTTC TTAATGGATG AGTTTCCAAC ATTAGGAAAA

1261 ATGGAGCAAT TTCAAACAGG TATCGCATAT TTCCGTGGAT ATAGAGTTAG ACTATTTTTG

1321 ATTATTCAAG ATACTGAACA GCTTAAGGGT ATATATGAAG AAGCAGGAAT GAACTCATTC

1381 TTATCAAACT CTACTTATAG AATAACTTTT GCTGCAAATA ATATAGAAAC TGCAAATTTA

1441 ATATCACAGT TAATAGGAAA TAAAACTGTT AACCAAGAGT CTTTAAACAG ACCTAAATTT

1501 TTAGATTTGA ACCCTGCATC ACGTTCATTA CATATATCAG AAACACAAAG AGCTTTACTA

1561 TTACCTCAAG AAGTAATAAT GTTACCCAGA GATGAGCAAA TACTTTTAAT AGAATCTACT

1621 TATCCTATAA AATCAAAGAA AATAAAATAC TATGAAGACA AAAATTTTAC AAAAAAACTA

1681 TTAAAGAGTA CCTTTGTTCC AACTCAAGAG CCTTATGATC CCAACAAAAC AAAAACAGCA

1741 ACAAAAGAAA ACGAAGAACC TATGCCAAGT ATTGAAAGCG ATCTTCCTAA AAATACATCT

1801 GACAATACTG AAAACAATAT GGAAGATGGT GCAATGTACA GCAGCATAGA AGAAGATTAT

1861 GACGATGATG ATGATGATTT TAATTTTGAA GACTTAGATG AATATATGGA TGAAGAAGAA

1921 GATTATGATG ATGAAGAATA TGATGATATA GATTATGATG ATAATAACAA TAGTAATGAG

1981 GAGTATGAAG AAGATAATCC AGAAGAAGAT GACAATAGCA ATAATCTAGA CGATGAGGAA
```

-continued

2041 GAGGAAGAAG ATAATATTAT AGATTATGAA GATGAAGAAG AATATGATGA TAACATAGAC

2101 TACAAAGATG ATGACAATAA CTACAACAAA GATACCACTG ACGATCAAGA CTCAAAAAAA

2161 CATAATGAAT AG

SEQ ID NO: 14 Type IV Secretory Protein VirD4 Protein Sequence
ORIGIN

1 MDSISANHIR NILFLVLGAF FGLEFCFYLS GVLFILMVWG PNYLDFNAIN PSLSDFPDRI

61 WPTIFDYVQH WWKNPSAYDA VLLLKLITSL CTPVGILSIV LWNLRNILFD WRPFKKKESL

121 HGDSRWATEK DIRKIGLRSR KGILLGKDKR GYLIADGYQH ALLFAPTGSG KGVGFVIPNL

181 LFWEDSVVVH DIKLENYDLT SGWRKKRGQE VFVWNPAQPD GISHCYNPLD WISSKPGQMV

241 DDVQKIANLI MPEQDFWYNE ARSLFVGVVL YLLAVPEKVK SFGEVVRTMR SDDVVYNLAV

301 VLDTIGKKIH PVAYMNIAAF LQKADKERSG VVSTMNSSLE LWANPLIDTA TASSDFNIQE

361 FKRKKVTVYV GLTPDNLTRL RPLMQVFYQQ ATEFLCRTLP SDDEPYGVLF LMDEFPTLGK

421 MEQFQTGIAY FRGYRVRLFL IIQDTEQLKG IYEEAGMNSF LSNSTYRITF AANNIETANL

481 ISQLIGNKTV NQESLNRPKF LDLNPASRSL HISETQRALL LPQEVIMLPR DEQILLIEST

541 YPIKSKKIKY YEDKNFTKKL LKSTFVPTQE PYDPNKTKTA TKENEEPMPS IESDLPKNTS

601 DNTENNMEDG AMYSSIEEDY DDDDDDFNFE DLDEYMDEEE DYDDEEYDDI DYDDNNNSNE

661 EYEEDNPEED DNSNNLDDEE EEEDNIIDYE DEEEYDDNID YKDDDNNYNK DTTDDQDSKK

721 HNE.

SEQ ID NO: 15

MDIDNNNVTTSSTQDKSGNLMEVIMRILNFGNNSD

EKVSNEDTKVLVESLQPAVNDNVGNPSSEVGKEEN

APEVKAEDLQPAVDGSVEHSSSEVGKKVSETSKEE

STPEVKAEDLQPAVDGSIEHSSSEVGEKVSKTSKE

ESTPEVKAEDLQPAVDDSVEHSSSEVGEKVSETSK

EENTPEVKAEDLQPAVDGSIEHSSSEVGEKVSKTS

KEESTPEVKAEDLQPAVDDSVEHSSSEVGEKVSET

SKEENTPEVKAEDLQPAVDGSVEHSSSEVGEKVSK

TSKEESTPEVKAEDLQPAVDDSVEHSSSEVGEKVS

ETSKEENTPEVRAEDLQPAVDGSVEHSSSEVGEKV

SETSKEESTPEVKAEDLQPAVDSSIEHSSSEVGKK

VSETSKEESTPEVKAEDLQPAVDGSVEHSSSEVGE

KVSETSKEENTPEVKAEDLQPAVDGSVEHSSSEVG

EKVSETSKEENTPEVKAEDLQPAVDGSVEHSSSEV

GEKVSETSKEESTPEVKAEDLQPAVDDSVEHSSSE

VGEKVSETSKEESTPEVKAEDLQPAVDGSVEHSSS

EVGEKVSETSKEESTPEVKAEVQPVADGNPVPLNP

MPSIDNIDTNIIFHYHKDCKKGSAVGTDEMCCPVS

ELMAGEHVHMYGIYVYRVQSVKDLSGVFNIDHSTC

DCNLDVYFVGYNSFTNKETVDLI

SEQ ID NO: 16
KEENAPEVKAEDLQPAVDGSVEHSSSEVGKKVSETS

KEESTPEVKAEDLQPAVDGSIEHSSSEVGEKVSKTS

-continued

KEESTPEVKAEDLQPAVDDSVEHSSSEVGEKVSETS

KEENTPEVKAEDLQPAVDGSIEHSSSEVGEKVSKTS

KEESTPEVKAEDLQPAVDDSVEHSSSEVGEKVSETS

KEENTPEVKAEDLQPAVDGSVEHSSSEVGEKVSKTS

KEESTPEVKAEDLQPAVDDSVEHSSSEVGEKVSETS

KEENTPEVRAEDLQPAVDGSVEHSSSEVGEKVSETS

KEESTPEVKAEDLQPAVDSSIEHSSSEVGKKVSETS

KEESTPEVKAEDLQPAVDGSVEHSSSEVGEKVSETS

KEENTPEVKAEDLQPAVDGSVEHSSSEVGEKVSETS

KEENTPEVKAEDLQPAVDGSVEHSSSEVGEKVSETS

KEESTPEVKAEDLQPAVDDSVEHSSSEVGEKVSETS

KEESTPEVKAEDLQPAVDGSVEHSSSEVGEKVSETS

KEESTPEVKAE

SEQ ID NO: 18 *E. canis* P1401 (72, 89)
CPEVKAEDLQPAVDGSVEH

SEQ ID NO: 19 *E. canis* P1403 (64, 89)
CEVGKEENAPEVKAEDLQPAVDGSVEH

SEQ ID NO: 20 *E. canis*
CKEESTPEVKAEDLQPAVDGSVEHSSSEVGKKVSETS

SEQ ID NO: 21
XPEVKAEDLQPAVDGSVEHX,
wherein X = 0, 1, 2, 3, 4, 5, 6, 7, 8, 9, 10, 11, 12, 13, 14, or 15 amino acids.

SEQ ID NO: 22
CMLHVQNHVDQHTNHIEHDDYHFTGPT

SEQ ID NO: 23
CTNHIEHDDYHFTGPTSFEVNLSFEEKMEL

SEQ ID NO: 24
CTGPTSFEVNLSEEEKMELQEVSSIDS

SEQ ID NO: 25
XMLXVQNHVDQHTNHIEHDDYHFTXPT
Wherein the X at position 1 is C or is absent, the X at position 4 is H or Q and the X at position 25 is D or G.

SEQ ID NO: 26
XTNHIEHDDYHFTXPTSFEVNLSEEEKMEL
Wherein the X at position 1 is C or is absent and the X at position 14 is G or D.

SEQ ID NO: 27
XTXPTSFEVNLSEEEKMELQEVSSIDS
Wherein the X at position 1 is C or is absent, and the X at position 3 is G or D.

SEQ ID NO: 28
XTNHIEHDDYHFTXPT
Wherein the X at position 1 is C or is absent, and the X at position 14 is G or D.

SEQ ID NO: 29
XIXPTSFEVNLSEEEKMEL
Wherein the X at position 1 is C or is absent, and the X at position 3 is G or D.

SEQ ID NO: 30
XTNHIEHDDYHFTXPTSFEVNLSEXEKMEL
Wherein the X at position 1 is C or is absent, the X at position 14 is G or D, and the X at position 25 is E or G.

-continued

```
SEQ ID NO: 31
XTXPTSFEVNLSEXEKMELQEVSSIDS
Wherein the X at position 1 is C or is absent, the X at position 3 is
G or D, the X at position 14 is E or G.

SEQ ID NO: 32
XTXPTSFEVNLSEXEKMEL
Wherein the X at position 1 is C or is absent, the X at position 3 is
G or D, and the X at position 14 is G or F.

SEQ ID NO: 33
XMLXVQNHVDQHTNHIEHDDYHFTXPTSFEVNLSEXEKMELQEVSSIDS
Wherein the X at position 1 is absent or c, the X at position 4 is H
or Q, the X at position 25 is D or G, and the X at position 36 is F or
G.
```

Other embodiments of the invention provide the following polypeptides:

(a) SEQ ID NO:33, wherein the X at position 1 is absent or C, the X at position 4 is H or Q, the X at position 25 is D or G, and the X at position 36 is E or G;

(b) Amino acids 1-27 of SEQ ID NO:33, wherein the X at position 1 is C, the X at position 4 is H, the X at position 25 is D or G;

(c) Amino acids 13-41 of SEQ ID NO:33, wherein the X at position 25 is D or G, the X at position 36 is E or G; and a C is optionally present at the amino terminus;

(d) Amino acids 24-49 of SEQ ID NO:33, wherein the X at position 25 is D or G, the X at position 36 is E or G, and a C is optionally present at the amino terminus;

(e) Amino acids 1-27 of SEQ ID NO:33, wherein the X at position 1 is C or absent, and wherein the X at position 25 is D or G;

(f) Amino acids 13-41 of SEQ ID NO:33, wherein the X at position 25 is D or G, the X at position 36 is E or G, and a C is optionally present at the amino terminus;

(g) Amino acids 24-49 of SEQ ID NO:33, wherein the X at position 25 is D or G, the X at position 36 is E or G, and a C is optionally present at the amino terminus;

(h) Amino acids 13-27 of SEQ ID NO:33, wherein the X at position 25 is D or G, and a C is optionally present at the amino terminus;

(i) Amino acids 24-41 of SEQ ID NO:33, wherein the X at position 25 is D or G, the X at position 36 is E or G, and a C is optionally present at the amino terminus;

(j) Amino acids 13-41 of SEQ ID NO:33, wherein the X at position 25 is D or G, the X at position 36 is E or G, and a C is optionally present at the amino terminus;

(k) Amino acids 24-49 of SEQ ID NO:33, wherein the X at position 25 is D or G, the X at position 36 is E or G, and a C is optionally present at the amino terminus;

(l) Amino acids 24-41 of SEQ ID NO:33, wherein the X at position 25 is D or G, the X at position 36 is E or G, and a C is optionally present at the amino terminus.

---

We claim:

1. A method of distinguishing between animals that have been (a) infected with *Ehrlichia canis*; and (b) animals that have not been infected with *E. canis* regardless of whether the animal has been vaccinated for *E. canis*, the method comprising:

(a) contacting a biological sample from an animal with one or more purified polypeptides that do not specifically bind to antibodies that are a component of the animal's immune response to an *E. canis* vaccine; wherein the one or more purified polypeptides comprise SEQ ID NOs: 22, 23, 24, 24, 25, 27, 28, 29, 30, 31, 32, or 33, wherein the one or more purified polypeptides are 15 to 75 amino acids in length ; and (b) detecting whether antibodies in the biological sample specifically bind to the one or more purified *E. canis* polypeptides; wherein, if antibodies in the biological sample specifically bind to the one or more purified polypeptides, then the animal has been infected with *E. canis*.

2. The method of claim 1, wherein the one or more purified polypeptides are linked to a heterologous amino acid sequence, an indicator reagent, an amino acid spacer, an amino acid linker, a signal sequence, a stop transfer sequence, a transmembrane domain, a protein purification ligand, or a combination thereof.

3. The method of claim 1, wherein the method further comprises detecting the amount of specific binding.

4. The method of claim 1, wherein the one or more purified polypeptides are immobilized to a solid support.

5. A method for determining the presence or absence of an antibody or antigen-binding fragments thereof that are specific for *E. canis*, in a test sample, wherein the antibody or antigen-binding fragments specifically bind to one or more purified polypeptides consisting of the amino acid sequence set forth in SEQ ID NOs: 22-33 or combinations thereof comprising:

(a) contacting the test sample with one or more purified polypeptides comprising SEQ ID NOs: 22, 23, 24, 25, 26, 27, 28, 29, 30, 31, 32, or 33 wherein the one or more purified polypeptides are 15 to 75 amino acids in length, and wherein the one or more purified polypeptides specifically bind an antibody that is specific for *E. canis*, under conditions suitable for specific binding of the one or more purified polypeptides to the antibodies or antigen-binding fragments thereof; and (b) detecting the presence of specific binding of the one or more purified polypeptides to the antibodies or antigen-binding fragments thereof;

wherein the presence of specific binding of the one or more purified polypeptides to the antibodies or antigen-binding fragments indicates the presence of the antibodies or antigen-binding fragments thereof specific for *E. canis* in the test sample and wherein the absence of specific binding indicates the absence of the antibody or antigen binding fragments.

6. The method of claim 5, wherein the one or more purified polypeptides are linked to a heterologous amino acid sequence, an indicator reagent, an amino acid spacer, an amino acid linker, a signal sequence, a stop transfer sequence, a transmembrane domain, a protein purification ligand, or a combination thereof.

7. The method of claim 5, wherein the method further comprises detecting the amount of specific binding.

8. The method of claim 5, wherein the one or more purified polypeptides are immobilized to a solid support.

9. A method of distinguishing between an animal that has been infected with *E. canis* from an animal that has not been infected with *E. canis*, comprising:

(a) contacting a biological sample from an animal with one or more purified polypeptides wherein the one or more purified polypeptides comprise SEQ ID NOs: 22, 23, 24, 25, 26, 27, 28, 30, 31, 32, or 33, wherein the one or more purified polypeptides are 15 to 75 amino acids in length ; and (b) detecting whether antibodies in the biological sample specifically bind to the one or more purified polypeptides;

wherein, if antibodies in the biological sample specifically bind to the one or more purified polypeptides, then the animal has been infected with *E. canis*.

10. The method of claim 9, wherein the one or more purified polypeptides are linked to a heterologous amino acid sequence, an indicator reagent, an amino acid spacer, an amino acid linker, a signal sequence, a stop transfer sequence, a transmembrane domain, a protein purification ligand, or a combination thereof.

11. The method of claim 9, wherein the method further comprises detecting the amount of specific binding.

12. The method of claim 9, wherein the one or more purified polypeptides are immobilized to a solid support.

* * * * *

UNITED STATES PATENT AND TRADEMARK OFFICE

CERTIFICATE OF CORRECTION

PATENT NO. : 7,888,054 B2
APPLICATION NO. : 12/262709
DATED : February 15, 2011
INVENTOR(S) : Krah et al.

It is certified that error appears in the above-identified patent and that said Letters Patent is hereby corrected as shown below:

Col. 131, line 65 cancel "NOs: 22, 23, 24, 24, 25, 27, 28, 29, 30, 31, 32, or 33," and insert --NOs: 22, 23, 24, 25, 26, 27, 28, 29, 30, 31, 32, or 33,--
Col. 134, line 14-15, cancel "NOs: 22, 23, 24, 25, 26, 27, 28, 30, 31, 32, or 33" and insert --NOs: 22, 23, 24, 25, 26, 27, 28, 29, 30, 31, 32, or 33,--

Signed and Sealed this
Twenty-ninth Day of March, 2011

David J. Kappos
*Director of the United States Patent and Trademark Office*